United States Patent [19]

Salstrom et al.

[11] Patent Number: 4,634,678

[45] Date of Patent: Jan. 6, 1987

[54] PLASMID CLONING AND EXPRESSION VECTORS FOR USE IN MICROORGANISMS

[75] Inventors: John S. Salstrom, Edina; Dawn Newman; Douglas F. Harbrecht, both of Hopkins; Shiu-Lok Hu, Minnetonka, all of Minn.

[73] Assignee: Molecular Genetics Research and Development Limited Partnership, Minnetonka, Minn.

[21] Appl. No.: 449,187

[22] Filed: Dec. 13, 1982

[51] Int. Cl.$^4$ .................. C12N 1/00; C12N 15/00; C12N 1/20; C12P 21/00; C12P 21/02; C12P 19/34

[52] U.S. Cl. ..................... 435/317; 435/68; 435/90; 435/91; 435/172.3; 435/253; 935/29; 935/39; 935/40; 935/41; 935/42; 935/43; 935/44; 935/45; 935/46

[58] Field of Search ............ 435/68, 70, 91, 172.3, 435/253, 317; 935/29, 39-46

[56] References Cited

U.S. PATENT DOCUMENTS

| | | | |
|---|---|---|---|
| 4,237,224 | 12/1980 | Cohen et al. | 435/68 |
| 4,304,863 | 12/1981 | Collins et al. | 435/172 |
| 4,332,892 | 6/1982 | Ptashue et al. | 435/68 |
| 4,338,397 | 7/1982 | Gilbert et al. | 435/68 |
| 4,342,832 | 8/1982 | Goeddel et al. | 435/172 |
| 4,349,629 | 9/1982 | Carey et al. | 435/172 |
| 4,371,625 | 2/1983 | Tiollais | 435/317 |
| 4,374,927 | 2/1983 | Suinsky et al. | 435/68 |
| 4,436,815 | 3/1984 | Hershberger et al. | 435/68 |
| 4,503,142 | 3/1985 | Berman et al. | 435/68 |

FOREIGN PATENT DOCUMENTS

| | | |
|---|---|---|
| 1557774 | 12/1979 | United Kingdom . |
| 2100738A | 6/1983 | United Kingdom . |

OTHER PUBLICATIONS

Lewin: *Gene Expression*-3, John Wiley & Sons, New York, 1977, pp. 330-347.
Daniels et al: in *Genetic Maps*, O'Brien (ed.), Cold Spring Harbor Laboratory, 1982, pp. 1-9.
Rosenberg et al: Ann. Rev. Genet. 13, 319 (1979).
Notani, et al., Abstract, The American Society for Microbiology, Miami, Fla., vii, (1981).
Guarente et al., Cell 20: 543-553 (1980).
Bernard and Helinski, *Methods in Enzymology* 68:482-492, Academic Press (1979).
Bolivar and Backman, *Methods in Enzymology* 68:245-261, Academic Press (1979).
Itakura et al., Science 198: 1056-1063 (1977).
Villa-Komaroff et al., Proc. Natl. Acad. Sci., U.S.A 75:3727-3731 (1978).
Seeburg et al., Nature 276:795-798 (1978).
Mercereau-Puijalon et al., Nature 275:505-510 (1978).
Fraser et al., Proc. Natl. Acad. Sci., U.S.A. 75:5936-5940 (1978).
Backman and Ptashne, Cell 13:65-71 (1978).
Roberts et al., Proc. Natl. Acad. Sci., U.S.A 76: 760-764 (1979).
Casadaban et al., J. Bacteriol. 143:971-980 (1980).

*Primary Examiner*—James Martinell
*Attorney, Agent, or Firm*—Pennie & Edmonds

[57] ABSTRACT

DNA cloning and expression vectors capable of replication in a microbial host comprising from upstream to downstream (a) at least one promoter; (b) a translation start codon; (c) a cloning segment which provides a means for inserting nucleic acid sequences and (d) a sequence coding for a detectable gene product, out of translational phase with the translation start codon but capable of being readjusted to the translational phase of said start codon by insertion into the cloning segment of nucleic acid sequences containing the proper number of nucleotides for readjustment, said gene product providing a means for detecting expression of inserted nucleic acid sequences.

38 Claims, 44 Drawing Figures

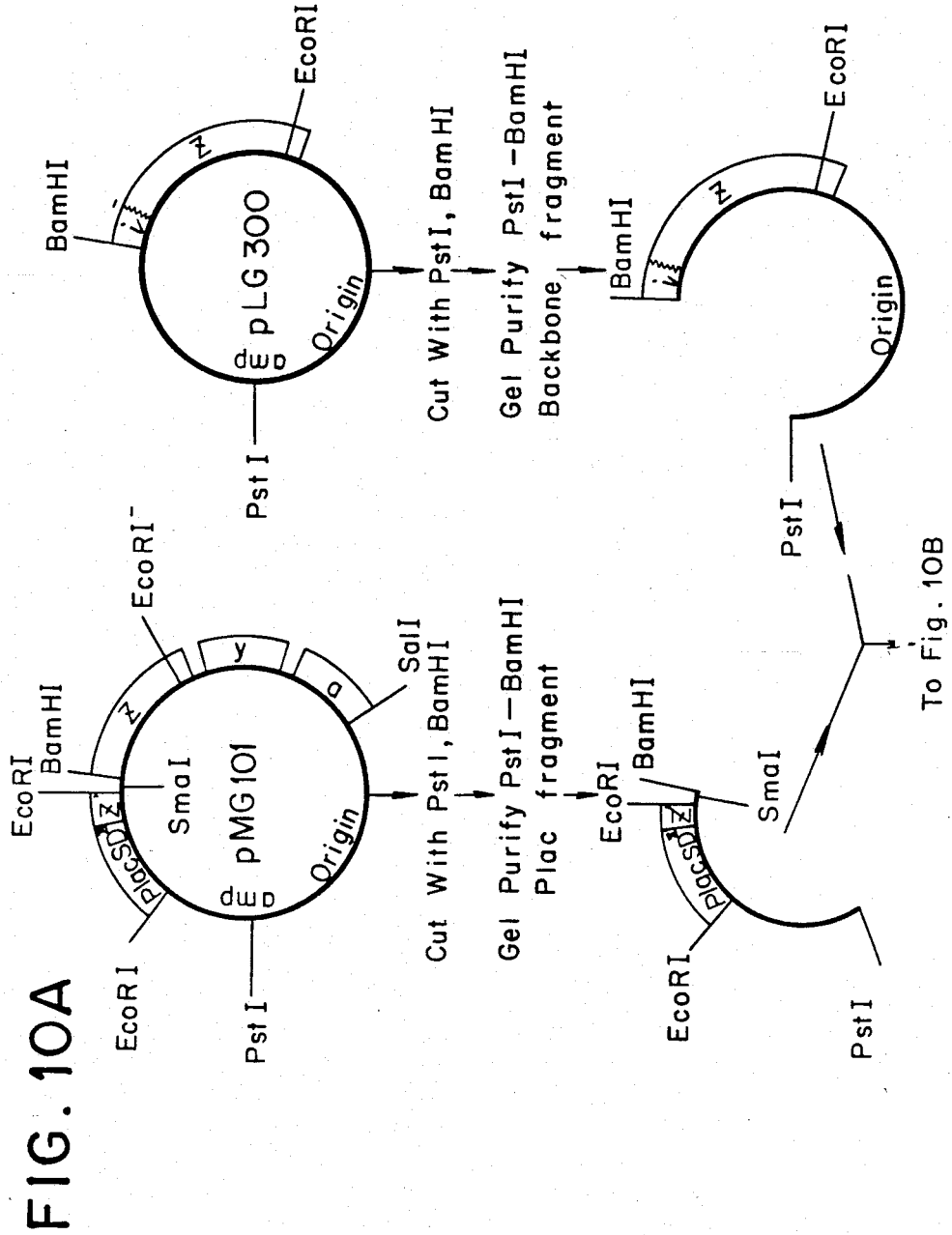

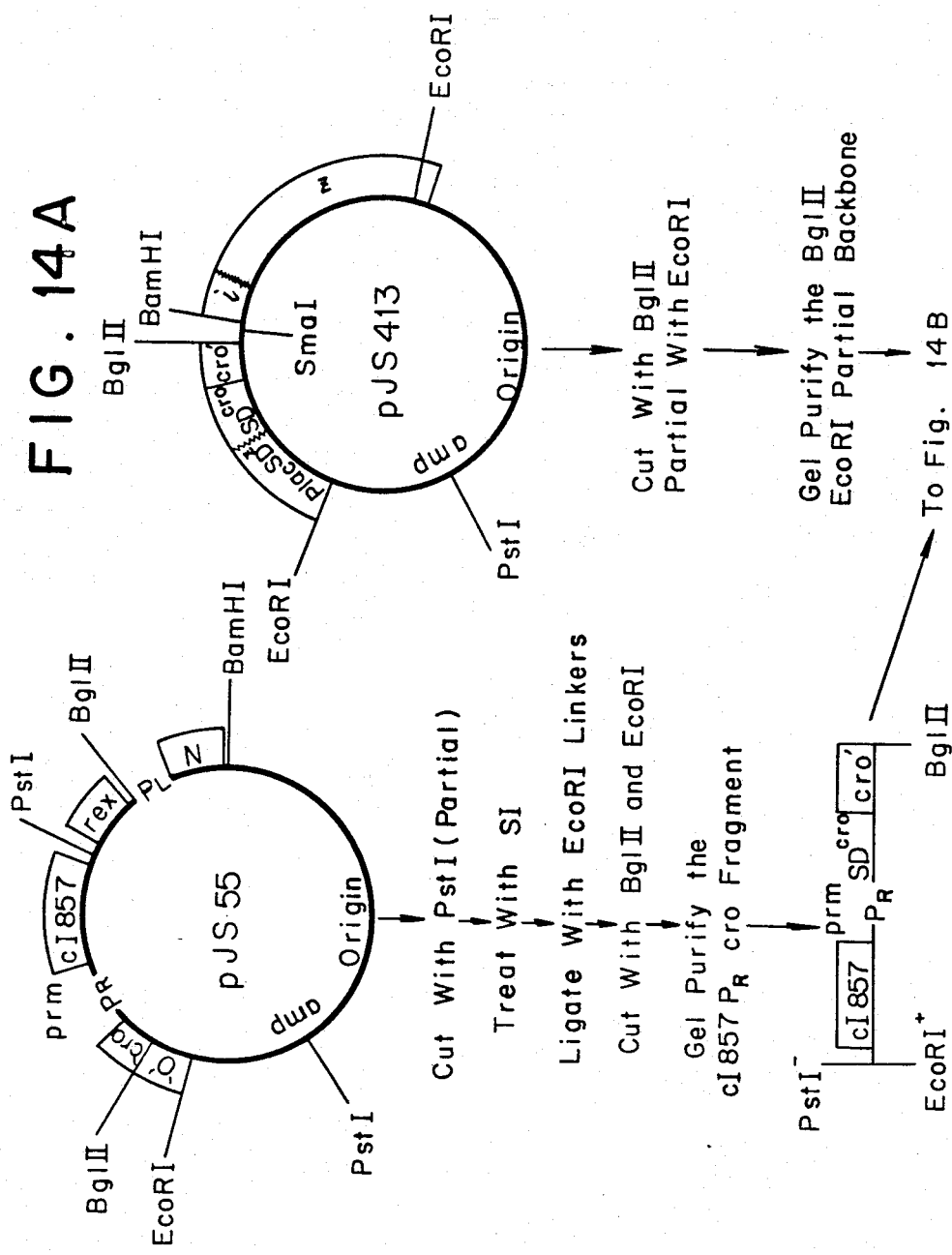

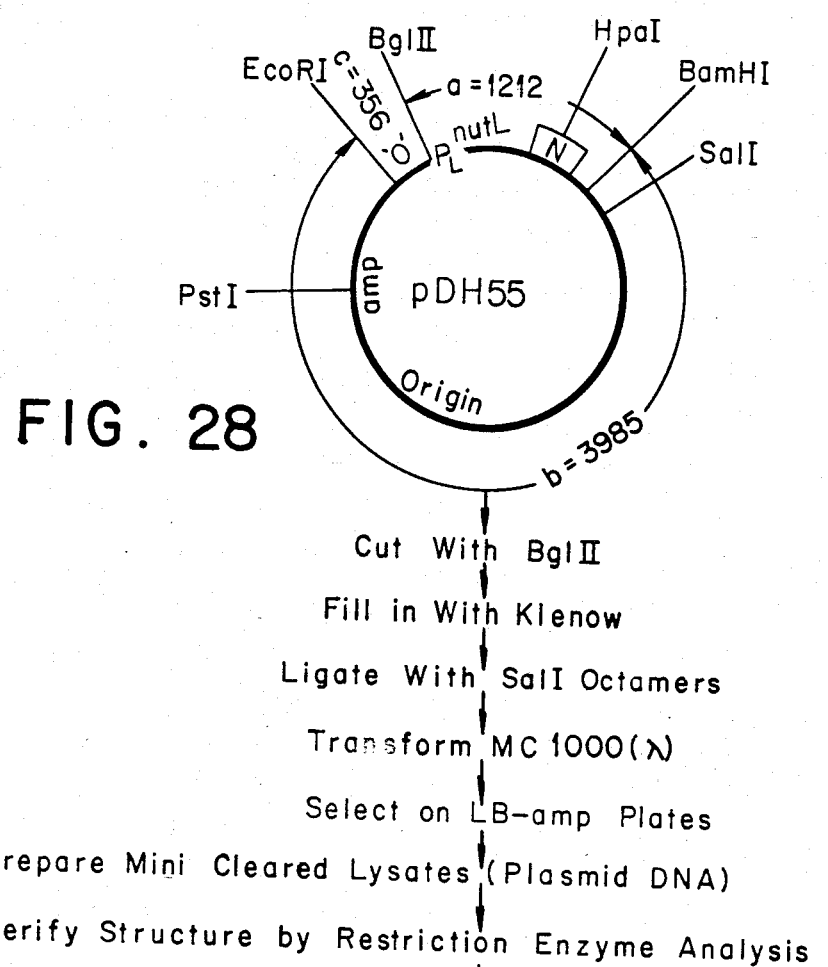
FIG. 28
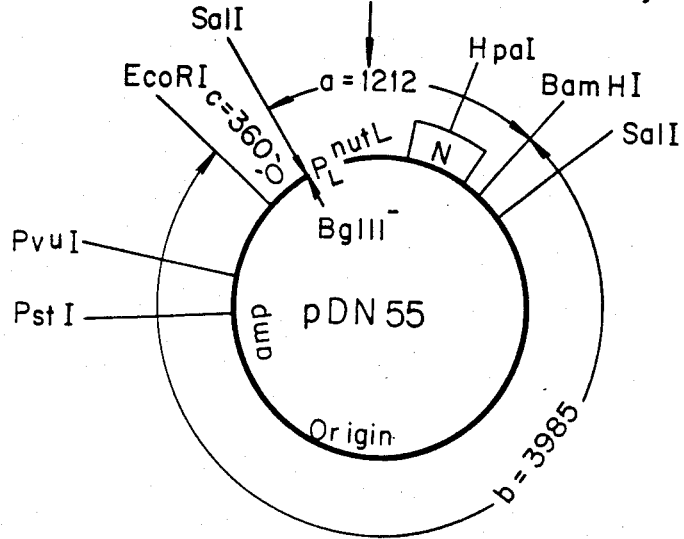

Cut With PstI, HindIII

Gel Purify the PstI-HindIII
P_L-Bearing Fragments
(1310 to 1383 b.p.)

PLASMID CLONING AND EXPRESSION VECTORS FOR USE IN MICROORGANISMS

TABLE OF CONTENTS

1. Introduction
2. Background of the Invention
   2.1. Recombinant DNA Technology and Gene Expression
   2.2 Plasmid Cloning and Expression Vehicles
3. Summary of the Invention
4. Brief Description of the Figures
5. Detailed Description of the Invention
   5.1. pJS413
      5.1.1. Isolation of Plasmid pJS413
      5.1.2. Structure and Description of pHS413
      5.1.3. Use of pJS413 as a Cloning Vehicle
   5.2. Derivatives of pJS413
      5.2.1. Changes in the Linker
      5.2.2. Elimination of the EcoRI Site in lacZ
      5.2.3. Substitution of the $tet^R$ Marker for $amp^R$
      5.2.4. Changes in the cro Segment
      5.2.5. Isolation of Over-production Mutants
      5.2.6. Changes in Plasmid Copy Number
   5.3. pMG101
      5.3.1. Isolation of Plasmid pMG101
      5.3.2. Structure and Description of pMG101
      5.3.3. Use of pMG101 as a Cloning Vehicle
   5.4. Derivatives of pMG101
   5.5. pJS400
      5.5.1. Isolation of Plasmid pJS400
      5.5.2. Structure and Description of pJS400
      5.5.3. Use of pJS400 as a Cloning Vehicle
   5.6. Derivatives of pJS400
   5.7. pDN455
      5.7.1. Isolation of Plasmid pDH455
      5.7.2. Structure and Description of pDN455
      5.7.3. Use of pDN455 as a Cloning Vehicle
   5.8. Derivatives of pDN455
      5.8.1. Changes in the Linker
      5.8.2. Changes in the cro Segment
      5.8.3. Isolation of Over-production Mutants
      5.8.4. Isolation of pDN455t
      5.8.5. Elimination of the EcoRI Site in lacZ
      5.8.6. Substitution of the $tet^R$ Marker for $amp^R$
   5.9. pJS55 and pDH55
      5.9.1. Isolation of Plasmid pDH55
      5.9.2. Structure and Description or pJS55 and pDH55
      5.9.3. Use of pJS55 and pDH55 as Cloning Vehicles
   5.10. pDH26, pDH36 and pDH72
      5.10.1. Isolation of Plasmids pDH26, pDH36, and pDH72
      5.10.2. Structure and Description of pDH26, pDH436 and pDH72
      5.10.3 Use of Plasmids pDH26, pDH36 and pDH72 as Cloning Vehicles
   5.11. pDH428 and pDH438
      5.11.1. Isolation of Plasmids pDH428 and pDH438
      5.11.2. Structure and Description of pDH428 and pDH438
   5.12 pDH800 Series
      5.12.1. Isolation of pDN55
      5.12.2. Isolation of the pDH500 Series
      5.12.3. Isolation of the pDH600 Series
      5.12.4. Isolation of the pDH700 Series
      5.12.5. Isolation of the pDH800 Series
      5.12.6. Structure and Description of PDH800 Series
      5.12.7. Use of pDH800 Plasmids and Its Derivatives as Cloning Vehicles
6. Examples
   6.1. Conditions for Restriction Enzyme Digestions
   6.2. DNA Modification
      6.2.1. Modification of DNA Fragments with Bal31 Nuclease
      6.2.2. Modification of DNA Fragments with Sl Nuclease
      6.2.3. Modification of DNA Fragments with DNA Polymerase I
      6.2.4 Modification of DNA Fragments with Synthetic Oligonucleotide Linkers and Adapters
   6.3. Ligations
   6.4. Transformation
   6.5. Preparation of Mini-cleared Lysates
   6.6. Large-scale Cesium chloride Plasmid Preparation
   6.7 Gel Purification of DNA Fragments
      6.7.1. Electro-elution
      6.7.2. Low Melting Temperature Gel
      6.7.3. Deposit of Microorganisms

1. INTRODUCTION

This invention relates to novel plasmids constructed by recombinant DNA technology and to their use as vectors for closing nucleic acid sequences and for expressing the peptides or proteins encoded by such sequences. Many peptides of interest and/or potential industrial or medical importance, including hormones, enzymes and viral capsid antigens, are difficult to isolate in sufficient quantities from their natural sources. One approach to this problem has been to utilize methods of recombinant DNA technology to excise gene sequences coding for peptide compounds of interest and recombine them into self-replicating vectors. When placed in appropriate host cells, the recombined vectors can direct synthesis of desired peptides in amounts significantly greater than can be isolated from nature.

The success of processes for the production of (poly)-peptides by recombinant DNA methods is largely dependent upon the DNA vector chosen for cloning and expression. Ideally, the vector should combine a variety of features such as convenient restriction enzyme cleavage sites to facilitate nucleic acid insertion, elements to ensure high copy number and efficient transcription and translation, a regulatory mechanism to control expression of the inserted sequence, a marker gene to detect the presence of the vector in its host, as well as an indicator that expression of the cloned insert has occurred. The plasmid vehicles of this invention were devised with this spectrum of attributes in mind. A series of plasmids has been assembled in which the following elements and features have been varied in the individual constructions: (a) the promoter; (b) the system of regulation; (c) the ribosome binding region; (d) the cloning segment (particularly the translational reading phase of the various restriction sites therein); (e) the capacity to "shot-gun" clone random DNA fragments as well as the capacity to clone discrete segments of DNA directly; (f) the β-galactosidase fusion capabilities; (g) the plasmid copy number; and (h) the drug resistance marker. They have been used successfully in *E. coli* for the expression of polypeptides such as reverse transcriptase, bovine growth hormone, and the capsid proteins of viruses such as herpes simplex virus.

2. BACKGROUND OF THE INVENTION

2.1. Recombinant DNA Technology and Gene Expression

Recombinant DNA technology involves insertion of specific DNA sequences into a DNA vector (vehicle) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. In recent years several general methods have been developed which enable construction of recombinant DNA molecules. For example, U.S. Pat. No. 4,237,224 to Cohen and Boyer describes production of such recombinant plasmids using restriction enzymes and a method known as ligation. These recombinant plasmids are then introduced, by means of transformation, and replicated in unicellular organisms. Another method for introducing recombinant DNA molecules into unicellular organisms is transduction or transfection which utilizes bacteriophage vectors and an in vitro packaging system (see Collins and Hohn in U.S. Pat. No. 4,304,863).

Regardless of the method used for construction, the recombinant DNA molecule must be able to survive and replicate in the host cell. The recombinant DNA molecule should also have a marker function which allows the selection of host cells so transformed (or transduced) by the recombinant DNA molecule. In addition, if all of the proper replication, transcription and translation signals are correctly arranged on the plasmid, the foreign gene will be properly expressed in the transformed cells and their progeny.

The processes of transcription and translation represent two levels of control of gene expression. Transcription of DNA is dependent upon the presence of a promoter which is a DNA sequence that directs the binding of RNA polymerase and thereby promotes transcription of a gene or a group of linked genes (operon). Promoters vary in their "strength", i.e., their ability to promote transcription. For the purpose of molecular cloning it is desirable to use strong promoters in order to obtain a high level of transcription and, hence, expression of the gene. Depending upon the host cell system utilized, any one of a number of suitable promoters may be used. For instance, when cloning in an *E. coli* host cell system, any of the promoters isolated from *E. coli*, its bacteriophages or plasmids may be used. More specifically, the $P_R$ and $P_L$ promoters of coliphage λ direct high levels of transcription of adjacent DNA segments. In addition, the recA and lac promoters from *E. coli* provide high levels of gene transcription of adjacent fragments. Furthermore, other *E. coli* promoters or synthetic DNA sequences may be used to provide the signal for transcription of the inserted gene.

Specific initiation signals are also required for efficient translation of messenger RNA (mRNA) in procaryotic cells; such procaryotic signals differ from those of eucaryotes. Efficient translation of mRNA in procaryotes requires a multipartite ribosome binding site on the mRNA including a short Shine-Dalgarno (SD) nucleotide sequence and the start codon (AUG) (located just 3' to the SD sequence) which codes for the amino-terminal methionine of the protein. The SD sequences have complementarity to the 3'-end of the 16S ribosomal RNA (rRNA) and probably promote binding of mRNA to ribosomes by duplexing with the rRNA to allow correct positioning of the ribosome [Shine and Dalgarno, Nature 254: 34–38 (1975)].

Translation initiation signals may vary in "strength" as measured by the quantity of protein synthesized relative to the amount of gene-specific mRNA. Any SD-AUG combination that can be utilized by host cell ribosomes may be employed; such combinations include, but are not limited to, the SD-AUG combination from the cro gene or the N gene of coliphage λ, or from the *E. coli* tryptophan E, D, C, B or A genes. Additionally, any SD-AUG combination produced by recombinant DNA or other synthetic technique may be used.

Any of the methods previously described (e.g., U.S. Pat. No. 4,237,224) for the insertion of DNA fragments into a vector may be used to ligate a promoter segment, a ribosome binding region and any other control elements into specific sites within the vector.

Similarly, a gene of interest (or any portion thereof) can be inserted into an expression vector at a specific site in relation to the promoter and other control elements so that the gene sequence can be expressed correctly on the plasmid. The resultant recombinant DNA molecule is then introduced into appropriate host cells by transformation, transduction or transfection (depending upon the vector/host cell system). Transformants are selected on the basis of the expression of an appropriate marker gene included, and known to be able to be expressed, on the vector in an appropriate host cell, such as ampicillin-resistance or tetracycline-resistance in *E. coli*, or thymidine kinase activity in eucaryotic host cell systems. Expression of such marker proteins indicates that the recombinant DNA molecule entered the cell and is intact. Expression vectors which are commercially available (Bethesda Research Laboratories, Inc., Rockville, MD) include the following vectors or their derivatives SV40 and adenovirus vectors, yeast vectors, bacteriophage vectors such as λgt-WES-λB, Charon 28, Charon 4A, gt-λBC, GT-1-λB, M13mp7, or plasmid DNA vectors such as pBR322, pAC105, pVH51, pACY177, pKH47, pACYC184, pUB110, pMB9, pBR325, ColE1, pSC101, pBR313, pML21, RSF2124, pCR1 or RP4.

In addition, host cell strains may be chosen which repress the action of the promoter unless specifically induced. Such host cells bear genes coding for repressor protein which specifically interacts with the operator region located near or overlapping the promoter to block transcription. In this way greater than 95% of the activity of the promoter can be repressed in uninduced cells. In certain operons, the addition of specific inducer substances (which prevent repressor protein from remaining bound to the operator) may be necessary for efficient transcription and translation of the inserted DNA. For example, the lac operon may be induced by the addition of lactose or IPTG (isopropylthio-β-D-galactoside, an analog of lactose). A variety of other operons, such as trp, pro, etc., are under difference controls; the trp operon is derepressed when tryptophan is absent in the growth medium. The $P_R$ and $P_L$ promoters of λ are derepressed by an increase in temperature if the temperature-sensitive repressor (product of the λcI857 gene) is used. Thus, expression of the inserted gene sequence can be controlled. This is important if the protein product of the cloned gene is lethal to host cells. In such cases, the foreign gene can be replicated but not expressed during growth of the transformants. After the cells reach a suitable density in the growth medium, the promoter can be induced for production of the protein.

Many factors complicate the expression of eucaryotic genes in procaryotes even after the proper signals are inserted and appropriately positioned. A clear understanding of the nature of these factors and the mechanisms by which they operate is presently lacking. One such factor is the presence of an active proteolytic system in *E. coli* and other bacteria. This protein-degrading system appears to selectively destroy "abnormal" or foreign proteins such as eucaryotic proteins. A tremendous utility, therefore, would be afforded by the development of a means to protect eucaryotic proteins expressed in bacteria from proteolytic degradation. One strategy is to construct hybrid genes in which the eucaryotic sequence is ligated in phase (i.e., in the correct reading frame) with a procaryotic gene resulting in a fusion protein product (a protein that is a hybrid of procaryotic and foreign or eucaryotic amino acid sequences) thereby perhaps causing the cell to regard the protein as "self" and spare it from proteolysis.

Construction of hybrid genes was the approach used in the molecular cloning of genes encoding a number of eucaryotic proteins, such as somatostatin [Itakura et al., Science 198: 1056 (1977)], rat pre-proinsulin [Villa-Komaroff et al., Proc. Natl. Acad. Sci., U.S.A. 75: 3727 (1978)], growth hormone [Seeburg et al., Nature 276: 795 (1978)], and ovalbumin-like protein [Mercereau-Puijalon et al., Nature 275: 505 (1978)]. Additionally, procaryotic promoters have been ligated to such fusion gene sequences in the case of ovalbumin [Fraser et al., Proc. Natl. Acad. Sci., U.S.A. 75: 5936 (1978)]and $\beta$-globin [Guarente et al., Cell 20: 543 (1980)]. Although the molecular cloning and expression of several eucaryotic genes has been accomplished (see e.g., U.S. Pat. No. 4,332,892 to Ptashne et al. and U.S. Pat. No. 4,338,397 to Gilbert and Talmadge), the state of the art is such that expression of foreign or eucaryotic genes in procaryotic host cells can not be routinely performed.

2.2. Plasmid Cloning and Expression Vehicles

Recombinant DNA technology has been applied by numerous investigators in recent years to the construction of maximally expressing plasmids and other nucleic acid cloning vectors. That is, the construction of vehicles capable of: (a) replicating in a host cell at high copy number, and (b) directing high levels of transcription and/or translation has been the objective of studies ultimately aimed at overproducing (poly)peptide products of gene sequences inserted into the expression vehicle using restriction endonuclease cleavage and ligation.

For example, Backman and Ptashne [Cell 13: 65-71 (1978)]inserted the *E. coli* chromosomal lac promoter (or multiple copies thereof) into *E. coli* plasmid pMB9 bearing the cI (repressor) gene from bacteriophage $\lambda$. Recombinant plasmids so created displayed different levels of transcription and translation of the cI gene. One plasmid, pKB252, which contains two functional lac promoters, directed the synthesis of twice as much repressor as a similar plasmid, pKB255, bearing only one lac promoter. Another plasmid constructed by these investigators, pKB280, had a hybrid ribosome binding site containing the SD sequence of lacZ and the AUG start codon of the $\lambda$cI gene. This plasmid directed very high levels of $\lambda$ repressor protein synthesis.

To examine the effect of gene-promoter separation on protein production, Roberts et al. [Proc. Natl. Acad. Sci., U.S.A. 76(2): 760-764 (1979)]developed a "portable promoter" system which allowed them to insert the lacZ promoter region at virtually any distance from the $\lambda$cro gene on plasmids derived from pBR322 [Bolivar and Backman, Methods in Enzymology 68: 245-267, Academic Press (1979)]. The inserted lac promoters bore the $SD^Z$ sequence (but not a start codon) and the resulting plasmids contained hybrid $SD^Z$-$SD^{cro}$ regions upstream from the AUG start codon of cro. Several of these plasmids, particularly pTR213, were exremely high expressors of Cro protein, although there was no direct correlation between $SD^Z$-$AUG^{cro}$ separation and Cro protein production.

Other plasmid construction strategies have included the incorporation of an indicator, i.e., a marker to detect the expression of cloned genes easily. This has been accomplished by inserting genes (or portions thereof) into plasmids which code for conveniently assayed enzymes. For instance, Guarente et al. [Cell 20: 543-553 (1980)]inserted the carboxy-terminus of the lacZ gene (coding for $\beta$-galactosidase) into three sets of plasmids that could be opened by restriction enzyme cleavage to expose the Z gene in any of the three translational reading frames. Amino-terminal fragments of genes of interest could be inserted upstream of the Z gene segment. Using the "portable" lac promoter, those plasmids bearing fragments inserted in phase with the Z gene could be directed to yield fusion proteins. Since the fusion protein exhibits $\beta$-galactosidase activity, the need for a functional or immunological assay for the gene product of interest is eliminated. After high expressors are selected based on the level of $\beta$-galactosidase activity, the gene of interest can be reconstituted to yield the unfused product. Other assayable enzymes can be cloned into plasmids to facilitate detection of gene expression. For example, Bernard and Helinski [Methods in Enzymology 68: 482-492, Academic Press (1979)]have inserted the trpA gene into their plasmids as an assay for the translation of the cloned gene segment which is under the control of the $P_L$ promoter of bacteriophage $\lambda$.

3. SUMMARY OF THE INVENTION

This invention provides novel plasmids capable of autonomous replication in host microorganisms and useful as vectors for the cloning and expression of recombined or inserted nucleic acid sequences. Methods and compositions used to construct the plasmids of this invention are also provided. In essence, recombinant DNA techniques, as well as other microbiological and molecular biological techniques, are employed to arrange a variety of control elements, restriction sites (cloning segments), markers for screening (e.g., antibiotic resistance), and markers for detecting gene expression (i.e., sequences coding for detectable gene products, such as enzymes) in novel combinations in/on plasmid vehicles. The plasmids so created are unlike any others constructed previously and unlike any normally occurring in nature. Their unique combinations of features are summarized in Table I.

TABLE I

PLASMID CLONING AND EXPRESSION VEHICLES: UNIQUE COMBINATIONS OF FEATURES

| NAME | PROMOTER | SD | REGULATOR OF GENE EXPRESSION | N—TERMINUS/LINKER/ COOH—TERMINUS (PHASE) | DRUG MARKER | DERIVATIVES |
|---|---|---|---|---|---|---|
| pJS413 | Plac[1] | lacZ-λcro | lac repressor | cro(BglII-SmaI-BamHI)I-Z (+2) | amp$^R$ | pDN413(0), pDN413RI$^-$ pDNT413 (tet$^R$), pDNT413RI$^-$ pSH113 (OP1Δ6), croΔ series (FIG. 6) |
| pHK413 | " | " | " | cro(BglII-HindIII-SmaI-BamHI)I-Z (+1) | " | |
| pHK412 | " | " | " | cro(BglII-HindIII-SmaI-BamHI-BamHI$^-$)I-Z (0) | " | |
| pHK414 | " | " | " | cro(BglII-HindIII-SmaI-BamHI-BamHI$^-$)I-Z (+2) | " | |
| pHK410 | " | " | " | cro(BglII-HindIII-BamHI-BamHI$^-$)I-Z (0) | " | |
| pHK411 | " | " | " | cro(BglII-HindIII-BamHI-BamHI$^-$)I-Z (+1) | " | |
| pMG101 | Plac[2] | lacZ | " | Z(EcoRI-SmaI-BamHI)Z (+2) | " | pJSIIIb (0) |
| pJS400 | " | " | " | Z(EcoRI-SmaI-BamHI)I-Z (+1) | " | pDN400 (0) |
| pDN455 | P$_R$ | λcro | cI857λ repressor[5] | cro(BglII-SmaI-BamHI)I-Z (+2) | " | croΔ series, pDN456, pDN456RI$^-$, pDNT456, pDNT456RI$^-$ |
| pDH55 | P$_L$ | λN | λrepressor[3,4] | N(HpaI)N (0) | " | |
| pDN55 | " | " | " | N(HpaI)N (0) | " | |
| pDH26 | " | " | λrepressor[3,5] | N(HpaI$^-$-SmaI$^-$-BamHI)Z (0) | " | |
| pDH36 | " | " | " | N(HpaI$^-$-SmaI$^-$-BamHI-SmaI-BamHI)Z (+1) | " | |
| pDH428 | P$_L$' | " | λrepressor[3,4] | N(HpaI$^-$-SmaI$^-$-BamHI)Z (0) | " | |
| pDH438 | " | " | " | N(HpaI$^-$-SmaI$^-$-BamHI-SmaI-BamHI)Z (+1) | " | |
| pDH500 series | P$_L$ | None | " | (HindIII) | amp$^R$ tet$^R$ | |
| pDH600 series | None | lacZ-λcro | N.A. | cro(BglII-SmaI-BamHI)I-Z (0) | amp$^R$ | |
| pDH700 series | P$_L$ | " | λrepressor[3,4] | cro(BglII-SmaI-BamHI)I-Z (0) | " | |
| pDH800 series | " | " | cI857 λrepressor[5] | cro(BglII-SmaI-BamHI)I-Z (0) | " | |

[1] CAP site deleted, plus UV5 promoter mutation.
[2] L8 CAP site mutation, plus UV5 promoter mutation.
[3] cI$^+$ or cI857 temperature-sensitive mutation (30° C., active; 42° C., inactive).
[4] Supplied by prophage in host cell.
[5] Carried on plasmid.

The control elements that have been varied include: (a) promoters that ensure efficient transcription of the DNA into mRNA; (b) ribosome binding sites that ensure efficient translation of the mRNA into protein; (c) repressor and operator regions that allow regulation of gene expression; and (d) replication of the plasmid to high copy number.

For instance, the promoters used to construct the plasmids of this invention include, but are not limited to, Plac, from the lac operon of the E. coli chromosome, P$_R$, the rightward promoter of bacteriophage λ, and P$_L$, the leftward promoter of λ. New promoters may be found by applying the method of Casadaban and Cohen [J. Mol. Biol. 138: 179-207 (1980)]. Plasmids pJS413, pHK413, pHK412, pHK414, pHK410, and pHK411 have the Plac promoter containing the UV5 promoter mutation and a deletion of the CAP binding site. Plasmids pMG101 and pJS400 have the Plac promoter containing the UV5 and L8 mutations affecting the promoter and CAP binding site, respectively. The $P_R$ promoter, thought to be a stronger promoter than Plac, is contained within pDN455 and its derivatives. Plasmids pDH55, pDN55, pDN72, pDH428, pDH438 and the pDH500 and pDH700 series have the $P_L$ promoter (also thought to be a stronger promoter than Plac). Plasmids pDH26 and pDH36 contain both the $P_R$ and $P_L$ promoters, but oriented in opposite directions. The pDH800 series also has both $P_L$ and $P_R$ promoters but they are oriented in the same direction.

Translation initiation signals present in the plasmids of this invention were derived from the lacZ gene of the E. coli chromosome, the cro gene of λ and the N gene of λ, though other SD/AUG sequences can be used. Plasmids pMG101 and pJS400 contain the ribosome binding site of lacZ. Plasmids pJS413, pHK413, pHK412, pHK414, pHK410, pHK411 and the pDH700 and pDH800 series have a fused (or hybrid) ribosome binding site containing the SD sequences of both lacZ and λcro (or portions thereof). Some of the croΔ derivatives of pJS413 have deletions covering the AUG codon of cro while others are deleted for both AUG$^{cro}$ and portions of the cro SD sequence. Plasmids pDH26, pDH36, pDH72, pDH428 and pDH438 contain the λN SD sequence.

The gene transcription regulation systems incorporated into the plasmids of this invention are negative control systems derived from the lac operon of E. coli and from bacteriophage λ. Different regulatory mechanisms, including positive control systems, could be substituted into the plasmids of this invention to provide other means of controlling gene transcription (and ensuing expression) experimentally. Plasmids pJS413, pHK413, pHK412, pHK410, pHK411, pMG101 and pJS400 contain the operator region from the lac operon (Olac) to which lac repressor protein (the product of the lacI gene) binds reversibly, blocking transcription when bound. If any of these lac regulated plasmids are transformed into lacI⁻ strains of E. coli or other microorganisms, the plasmid genes are not repressed and are therefore transcribed. On the other hand, if any of these plasmids are transformed into lacI+ or lacIQ (a mutation causing a ten-fold over-production of lac repressor) strains of E. coli or other microorganisms, the transcription of plasmid genes is repressed. To depress the system, the gratuitous inducer IPTG can be added to the medium of the host microrganism. Alternatively, the host microorganism can be grown in a medium containing the natural inducer, lactose. Either inducer interacts with the repressor in such a way as to prevent the repressor protein from binding or continuing to bind to the operator which permits the initiation of transcription.

Plasmids pDH55, pDN55, pDH26, pDH36, pDH72, pDH428, pDH438, and the pDH700 series contain $O_L$, the leftward operator region from bacteriophage λ. Plasmid pDN455 contains $O_R$ the rightward operator region from λ. Three of the plasmids, pDN455, pDH26, pDH36 and plasmids series carry the λcI gene coding for λ repressor protein which interacts reversibly with both the $O_R$ and $O_L$ operator regions to block transcription when bound. The particular cI gene incorporated into these plasmids bears the cI857 mutation which produces a temperature-sensitive repressor protein. When these plasmids are transformed into hosts grown at temperatures at which the repressor is active (about 30°-33° C.), transcription of plasmid genes is blocked. When the host is shifted to a temperature at which repressor protein is inactive (about 39°-42° C.), plasmid genes are transcribed.

Plasmids pDH55, pDN55, pDH72, pDH428, pDH438 and the pDH500 and pDH700 series do not contain a cI gene coding for the λ repressor. In order to control transcription on these plasmids, the host microorganism must carry a λ repressor-producing prophage. If the prophage produces the cI857 temperature-sensitive repressor, temperature manipulation can be used to control gene transcription. If the prophage produces the wild type cI repressor, another means of transcription induction is required, e.g., UV light, mitomycin C or the tif allele of recA which activates a protease specific for λrepressor.

In addition to promoters, operators, repressor genes and SD/AUG sequences, a control element responsible for increased plasmid copy number has been incorporated into some of the plasmids of this invention. For instance, plasmid pSH113 carries the OP1Δ6 colE1 ori mutation which causes over-replication of the plasmid in the host microorganism, thereby potentially enhancing over-expression of cloned segments.

The plasmids of this invention were designed and constructed to provide unique restriction sites for the cloning of genes or gene segments into the vectors. [The region of a plasmid where unique restriction sites are located is referred to as the cloning segment in this specification.] Unique sites ensure that nucleic acid sequences of interest will be inserted at the precise point required to: (a) bring the insert under the control of elements upstream from it and/or (b) fuse the insert with regions downstream that facilitate expression detection. The restriction sites within the cloning segments of each of the plasmids described in Section 5 are shown in Table I. It is within the scope of this invention that cloning segments containing other unique restriction sites can be inserted into the plasmids of this invention.

The number of unique restriction sites in the plasmids was varied by the insertion of linkers (nucleic acid sequences bearing unique recognition sites for one or more restriction endonucleases) into already existing restriction sites. By way of illustration, pHK413 was made from pJS413 by replacing the BglII-SmaI site with a synthetic oligonucleotide linker carrying the HindIII site between the BglII and SmaI sites. The incorporation of several unique restriction sites into a plasmid imparts greater cloning flexibility, i.e., the range of gene segments that can be inserted into the plasmid is increased.

In addition to providing new unique restriction sites, synthetic oligonucleotide linkers were used to change the reading frame of sequences downstream from the linker with respect to (a) the start codon upstream from the linker, and (b) the coding sequence of lacZ downstream of the linker. By inserting linkers with the appropriate number of base pairs, the translational phase of any given plasmid can be readjusted to either of the other two possible phases. The phase readjustment can be made with respect to either the upstream or downstream regions, or both.

The plasmids of this invention were constructed to include genetic markers that facilitate selection of transformants and detection of gene expression. Antibiotic resistance was used as a marker to select for successful transformation of plasmid vectors into *E. coli* or other host microorganisms. Genes imparting resistance to antibiotics including, but not limited to, ampicillin or tetracycline are carried on the plasmids. Chloramphenicol may also be used. When microbial strains sensitive to the marker antibiotic are used as hosts for the plasmids, transformants can be detected as resistant colonies on plates containing the given antibiotic. Non-transformed hosts are effectively eliminated in this selection.

A key feature of the plasmids of this invention (with the exception of pDH55 and pDN55) is the inclusion of a portion (a carboxy-terminal fragment) of the lacZ gene out of phase with respect to the translation start codon upstream. When a gene or gene segment which properly readjusts the phase of the start codon with respect to the Z gene is inserted into a cloning site, a fusion protein is made that exhibits $\beta$-galactosidase activity. Expression of $\beta$-galactosidase activity and, therefore, of the cloned segment as part of the fusion protein, are easily detected by growing the transformed host on plates containing a substrate which, when enzymatically hydrolyzed, liberates a colorimetric product. These clones can be further manipulated to create a plasmid yielding the unfused (reconstituted) protein product of interest [Guarante et al., Cell 20: 543–553 (1980)].

This invention also provides methods for mutagenesis and selection of clones that are strongly over-producing fusion-protein. An amber or other nonsense codon is inserted into a plasmid in phase with the translation initiation codon and with the coding sequence of lacZ. The site of insertion is at the junction between the cloned segment and lacZ so as to largely block $\beta$-galactosidase synthesis (Lac$^-$ phenotype) when the plasmid is transformed into a nonsuppressing lac$\Delta$ host cell. Since the amber codon is subject to a low level of "read-through" translation, a low level of $\beta$-galactosidase is nonetheless made, and any mutation that would increase the level of initiation of transcription or translation should increase the absolute level of read-through $\beta$-galactosidase synthesis. Thus, following mutagenesis of the plasmid, individual mutants with increased efficiency of transcription and/or translation, or mutants producing a protein of greater stability than wild type, can be selected as Lac$^+$ transformants of lac$\Delta$ host cells. Additionally, plasmids bearing newly generated DNA fusions between promotor (not Plac) and SD-ATG segments that allow high-efficiency initiation of translation (into an adjacent lacZ coding segment) can also be identified by the Lac$^+$ phenotype of transformed lac$\Delta$ host cells. Under repressed conditions, when only a low (basal) level of mRNA produced from the plasmid is present, the only plasmid transcripts that could confer the Lac$^+$ phenotype would be those that were translated efficiently.

This invention further contemplates the use of the plasmids described herein in the processes of direct cloning and "shot-gun" cloning. Direct cloning procedures are aimed at fusing specific gene segments in phase with the start codon upstream of the cloning site or with the expression detection marker (e.g., the Z gene) downstream of the site, or both.

In the "shot-gun" cloning process, the desired DNA segment is first cloned in a replication vector, e.g., pBR322 or its derivatives, so as to generate multiple copies of the desired DNA segment. The clone is then purified and the DNA segment excised and treated with a nuclease, such as DNaseI, to generate multiple fragments ranging in size between fifty and several thousand nucleotides in length. These fragments are separated on a gel and the desired size classes of fragments are cut out of and eluted from the gel. These fragments are then recombined (spliced) into the expression vector(s) of this invention and used to transform appropriate host cells. The transformants are then assayed for expression of either the entire gene or fraction thereof (e.g., an antigenic or active site or determinant).

It is apparent that many modifications and variations of this invention may be made without departing from the spirit and scope thereof. The specific embodiments described are given by way of example only and the invention is limited only by the terms of the appended claims.

BRIEF DESCRIPTION OF THE FIGURES

To more fully comprehend the invention, reference should be made to the accompanying figures (not drawn to scale), in which

FIG. 28 depicts the isolation of recombinant plasmid pDN55 and the steps taken to convert pDH55 into pDN55;

DETAILED DESCRIPTION OF THE INVENTION

Independent of the mechanism by which the present invention may be explained, one of ordinary skill in the art may successfully make and use the invention as herein described.

5.1. pJS413

5.1.1. Isolation of Plasmid pJS413

Figure 1A:
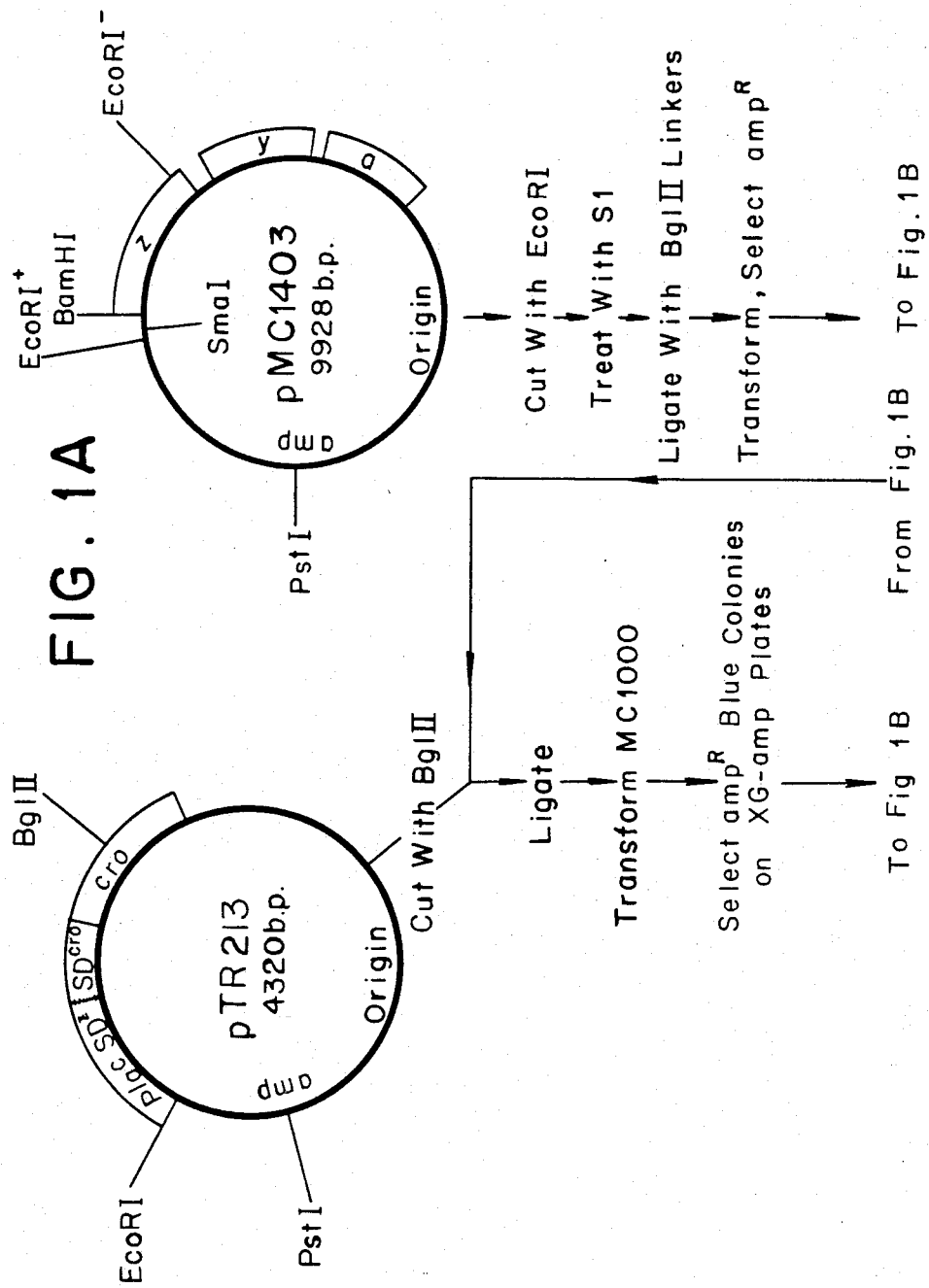
FIG. 1 depicts the construction of recombinant plasmid pJS213-1403, an intermediate in the construction of recombinant plasmid pJS413.
Figure 1B:
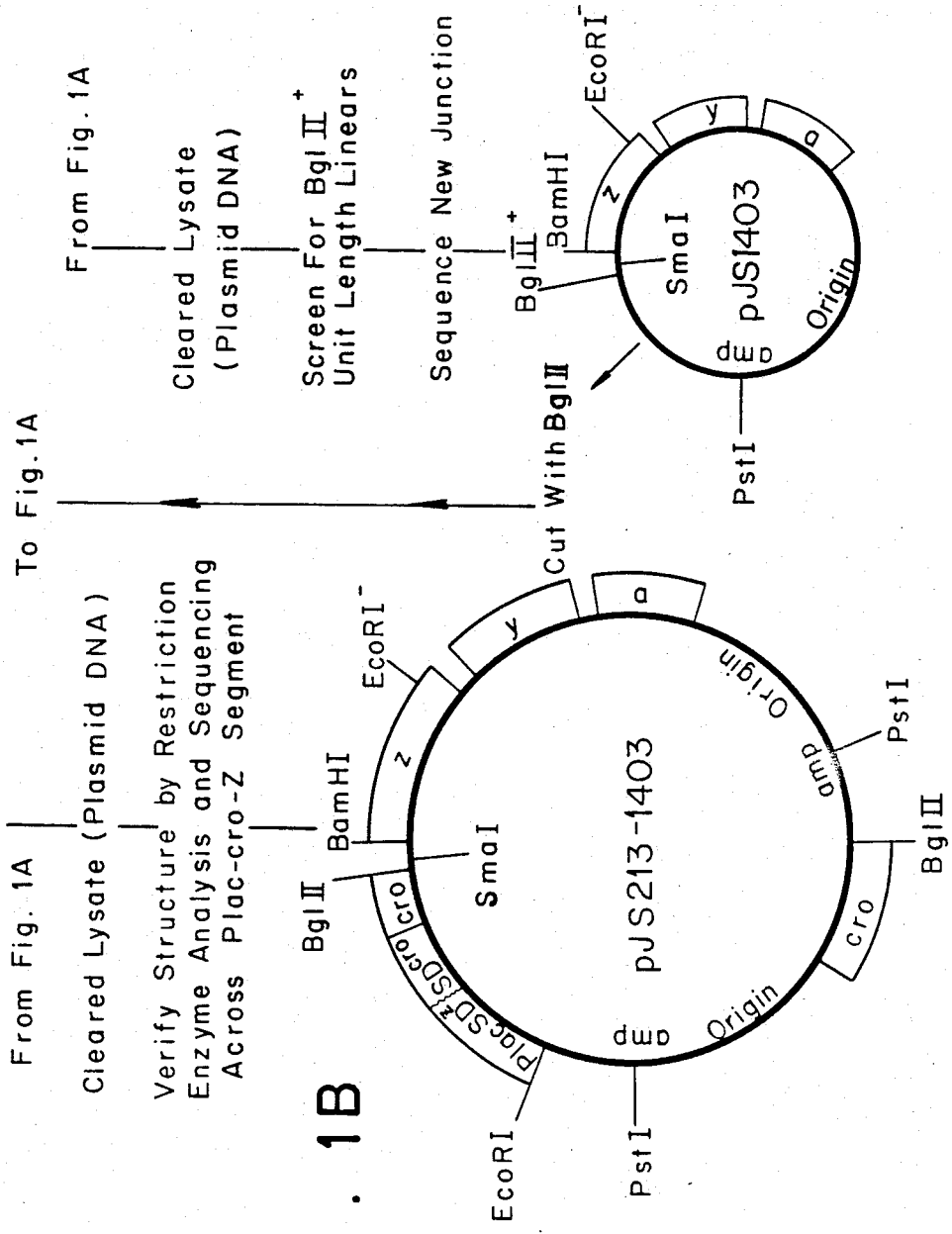
Figure 2A:
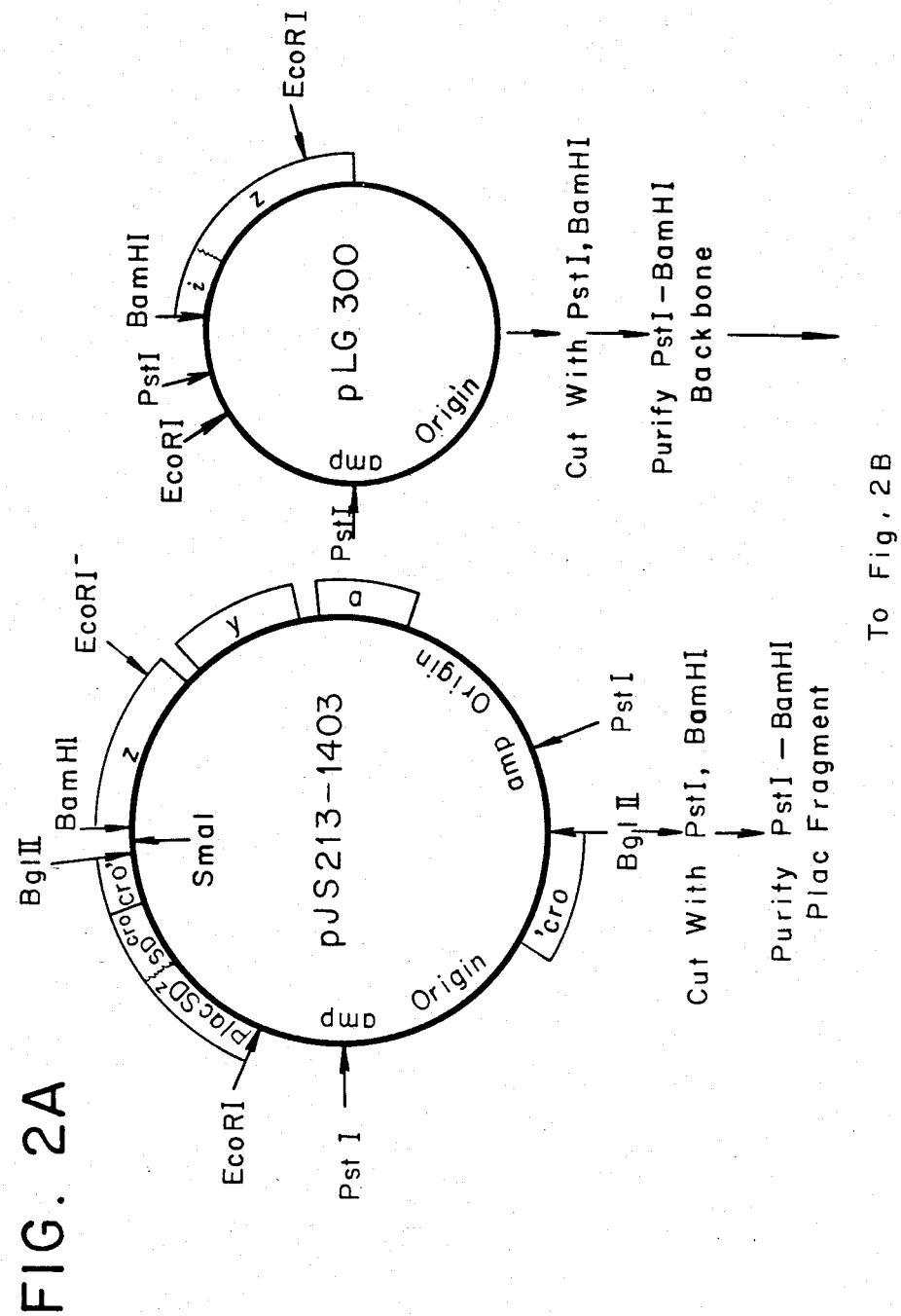
FIG. 2 depicts the steps taken to treat and recombine portions of recombinant plasmids pJS213-1403 and pLG300 in the construction and isolation of recombinant plasmid pJS413.
Figure 2B:
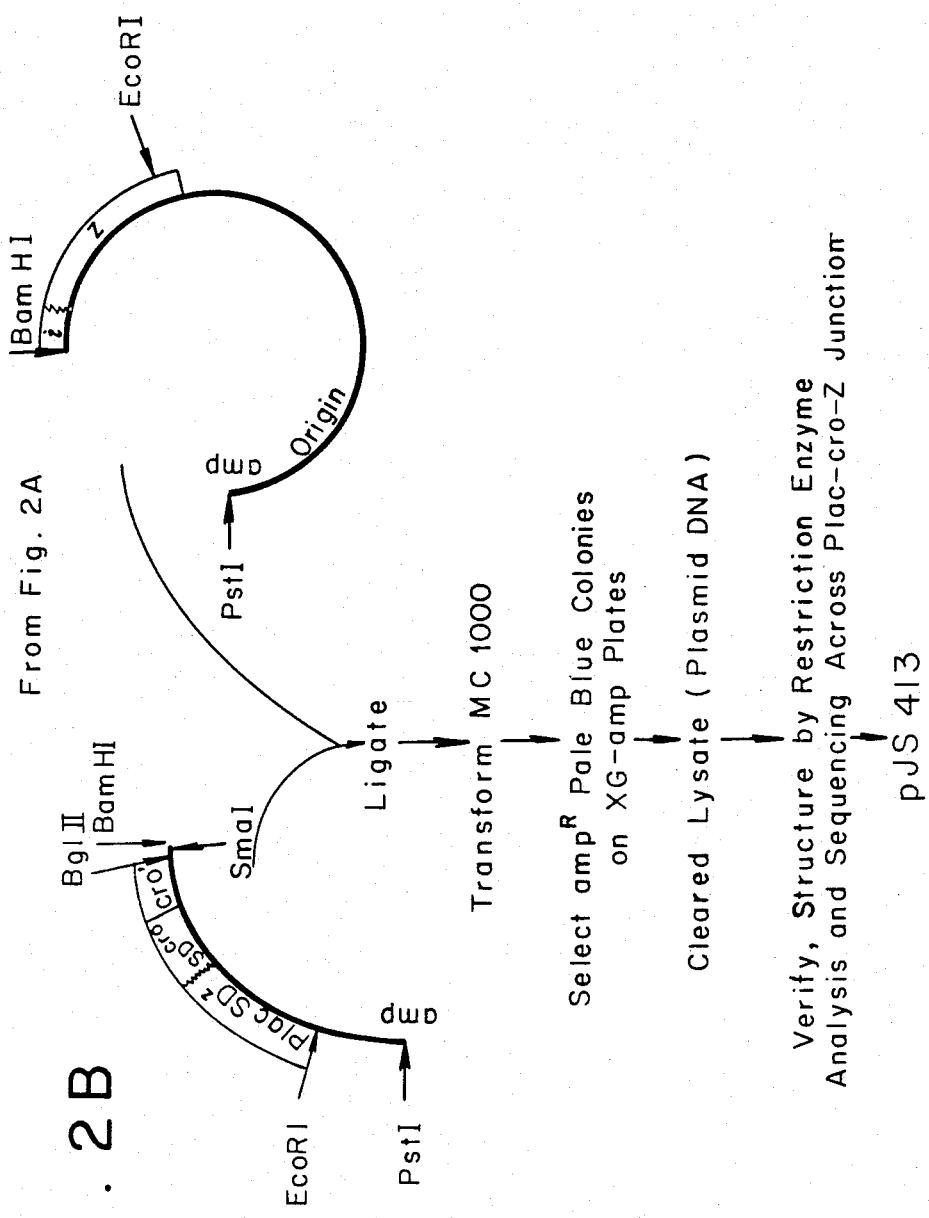
Figure 3:
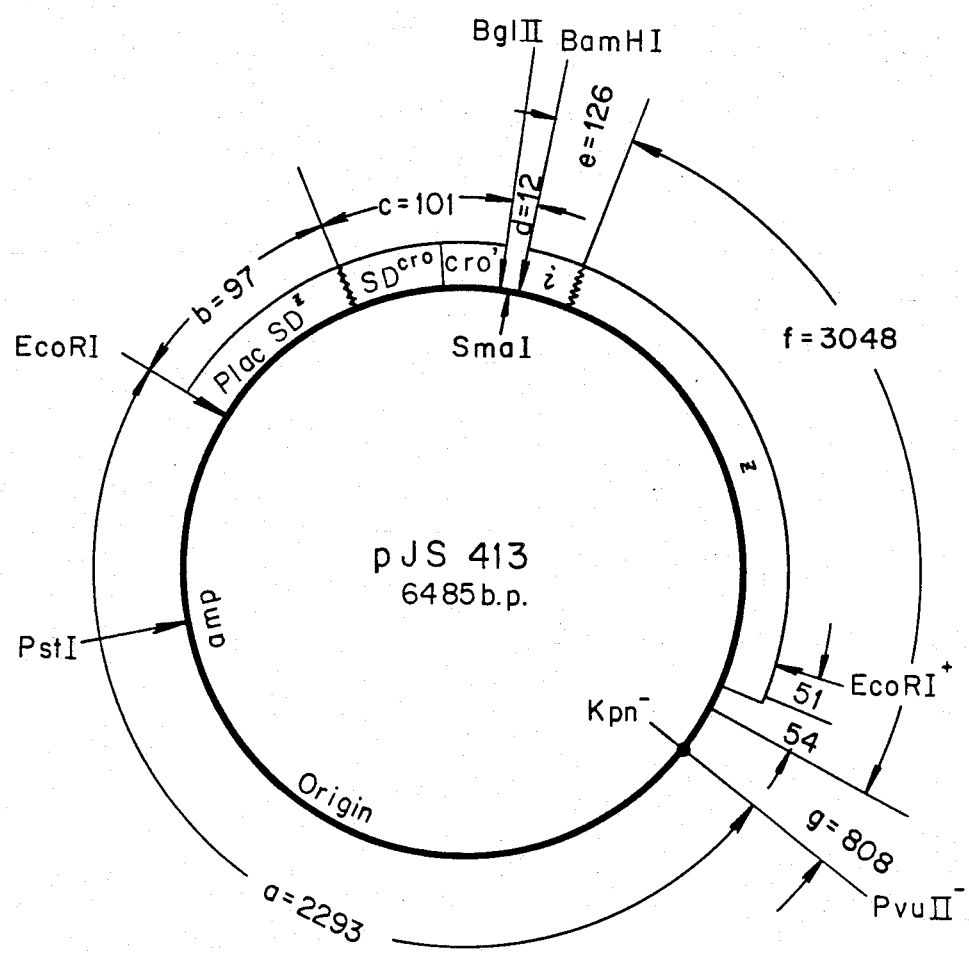
FIG. 3 is a schematic diagram of recombinant plasmid pJS413. For an explanation of the lettered segments, see Section 5.1.2.
Figure 34:
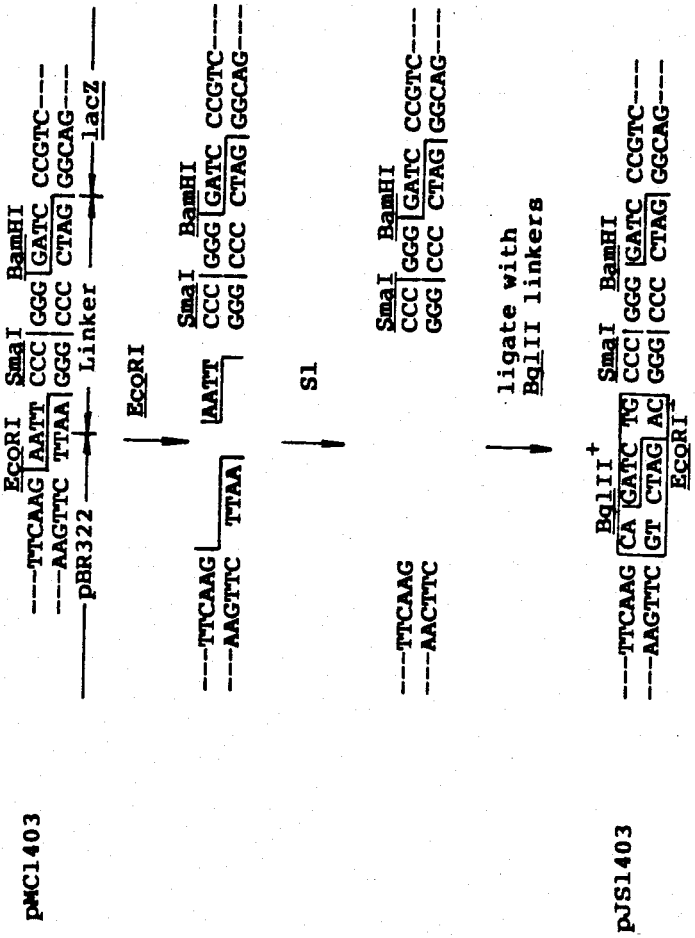
FIG. 34 is a flow chart showing the steps in the conversion of plasmid pMC1403 to plasmid PjS1403.

Plasmid pJS413 was constructed in several steps (see FIGS. 1, 2 and 3). First, the EcoRI site of pMC1403, a plasmid containing 9,926 base pairs (b.p.) described by Casadaban et al. [J. Bacteriol. 143: 971–980 (1980)], was converted to a BglII site by cutting with EcoRI, treating with S1 nuclease, and then religating in the presence of a synthetic oligonuclotide (octamer) carrying a restriction site for BglII. This conversion is shown in FIG. 34.

The resulting plasmid, pJS1403, together with plasmid pTR213, a plasmid with approximately 4,320 base pairs described by Roberts et al. [Proc. Natl. Acad. Sci., U.S.A. 76: 760–764 (1979)] were opened with BglII, mixed and religated to yield the chimeric plasmid, pJS213-1403. Plasmid pJS213-1403 recombines with itself to yield monomers of two types (not shown), one with the Plac-cro-lacZ, Y, A and amp segment; the other with the carboxy two-thirds of cro and the amp gene. Each has an origin (ori) and therefore is able to replicate autonomously. The Plac bearing PstI-BamHI segment (958 b.p.) was isolated from pJS213-1403 and ligated into the PstI-BamHI backbone (5,527 b.p.) of pLG300 [Guarente et al., Cell 20: 543–553 (1980)] to yield pJS413 (see FIGS. 2 and 3).

Plasmid pJS413 was transformed into *E. coli* MC1000 [Casadaban and Cohen, J. Mol. Biol. 138: 179–207 (1980)] and colonies that were ampicillin-resistant and pale blue on XG plates were selected. [XG plates contain the dye X-gal (5-bromo-4-chloro-3-indolyl-β-galactoside) which is broken down by β-galactosidase, the product of the lacZ gene, to yield a blue color.] Theoretically, lacΔ cells bearing pJS413 should be white on XG plates since the cro and lacZ coding sequences are fused in such a way that they are out of phase with respect to each other. However, the colonies are pale blue on XG presumably because there is a low level of "re-start" translation in phase with the Z gene, or some low level "phase-readjusted" translation into the Z gene from cro, either of which would lead to some β-galactosidase production.

Figure 5:
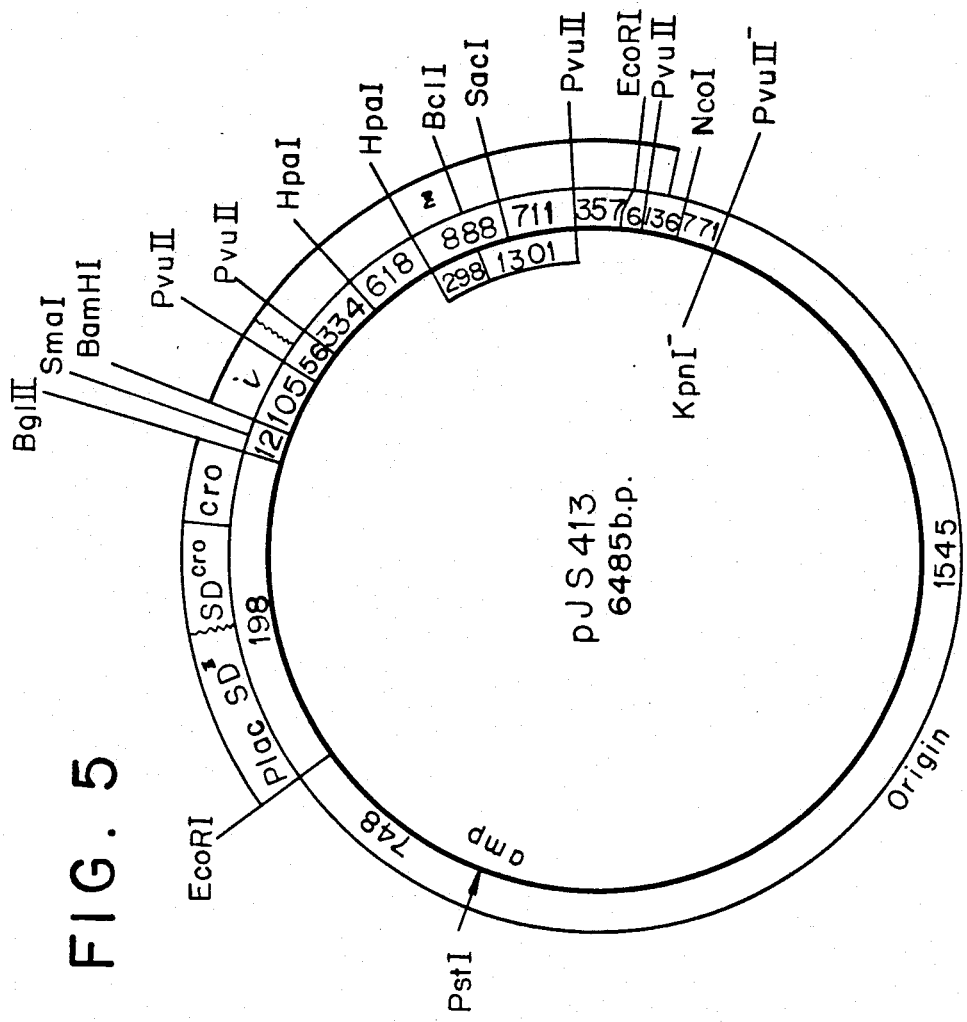
FIG. 5 is a partial restriction endonuclease cleavage map of recombinant plasmid pJS413.
Figure 6:
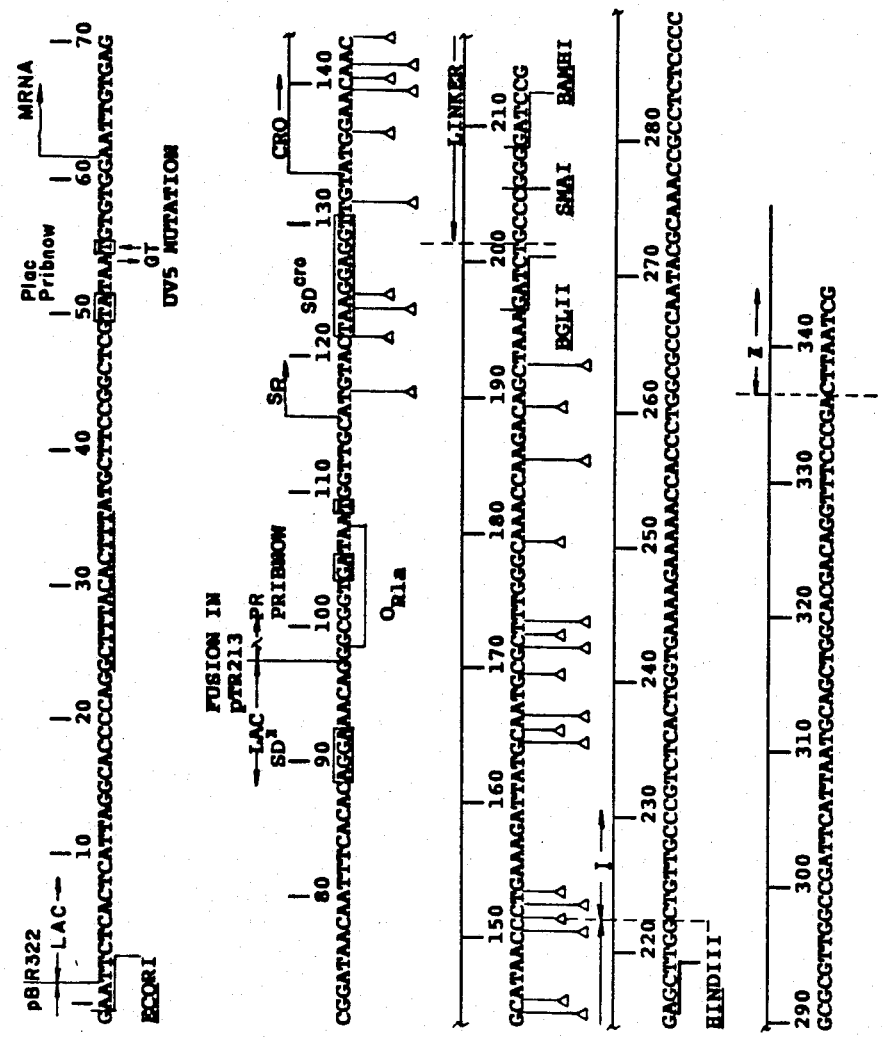
FIG. 6 represents the DNA sequence of the Plac-SD$^Z$-SD$^{cro}$-cro-linker-I-Z segment of recombinant plasmid pJS413. The cro deletion endpoints are indicated by the symbol ($\Delta$) (See Section 5.2.4.).

Plasmid pJS413 DNA was isolated from cleared lysates of *E. coli* MC1000 and the plasmid structure was verified by restriction enzyme analysis and DNA sequence analysis of the Plac-cro-Z segment (see FIGS. 5 and 6).

5.1.2. Structure and Description of pJS413

A schematic diagram of pJS413 (6,485 b.p.) is shown in FIG. 3. Sub-segment a (2,293 b.p.) is the EcoRI-PvuII fragment from pBR322 [Bolivar et al., Gene 2: 95–113 (1977)] and contains the β-lactamase gene (amp) and the colE1 origin of replication (ori). Sub-segment b (97 b.p.) is the AluI fragment from the lac operon of *E. coli* which bears the lac promoter-operator region and the lacZ ribosome binding site known as the "SD" sequence [Shine and Dalgarno, Proc. Natl. Acad. Sci., U.S.A. 71: 1342–1346 (1974); Nature 254: 34–38 (1975)

and Backman and Ptashne, Cell 13: 65–71 (1978)]. Sub-segment c (101 b.p.) is from bacteriophage λ and includes part of the rightward promoter-operator region ($P_R$-$O_R$), which is non-functional in pJS413, the SD sequence of the λ cro gene, and the first 68 b.p. of the cro coding sequence. Sub-segment d (12 b.p.) is a synthetic DNA adapter bearing the SmaI restriction site bounded by BglII and BamHI ends. Sub-segment e (126 b.p.) includes 114 b.p. (#980 to #1093) of the lacI gene [see Miller IN: The Operon, J. H. Miller and W. S. Reznikoff, eds., Cold Spring Harbor Laboratory, Cold Spring Harbor, N.Y., pp. 31–88 (1980)] preceded by 12 b.p. of synthetic DNA [Guarente et al., Cell 20: 543–553 (1980)]. Sub-segment f (3,048 b.p.) is entirely from the lac operon. It includes all but the first 69 b.p. of the lacZ gene, the SD sequence of the lacY gene (which codes for lac permease), and all nucleotides up to but not including the AUG start codon of the latter. Sub-segment g (808 b.p.) is from the lom gene of bacteriophage λ just to the right of the KpnI site on the conventional λ map.

Figure 4:
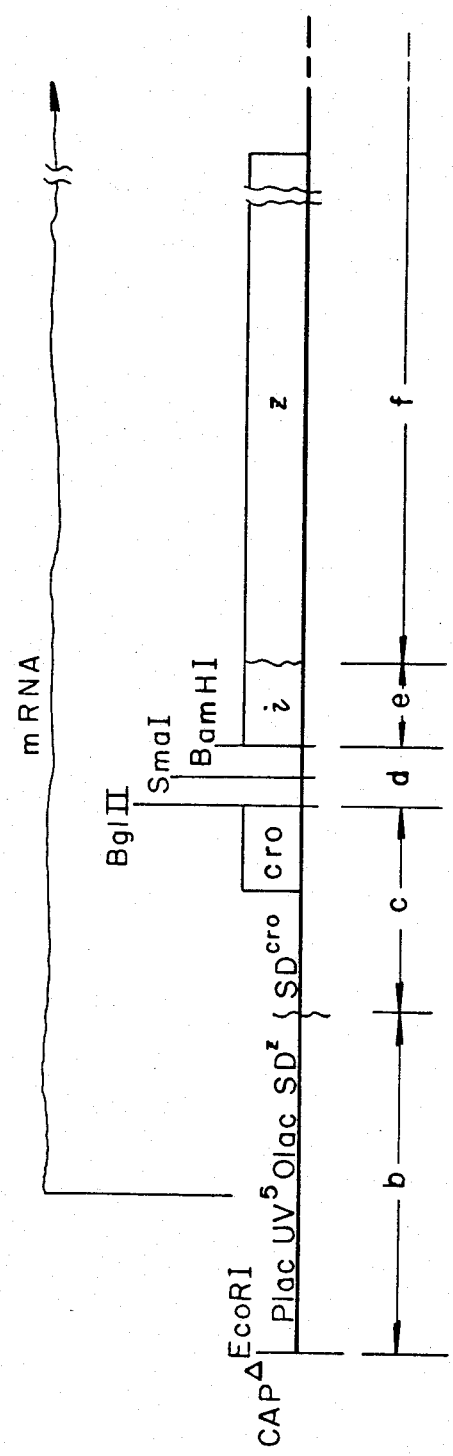
FIG. 4 is a schematic diagram of the Plac-cro-I-Z region of recombinant plasmid pJS413. For an explanation of the lettered segments, see Section 5.1.2.

The contiguous sub-segments b, c, d, e, and f in pJS413 (see FIGS. 3 and 4) make up a hybrid gene, Plac-cro-I-Z, in which the I-Z portion is out of phase with respect to cro. Therefore, the plasmid theoretically does not direct production of the full-length cro-I-Z fusion polypeptide.

The lac promoter, Plac, on sub-segment b, bears the UV5 mutation that allows E. coli RNA polymerase to initiate transcription of downstream regions, even though the segment lacks the CAP (catabolite activator protein) binding site. This site normally resides just upstream of Plac and binds CAP to promote efficient transcription initation from Plac in the wild-type operon. Olac, the operator region, on sub-segment b, binds lac repressor and allows negative regulation of transcription from the plasmid. The lacZ ribosome binding site, $SD^Z$, on the mRNA from sub-segment b, is presumably too far from the AUG in this construction to be functional.

The cro segment, sub-segment c, was chosen for this construction primarily because the ribosome binding region was presumed to be very strong based on the extent of complementarity between the 3' end of the 16S ribosomal RNA and the $SD^{cro}$ region theorized by Shine and Dalgarno [supra, (1974 and 1975)] to have a significant role in the initiation of translation. Furthermore, Roberts et al., supra, (1979)] had fused the UV5 lac promoter to the cro segment in such a way as to achieve high-level synthesis of Cro protein. Thus, the particular fusion of sub-segment b to sub-segment c in pTR213 (See FIGS. 1 and 3), the best Cro over-producing plasmid, was chosen for the pJS413 construction. The cro segment bears the natural SD-to-AUG region along with the first twenty-two and two thirds (22 ⅔) codons of cro. The latter preserves any possible contribution to over-production that the cro coding region itself may impart.

The sequence of the linker, sub-segment d, inserted after cro, was designed to provide unique sites (BglII, SmaI and BamHI) for cloning segments of choice between cro and I-Z, and to place the natural reading frame of I-Z in a different phase with respect to that of cro in the plasmid without a cloned segment (see below Section 5.1.3.).

The I-Z fusion, sub-segment e fused to sub-segment f, was included to monitor expression of cloned segments. Evidence indicates that the fusion of polypeptides to the amino-terminal end of the lacZ protein usually does not block its β-galactosidase activity. The first such fusion type was a lacI-Z fusion. Guarente et al. [supra, (1980)] prepared pLG300 bearing this fusion junction by removing all but 114 b.p. (38 amino acids) of the I portion (by partial PvuII digestion) and by adding 12 b.p. of synthetic DNA, all performed in a pBR322-like plasmid background. This truncated I-Z fusion was chosen for pJS413 to permit fusion of polypeptides directly to the amino-terminal end of the I segment (42 amino acids long) which itself is fused to the Z segment in a way already known not to interfere with β-galactosidase activity. Once satisfactory levels of expression of the β-galactosidase fusion product are achieved, the I-Z portion can be removed from the plasmid, if desired, and replaced by the missing carboxy-terminal portion of the cloned segment, if required, to reconstitute the intact coding sequence for the protein (see Guarente et al. [supra, (1980)]).

Because the I-Z portion of the cro-I-Z hybrid gene in pJS413 is out of phase with respect to the cro coding region, translation from the AUG of cro should be interrupted by a UGA nonsense codon (within I) after only 36 amino acids (22 from cro, 8 from the synthetic adapter and synthetic DNA from pLG300, and 6, out of phase, from the first part of the I segment) are synthesized. Any continued translation due to possible inefficiency of chain termination at the UGA codon should proceed, still out of phase, for only another 21 amino acids before reaching a UAA terminating codon. If one additional base (or 3n+1 bases) is added between the cro and the I-Z segment, the translational coding phase of I-Z becomes adjusted to that of cro, and the cro-I-Z fusion protein is synthesized normally and exhibits β-galactosidase activity.

Lac+ cells produce β-galactosidase and form blue colonies on XG plates containing the dye X-gal or red colonies on MacConkey-lactose (Mac-lac) plates, whereas Lac- cells, e.g., cells deleted for the entire lac operon, that do not produce β-galactosidase, form white colonies on both plate types. Lac- cells carrying a plasmid that produces the cro-I-Z fusion protein, however, exhibit the Lac+ phenotype. Thus, theoretically, any event that adjusts the reading phase of I-Z to that of cro in pJS413 leads to production of a β-galactosidase fusion polypeptide which is detectable in Lac- cells by the color reaction.

5.1.3. Use of pJS413 as a Cloning Vehicle

Any segment of DNA, X, that is 3n+1 base pairs long can be inserted between the cro and I-Z segments at the BglII, SmaI or BamHI sites to readjust the reading frame of I-Z to that of cro. A quadruple fusion protein, cro-X-I-Z, results unless the insert contains an in-phase nonsense codon. A fusion without a nonsense codon exhibits β-galactosidase activity, and indicates successful transcription and translation of the inserted segment. Thus, the pJS413 plasmid not only allows cloning and expression of gene segments, but provides a system for detection that both events occurred. That is, if the inserted gene segment is 3n or 3n+2 base pairs long, or if no segment is inserted at all, β-galactosidase will not be produced and the cells remain white on Mac-lac plates. (Theoretically, Δlac cells bearing pJS413 should be white on both XG and Mac-lac plates. However, such plasmid-bearing cells appear pale blue on XG, presumably the result of a "re-start" or a "phase readjustment" phenomenon that allows some low-level translation of β-galactosidase, as discussed earlier in Section 5.1.1. The color reaction on Mac-lac is much less sensitive than on XG and therefore is quite adequate for this cloning system.) The special case of segments 3n or 3n+2 base pairs long in which the coding sequence of the insert is fused in phase to the I-Z segment is sometimes desirable, however. (See below.)

Plasmid pJS413 can be used as an expression vehicle in both shot-gun cloning and in direct cloning experiments. The shot-gun expression procedure simply involves selection of 3n+1 base pair segments of continuous coding sequence from a gene, e.g., a viral capsid gene, that are in phase with the reading frame of cro and I-Z. Such colonies have the Lac+ phenotype and appear red on Mac-lac plates and can be screened with the appropriate (viral) antiserum to identify clones expressing particular antigenic sites.

The direct cloning procedures attempt to fuse specific gene segments in phase with the I-Z moiety, or to the cro segment, or both. If the segment (3n+1 b.p.) is a continuous coding region and is in phase with cro and with I-Z, then a cro-X-I-Z polypeptide will be made and will confer the Lac+ *phenotype upon Lac−* cells, as discussed in Section 5.1.2. If the above segment is in phase with I-Z, but is 3n or 3n+2 b.p., or contains an intron, or intergenic region, then the Lac− host cells will retain the Lac− phenotype. Such plasmid constructions may be manipulated to adjust the cro and segment X reading phases to each other, or to remove the untranslated regions, to allow cro-X-I-Z fusion protein to be synthesized. Success in these manipulations may be monitored by measuring β-galactosidase activity, e.g., red colonies on Mac-lac plates. Finally, if a continuous coding sequence were fused in phase directly to cro without regard to I-Z phasing, then a cro-X fusion results and can be monitored using immunological techniques.

Double-stranded DNA fragments to be cloned can be generated by a variety of methods including but not limited to (a) the use of restriction endonucleases that produce 5' protruding single-stranded ends of sequence 5'-GATC-3', e.g., BglII, BamHI, BclI, Sau3AI, etc. Such fragments can be ligated into the BglII site, the BamHI site or the BglII-BamHI site; (b) the use of restriction endonucleases that produce blunt ends upon cleavage, e.g., HpaI, RsaI, AluI, HaeIII, etc. Such fragments can be ligated into the SmaI site (which also produces blunt ends upon cleavage with SmaI); (c) the use of restriction endonucleases that produce any 5' protruding end that can be rendered blunt (i) by filling in with DNA polymerase, or (ii) by S1 nuclease digestion for insertion into the SmaI site; (d) the use of restriction endonucleases that produce 3' protruding ends that can be rendered blunt by S1 nuclease digestion for insertion into the SmaI site; (e) the use of restriction endonuclease (of any kind) digestion followed by Bal31 digestion to produce blunt ends for insertion into the SmaI site; (f) DNaseI digestion, or controlled physical shearing of the DNA, followed by S1 and DNA polymerase treatment to produce blunt ends for insertion into the SmaI site; (g) the use of any combination of the above for insertion into the appropriately cut plasmid backbone. It should be noted that any blunt end can be converted to a BglII end or a BamHI end for insertion into either the BglII site, the BamHI site or the BglII-BamHI site, simply by attaching BglII or BamHI linkers.

A special attribute of cloning into the SmaI site of pJS413 is that the cloned segment can be easily recovered for purification for further analysis or for subsequent sub-cloning of the fragment by cutting the plasmid with BglII and BamHI.

If the expression of a cloned segment either kills the host cell or provides the cell with a selective disadvantage, it is necessary to perform all cloning with pJS413 or its derivatives (see section 5.2) under repressed conditions. The normal lacI gene of E. coli produces about 10 copies of lac repressor per cell, while the lacI$^Q$ mutant (up promoter) produces at least 10-fold more. Thus, lacI$^Q$ is the more desirable of the two as a source of repressor. The lacI$^Q$ gene resides on an F' episome permitting easy transfer into any desirable strain. Lac repressor can be inactivated in the cell by either supplying lactose to the medium or by adding the inducer, isopropyl-β-D-thiogalactoside (IPTG). Thus, the plasmid bearing cells can be derepressed experimentally to allow controlled synthesis of the cloned protein.

5.2. Derivatives of pJS413

5.2.1. Changes in the Linker

The linker between the unique BglII and BamHI sites in pJS413 is:

and can be changed by the addition of or by the substitution of any synthetic oligonucleotide desired. For example, oligonucleotide linkers or adapters can be inserted into the BglII site, the SmaI site, the BamHI site, or any pairwise combination to add new restriction endonuclease sites or to change the reading frame of I-Z with respect to cro, or both. For example, pHK413 is a derivative of pJS413 made by inserting into the BglII-SmaI site the BglII-SmaI synthetic oligonucleotide adapter also carrying the HindIII site:

The resulting plasmid has the following sequence across the linker region:

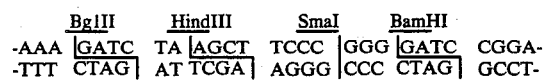

The BglII and SmaI sites have been regenerated, a unique HindIII site has been inserted and the BamHI site has been retained. Now all four sites or any pairwise combination of these can be used for cloning as described above.

Since pHK413 has a net insertion of 5 (14 minus 9) nucleotides relative to pJS413 (+2 phase), it is in the +1 phase, i.e., has only one extra base. Thus, the plasmid still produces no cro-I-Z fusion protein.

In order to adjust any linker between cro and I-Z in pHK413 to the other two reading frames with respect to that of I-Z, each of the following two adapters was inserted into the HindIII-BamHI site of pHK413:

The resulting plasmids have the following sequence between the BglII site and the previously existing BamHI site (now BamHI⁻):

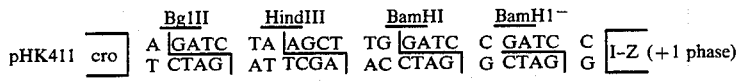

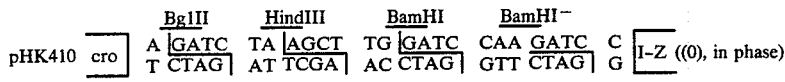

As in pJS413, essentially any synthetic oligonucleotide linker or adapter may be inserted between BglII and BamHI in iether of these two plasmids to yield cloning sites in all reading frames with respect to that of I-Z. For use in the present invention, the BglII-HindIII-SmaI-BamHi linker from pHK413 was inserted between the BglII and BamHI sites of pHK411 and pHK410 to yield pHK412 and pHK414, respectively:

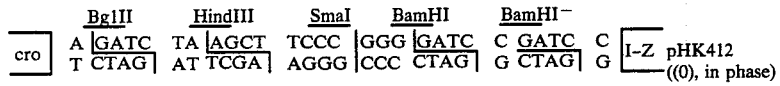

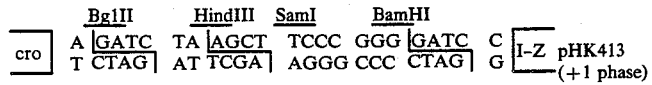

Similarly, to adjust any linker between cro and I-Z to the other two reading frames with respect to that of cro, the following two adapters:

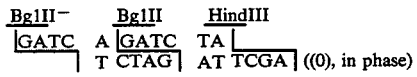

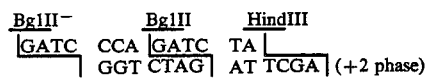

can be inserted into the BglII-HindIII site of pHK413. The resulting plasmids, pHK420 and pHK422, would have the following sequence between the previously existing BglII site (now BglII⁻) and the HindIII site:

5.2.2. Elimination of the EcoRI SITE IN lacZ

Plasmid pJS413 has two EcoRI sites (see FIG. 5), one in lacZ and the other just upstream of Plac. To eliminate the EcoRI site in lacZ, we excised the NcoI-SacI 1210 b.p. fragment carrying the EcoRI⁺ site from pDN413 (an in-phase version of pJS413) and replaced it with the otherwise identical NcoI-SacI fragment from pRB205 carrying an EcoRI⁻ mutation [K. Bertrand, unpublished; Munson and Reznikoff, Gene (in press, 1982)]. The reconstituted lacZ gene produces active β-galactosidase. This plasmid (or any other in-phase or out-of-phase derivative thereof) now has the unique EcoRI site upstream of Plac, eliminating the need for partial EcoRI digestion of the plasmid when DNA manipulations involving that EcoRI site are to be performed.

5.2.3. Substitution of the $tet^R$ Marker for $amp^R$

Because β-lactamase is secreted from Amp-resistant plasmid-bearing cells in quantities sufficient to effectively remove ampicillin from a liquid culture medium during culture growth, we replaced the $amp^R$ determinant with $tet^R$ in pDN413 (the in-phase derivative of pJS413 described in Section 5.2.2.). To do this we first created plasmid pDN322 in which the unique PstI site within the $amp^R$ gene in pBR322 was converted to a unique NcoI site. Plasmid pBR322 was opened with PstI and, following limited treatment with Ba131 nuclease, was religated in the presence of synthetic NcoI DNA linkers [5'-CCATGG-3']. The EcoRI-$tet^R$-ori-NcoI fragment (about 3,600 b.p.) was then used to replace the EcoRI-$amp^R$-ori-NcoI fragment (3,064 b.p.) in pDN413 (see FIG. 5) and its EcoRI⁻ (in lacZ) derivative (see section 5.2.2.). The resulting plasmids, pDNT413 and pDNT413R1⁻, now confer Tet-resistance to cells carrying the individual plasmids. The ori site in each is in the opposite orientation but is nonetheless functional. The basic construction can now be transferred into pJS413 or into any of its derivatives.

5.2.4. Changes in the cro Segment

It may or may not be desirable to have the Cro amino acids in the final expressed protein. If the cloned segment encodes a segment of viral capsid protein, for example, the presence of Cro amino acids would not be likely to interfere with antigenicity and may even tend to enhance it. Furthermore, the Cro amino acids may protect the protein in *E. coli* from endogenous proteolytic enzymes. On the other hand, if the cloned segment codes for a protein such as a hormone or an enzyme whose activity is desired, the presence of Cro amino acids on the amino-terminal end of the expressed polypeptide may interfere with such activity. Thus, the cro coding region of pJS413 has been systematically deleted using Bal31 beginning at the BglII site. The BglII site in all cro deletion (croΔ) derivatives was replaced using a synthetic BglII linker. Thus, all croΔ derivatives are identical to the pJS413 parent except for varying amounts of the cro segment (see FIG. 6), plus one additional C-G base pair inserted with the linker adjacent to the cro sequence. Derivatives representing all three reading frames were obtained, allowing cloning in any phase by using any of the restriction sites contained within the linker present in the plasmids or within any new linker that may be subsequently inserted. Some croΔ derivatives were deleted for all of the cro coding sequence and some also for known control regions (SD) regulating translation initiation. CroΔ derivatives retaining the SD region but not the AUG and adjacent coding region provide a system suitable for fusing *any* coding segment carrying its own AUG directly to a known efficient translation initiation control region. In such a plasmid, the distance between the SD and the AUG of the gene can be easily varied. The expression consequences of SD-AUG separation can be monitored to isolate transformed *E. coli* which produce improved yields of the expressed gene. Derivatives deleted for the SD region allow fusion of this promoter system to other given segments for possibly improved yields of the expressed gene.

In-phase croΔ deletion derivatives were abundant among the total croΔ population and endpoints occurred all across the cro coding segment. Therefore, the level of cro-I-Z fusion protein synthesis directed by each can be ascertained and correlated with the deletion endpoint in an attempt to understand the possible role of cro coding sequences on the efficiency of translation of the cro segment. The possibility that portions of the coding region, as well as regions upstream of the coding region, might have a significant influence on the efficiency with which the cro gene itself is translated would provide a strong rationale for attempting to change sequences in the plasmid in order to improve yields of the cro-I-Z fusion. This would be monitored initially by the production of β-galactosidase activity.

5.2.5. Isolation of Over-Production Mutants

Prior to knowing exactly what sequence changes would result in maximal expression, a general system of mutagenesis and selection for strong over-producing mutants was devised. The synthetic oligonucleotide, 5'-TCTAGA-3', is the XbaI recognition sequence. When it is ligated into the SmaI site between cro and I-Z in any in-phase cro-I-Z fusion plasmid, or between cro-X and I-Z in cro-X-I-Z fusion plasmids, a unique XbaI site is inserted, and a UAG (amber codon) is placed in phase with cro-I-Z, or cro-X-I-Z. This blocks efficient production of the fusion protein in Su⁻ (non-suppressor containing) cells, and Lac⁻ cells carrying such plasmids retain the white (Lac⁻) phenotype on Mac-lac plates. However, nonsense codons are subject to a low level of "read-through" translation, possibly due to a low level of suppressor tRNA's in the cell, and a low level of β-galactosidase is nonetheless produced. Alternatively, some ambiguity in codon-anticodon pairing may allow insertion of normal tRNA's at the amber site at some level to allow the low level of β-galactosidase to be synthesized. In any case, if the absolute level of translation initiation events is increased, either by increasing the level of transcription or by increasing the efficiency of translation initiation from a given mRNA, then the absolute level of read-through β-galactosidase synthesis is increased, in some cases to a level sufficient to cause the red colony phenotype in lacΔ strains of *E. coli*. Thus, mutants or novel fusions (see Section 5.12.4.) that allow particularly strong transcription or translation initiation, or whose fusion proteins have increased stability in the cell, can be detected as red colonies on Mac-lac-amp plates. To produce random mutants of existing plasmids, the non-amber-containing plasmid is then grown in the highly mutagenic mutD strain of *E. coli*. To select mutations that affect only the lac promoter or the cro control region, the PstI-BglII Plac-cro-bearing fragment population is excised and reinserted into the non-mutagenized PstI-BglII backbone of the amber-containing plasmid for transformation into the Lac⁻ nonsuppressing host. Transformants exhibiting the red (Lac⁺) phenotype on Mac-lac plates are candidates for regulation or stability mutants. The PstI-BglII Plac-bearing fragment from selected isolates is then isolated and inserted back into the original in-phase plasmid backbone bearing no XbaI linker, and therefore no amber codon, to permit the full extent of over-production of the cro-I-Z or cro-X-I-Z fusion proteins, or any other protein hooked up to the mutant regulation system.

5.2.6. Changes in Plasmid Copy Number

The OPlΔ6 colE1 ori mutation that leads to over-replication of the plasmid has been transferred into the pJS413 plasmid backbone to enable enhanced overexpression of cloned segments.

The plasmid, pSH113, replicates to a level about 50- to 100-fold higher level than pJS413. Plasmid pSH113 was produced using recombinant DNA techniques by replacing the amp-ori region of pJS413 with an analogous region from a derivative of the OPlΔ6 plasmid of Shepard et al. [Cell 18: 267–275, (1979)]. Additionally, the temperature-inducible copy number mutant ori from the R factor carried on plasmid pMOB48 [Bittner and Vapnek, Gene 15(4): 319 (1981)] was transferred to pJS413 in a similar fashion. At 40° C. the plasmid replicates to about 50 to 100 times higher than the level attained at 30° C. or with pJS413 at normal temperatures.

5.3. pMG101

5.3.1. Isolation of Plasmid pMG101

Plasmid pMG101 was constructed by ligating the EcoRI Plac bearing fragment from pKB252 [Backman and Ptashne, Cell 13: 65-71 (1978)] into the EcoRI site of pMC1403 [Casadaban et al., J. Bacteriol. 143: 971 (1980)](see FIG. 7). The plasmid was transformed into *E. coli* MC1000 and colonies resistant to ampicillin and pale blue on XG-amp plates were selected. Plasmid pMG101 DNA was isolated from cleared lysates of *E. coli* MC1000 and the plasmid structure was verified by restriction enzyme and DNA sequencing analysis of the Plac-Z segment. The DNA sequence of the Plac-Z segment shown in FIG. 9 was confirmed from the PvuII site to the EcoRI site near the amino-terminus of the lacZ gene. Note that the EcoRI site near the carboxy terminus has been replaced with the EcoRI$^-$ mutation described in 5.2.2. (see FIG. 8 and Casadaban et al. [supra, (1980)]).

5.3.2. Structure and Description of pMG101

Figure 7A:
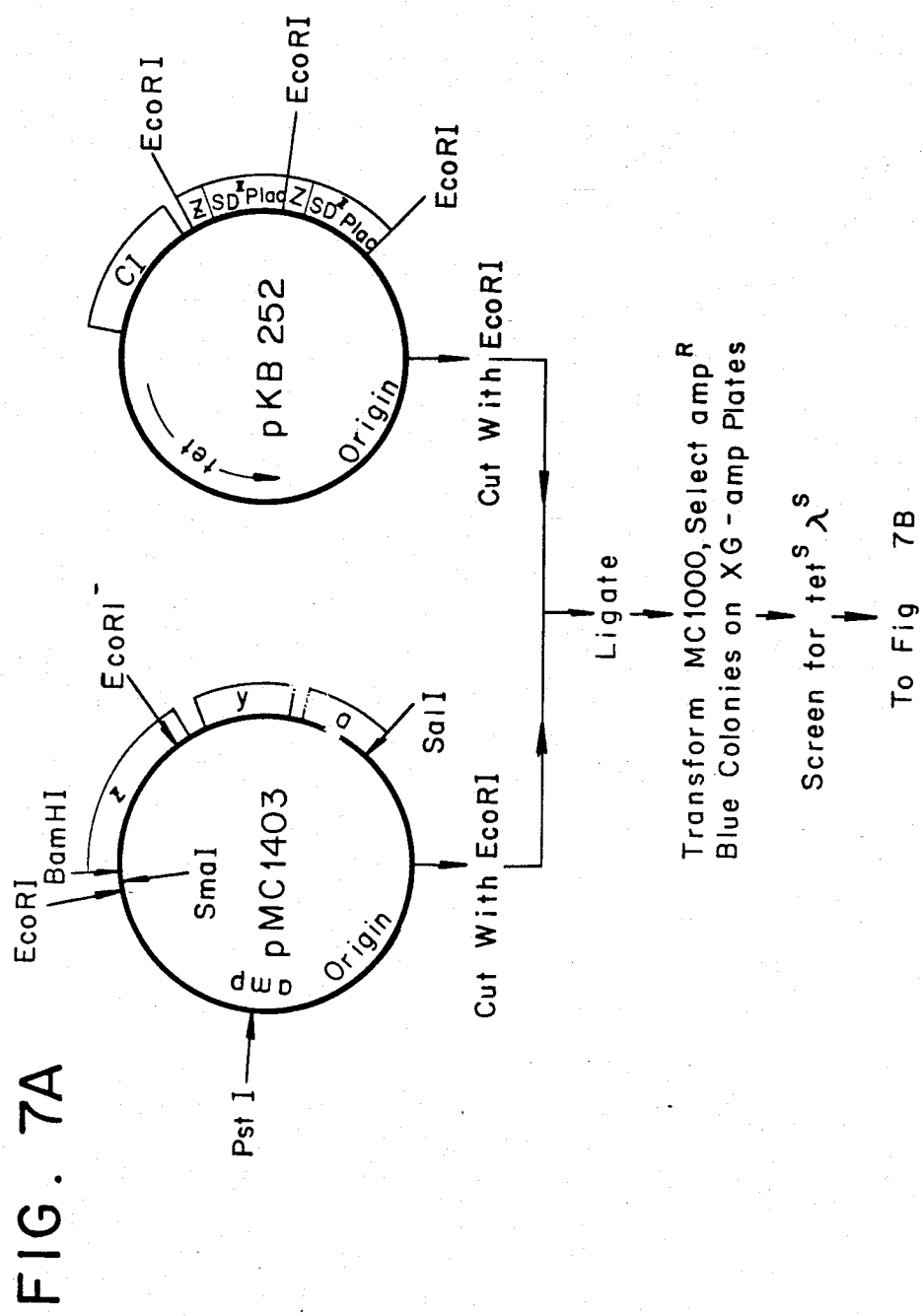
FIG. 7 depicts the steps taken to treat and recombine portions of recombinant plasmids pMC1403 and pKB252 in the construction and isolation of recombinant plasmid pMG101. For an explanation of the lettered segments, see Section 5.3.2.
Figure 7B:
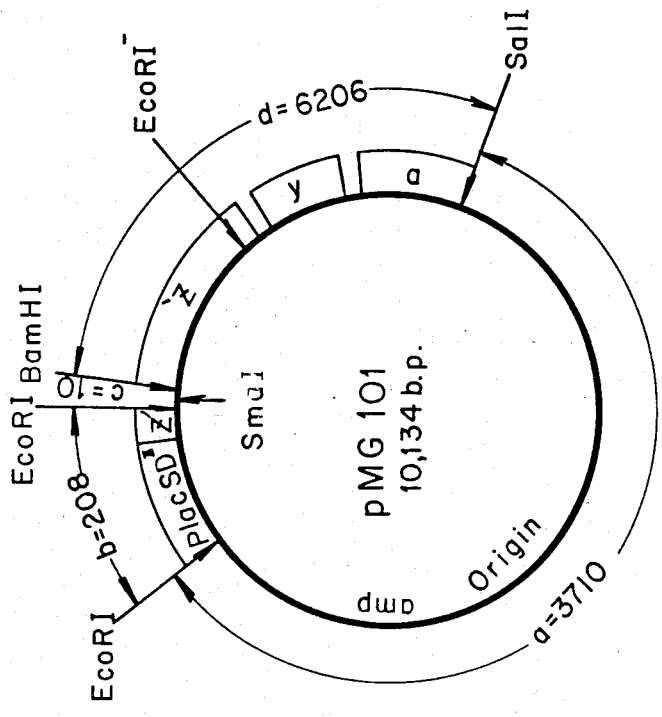
Figure 8:
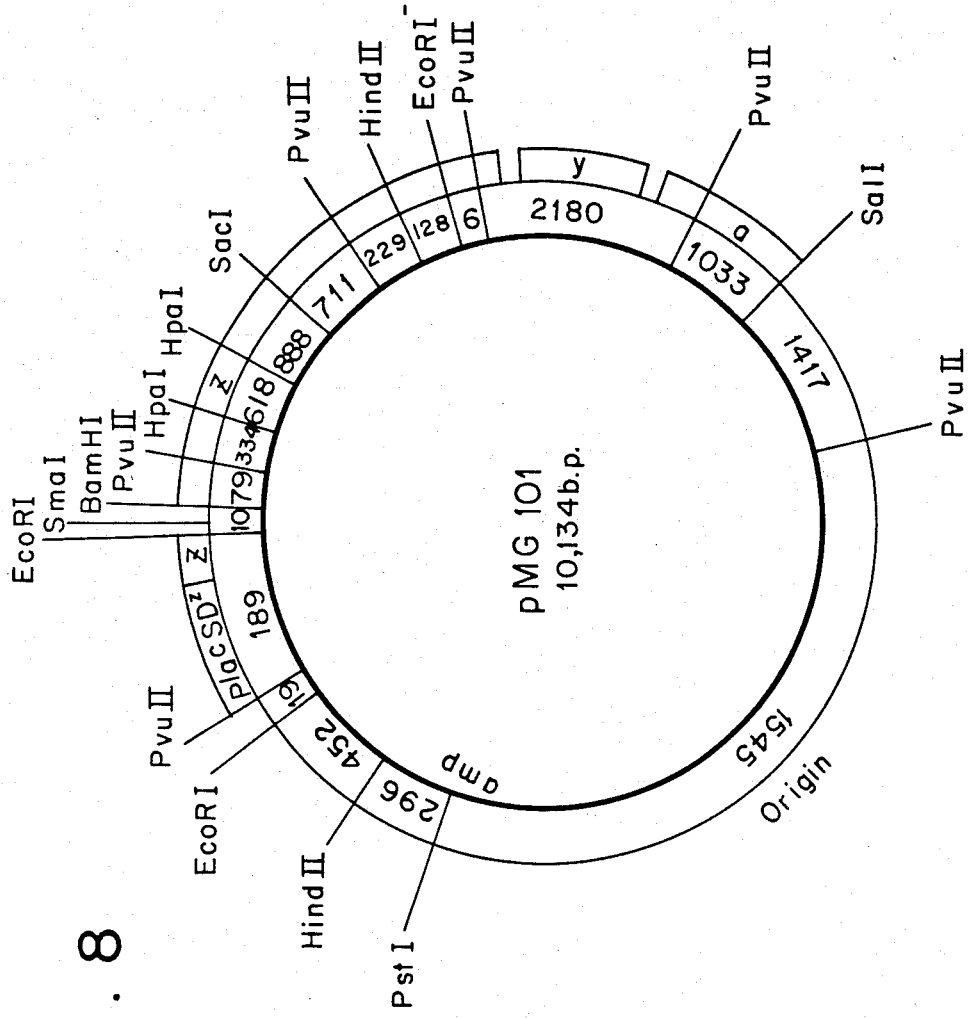
FIG. 8 is a schematic diagram and partial restriction endonuclease cleavage map of recombinant plasmid pMG101.

A schematic diagram of pMG101 (about 10,134 b.p.) is shown in FIGS. 7 and 8. Sub-segment a (3,710 b.p.) is the EcoRI-SalI fragment from pBR322 (Bolivar et al., 1977) containing the β-lactamase gene (amp) and the colE1 origin of replication (ori). Sub-segment b (208 b.p.) contains the HaeIII fragment (203 b.p.) of the lac operon of *E. coli* and bears the UV5 promoter mutation, and the L8 mutation in the CAP binding site. The fragment also bears the lacZ ribosome binding site (SD sequence) and the natural coding sequence (25 b.p.) for the first eight amino acids [Backman and Ptashne, Cell 13: 65–71 (1978)] of the lacZ protein. Sub-segment c (10 b.p.) is a synthetic DNA adapter bearing the SmaI restriction site bounded by EcoRI and BamHI restriction sites. Sub-segment d (6,206 b.p.) includes the lacZ, Y and A genes and is derived entirely from the lac operon. In the Z coding sequence, the first 25 b.p. of the amino-terminal end have been removed.

The contiguous sub-segments b, c, and d (see FIG. 7) in the plasmid represent a normal lac operon, except for (1) its location, (2) the presence of the L8 and UV5 mutations that allow CAP-independent transcription, and (3) the interruption of the natural lacZ coding sequence by the synthetic oligonucleotide linker inserted after the first 25 bases:

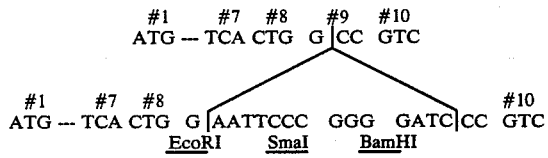

The particular linker (sub-segment c) was included for reasons similar to those described for pJS413, i.e., to provide unique sites (SmaI and BamHI) after the first 25 b.p. of Z for cloning segments of choice, and to place the reading frame of the carboxy-terminal portion of Z out of phase with respect to that of the amino-terminal portion.

Since the linker is (3n+2) 14 b.p. long, translation from the AUG start codon proceeds through the linker and into the Z gene (out of phase) for a total of 59 amino acids before reaching a (UGA) stop codon. Any translation through that nonsense codon could only continue for just over 90 amino acids out of phase before reaching another chain terminating codon. Thus, the plasmid does not direct synthesis of β-galactosidase, and Lac$^-$ cells bearing the plasmid retain their Lac$^-$ phenotype on Mac-lac plates but are pale blue on XG plates (see Section 5.3.1.). Any event that readjusts the reading frame of the amino-terminal portion of Z to that of the portion of Z that resides downstream of the linker allows high level synthesis of β-galactosidase, and is detectable in Lac$^-$ cells.

5.3.3. Use of PMG101 as a Cloning Vehicle

Because the Z gene is in the +2 phase, the use and cloning rationale are the same as described for pJS413, except that SmaI and BamHI are the only cloning sites available.

The presence of a functional lacY product, lac permease, should make detection of β-galactosidase activity in cells growing on Mac-lac plates more sensitive than under LacY$^-$ conditions. However, we have determined recently that cells bearing pJSIIIb, an in-phase version of pMG101 which over-produces lac permease, fail to form colonies on plates containing lactose. LacY$^-$ versions of the plasmid allow normal cell growth in the presence or absence of lactose. Thus, to use pMG101 as a cloning vehicle, plasmid-bearing cells producing high levels of β-galactosidase must be distinguished by the relative intensities of the blue color of colonies on XG plates.

As with pJS413, expression on pMG101 can be easily regulated with lac repressor encoded on the chromosome, on an F' episome, or on a plasmid.

5.4. Derivatives of pMG101

The linker in pMG101 can be varied or expanded as explained in Section 5.2.1. Moreover, the amount of Z gene present (at the amino-terminal end) can be varied to accommodate specific needs. Finally, over-production mutants can be isolated as described for pJS413 (see Section 5.2.5.).

5.5. pJS400

5.5.1. Isolation of Plasmid pJS400

Figure 9:
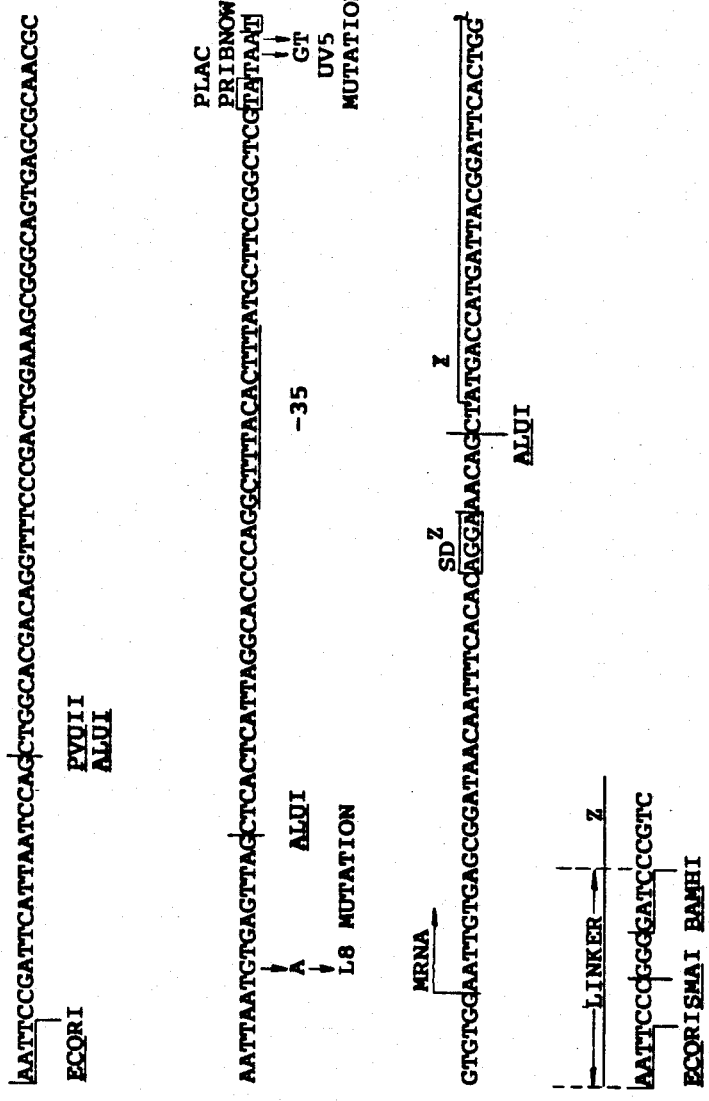
FIG. 9 represents the DNA sequence of the Plac-SD$^Z$-Z-linker segment of recombinant plasmid pMG101.
Figure 10B:
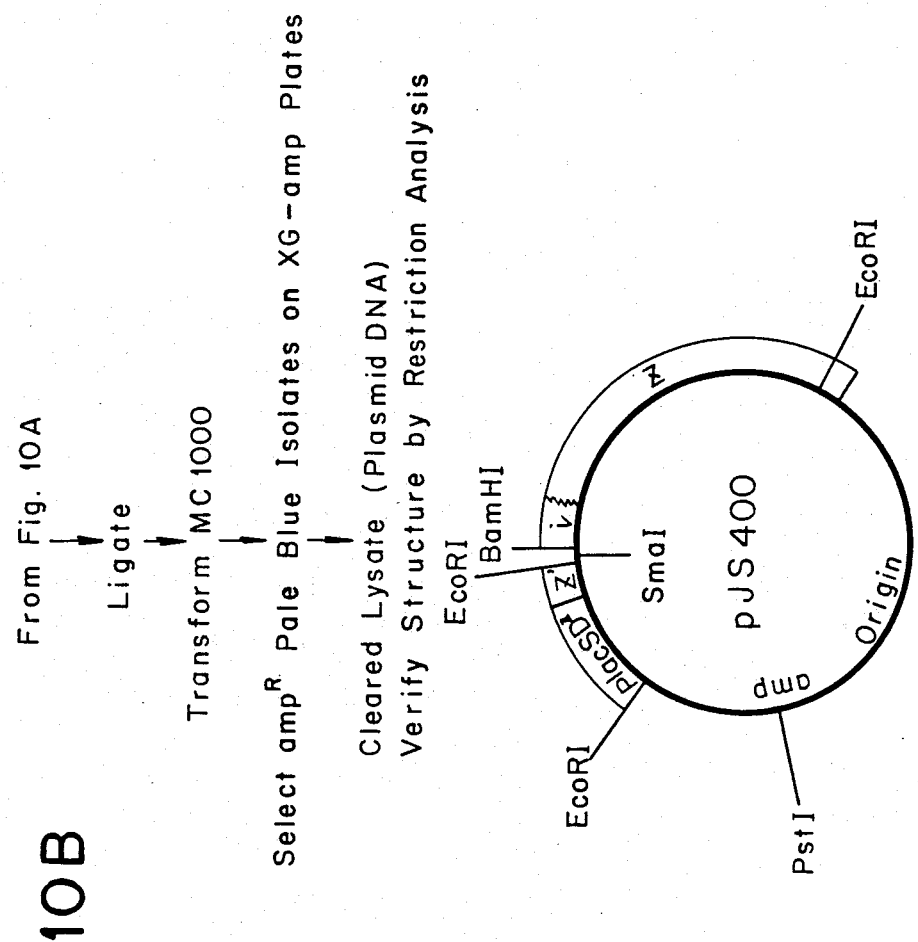
FIG. 10 depicts the steps taken to treat and recombine portions of recombinant plasmids pMG101 and pLG300 in the construction and isolation of recombinant plamid pJS400.
Figure 12:
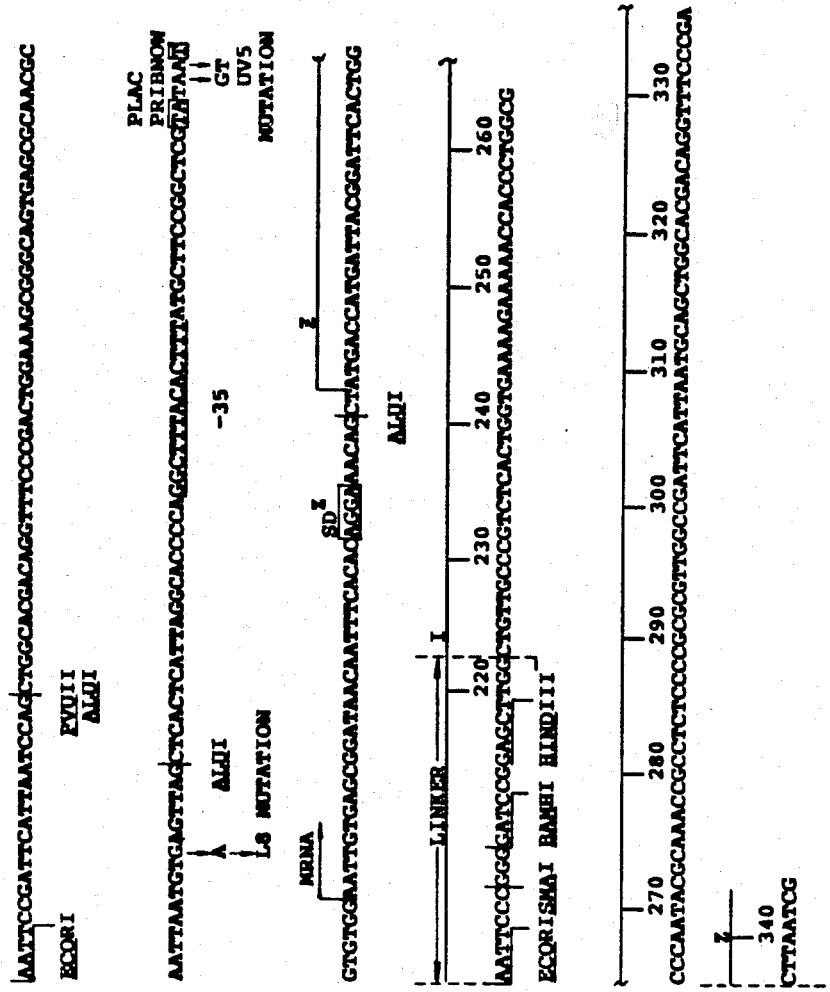
FIG. 12 represents the DNA sequence of the Plac-SD$^Z$-I-Z segment of recombinant plasmid pJS400.

Plasmid pJS400 was constructed by ligating two purified DNA fragments together: (a) the PstI-BamHI Plac-bearing segment from pMG101, and (b) the PstI-BamHI backbone of pLG300 [Guarente et al., Cell 20: 543–553 (1980)](see FIG. 10). The plasmid was transformed into *E. coli* MC1000 and colonies resistant to ampicillin and pale blue on XG-amp plates were selected. Plasmid pJS400 DNA was isolated from cleared lysates of *E. coli* MC1000 and the plasmid structure was verified by restriction enzyme analysis. The Plac-SD$^z$-I-Z segment was not sequenced, but the DNA sequence should be as shown in FIG. 12. [The PvuII-EcoRI sequence, which is identical in pJS400 and pMG101, was confirmed for pMG101 as shown in FIG. 9.]

5.5.2. Structure and Description of pJS400

Figure 11:
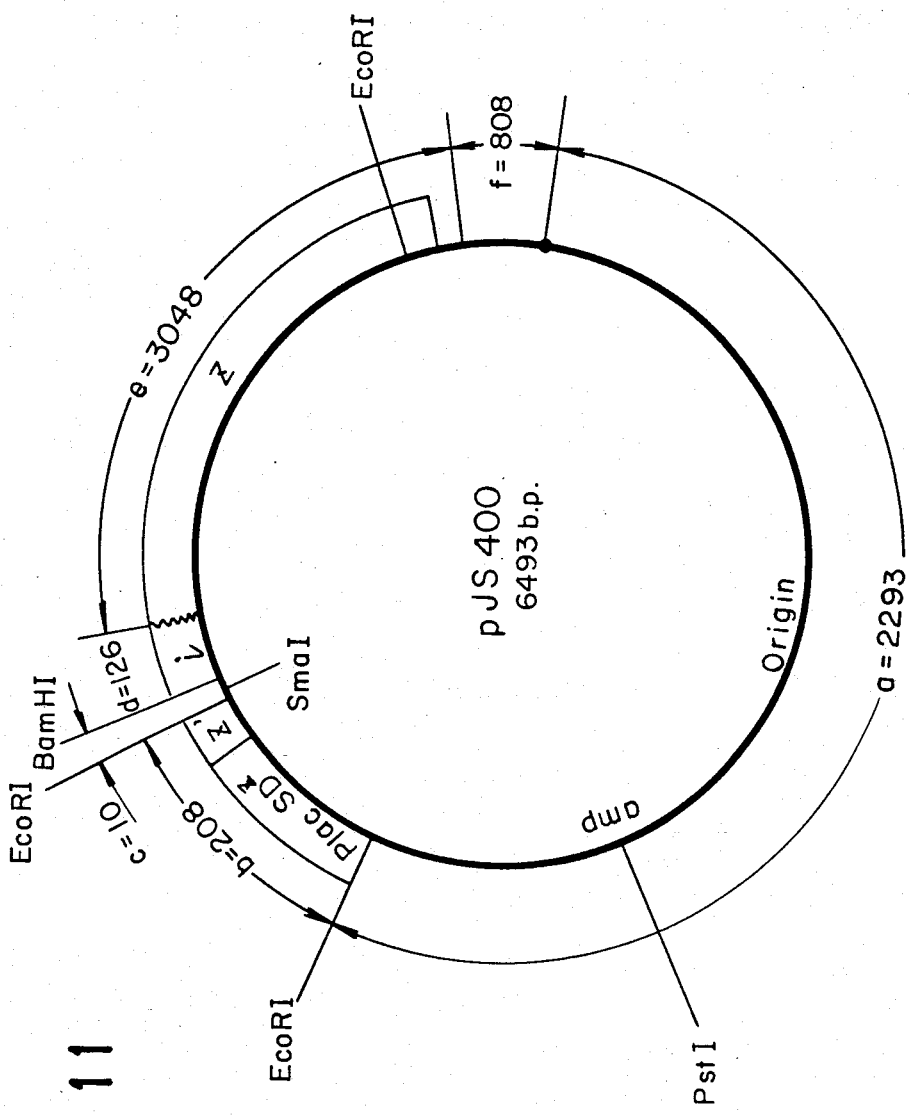
FIG. 11 is a schematic diagram of recombinant plasmid pJS400. For an explanation of the lettered segments, see Section 5.5.2.
Figure 13:
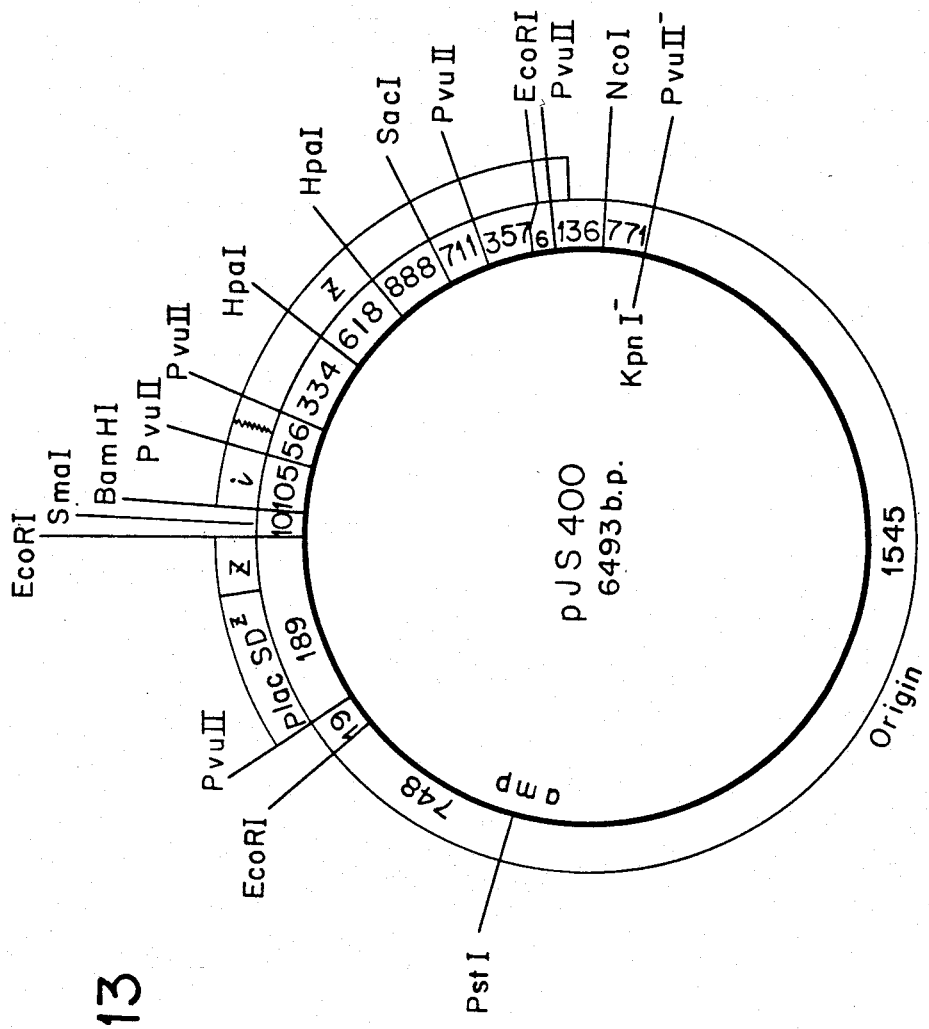
FIG. 13 is a partial restriction endonuclease cleavage map of recombinant plasmid pJS400.

A schematic diagram of pJS400 (6,493 b.p.) is shown in FIG. 11. Sub-segments d, e, f and a correspond to sub-segments e, f, g and a, respectively, of pJS413 (see FIG. 3). Sub-segments b and c correspond to sub-segments b and c, respectively, of pMG101 (see FIG. 8). A partial restriction map of pJS400 is shown in FIG. 13.

The contiguous sub-segments b, c, d and e comprise a hybrid gene, Z-I-Z, whose translational unit is out of phase (+1 phase) beyond the synthetic linker, but which should synthesize a polypeptide of 55 amino acids (8 amino acids of the natural Z gene, 8 amino acids from the linker, and 39 amino acids out of phase from the I gene segment) before reaching a UAA chain terminating codon. Therefore, the plasmid fails to direct synthesis of β-galactosidase, and Lac$^-$ cells bearing pJS400 retain the Lac$^-$ phenotype.

The lac promoter and the synthetic DNA linker were described for pMG101 in Section 5.3.2. and that discussion applies to pJS400. Similarly, the I-Z fusion and its attributes were described for pJS413 in Section 5.1.2. and that discussion also applies to pJS400.

5.5.3. Use of pJS400 As a cloning vehicle pJS400 can be used as a cloning vehicle in a manner similar to that described for pJS413 and pMG101 in Sections 5.1.3 and 5.3.3., respectively. Because the plasmid is lacY−, cells bearing the plasmid or any of its in-phase derivatives can be grown normally in the presence or absence of lactose. However, E. coli MC1000 cells carrying in-phase derivatives of pJS400, e.g., pDN400, do not synthesize sufficient quantities of β-galactosidase to allow the red colony Lac+- phenotype. E. coli 51-15 [which is also known as E. coli X7770 (φ80dlacZΔM15)/F'lacI$^{QS}$ΔM15pro+, derived from E. coli CSH51; see Miller, Experiments in Molecular Genetics, Cold Spring Harbor Laboratory, Cold Spring Harbor, N.Y., p. 20 (1972)]is LacY+ and allows the red colony phenotype for the in-phase plasmids only.

5.6. Derivatives of pJS400

Plasmid pJS400 can be easily modified to accommodate specific needs and requirements in a similar way to that described for pJS413 and pMG101 in Sections 5.2. and 5.4., respectively.

5.7. pDN455

5.7.1. Isolation of Plasmid pDN455

Figure 14B:
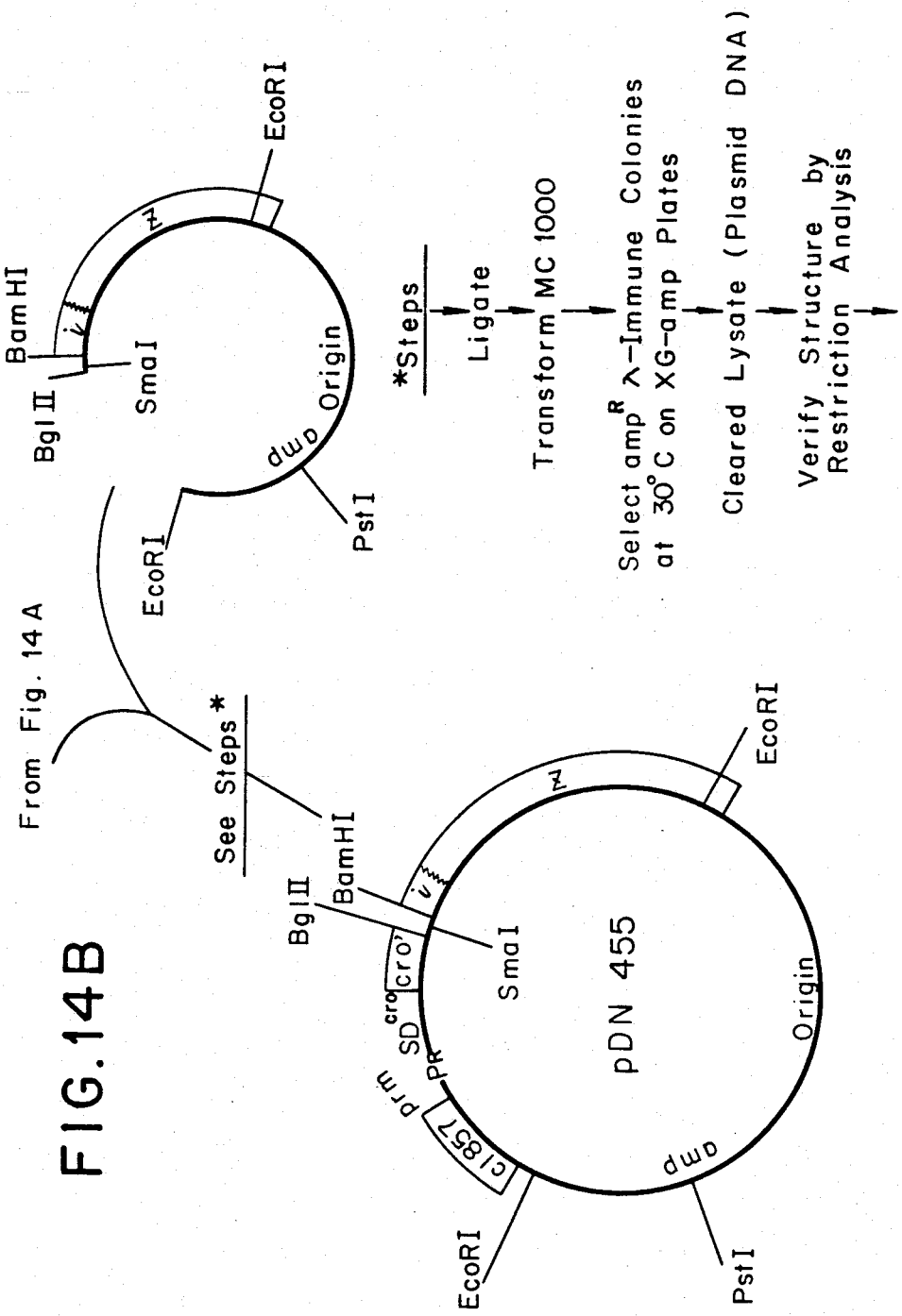
FIG. 14 depicts the steps taken to treat and recombine portions of recombinant plasmids pJS55 and pJS413 in the construction and isolation of recombinant plasmid pDN455.

Plasmid pDN455 was constructed in several steps (see FIG. 14). First, the PstI site between the cI and rex genes of plasmid pJS55 (See Section 5.9.2.) was converted to an EcoRI site by partial digestion with PstI, treatment with S1 nuclease followed by religation in the presence of a synthetic oligonucleotide (octamer) carrying a restriction site for EcoRI. The BglII-EcoRI fragment bearing the cI857-cro segment from the resulting plasmid was then purified and ligated into the BglII-EcoRI backbone (produced by partial EcoRI digestion) from pJS413 to yield plasmid pDN455.

Plasmid pDN455 was transformed into E. coli MC1000. Ampicillin resistant and λ-immune colonies were selected on XG-amp plates at 30° C. The XG-amp plates were used to appraise leakage of the cI857-$O_R$ repression system on the plasmid, i.e., if blue, then leaky. The colonies were white after 24 hours, but became slightly pale blue upon continued incubation. The 30° C. temperature is the permissive temperature for cI857 λ repressor. [The cI857 λ repressor is active in the range of about 30-33° C. and is inactive in the range of about 39-42° C.]Above 37° C. the colonies become bluish on XG, even though the cro-I-Z fusion is out of phase (see discussion in Section 5.1.1. for pJS413). The translation reading frame in the plasmids can be readjusted to allow production of the cro-I-Z fusion protein at elevated temperatures; colonies of MC1000 cells bearing these plasmids are tiny at temperatures above 37° C. and appear at a much reduced plating efficiency (about $1 \times 10^{-4}$; see also Section 5.7.3.), but they are deep blue on XG-amp plates and very red on Mac-lac-amp plates.

Figure 16:
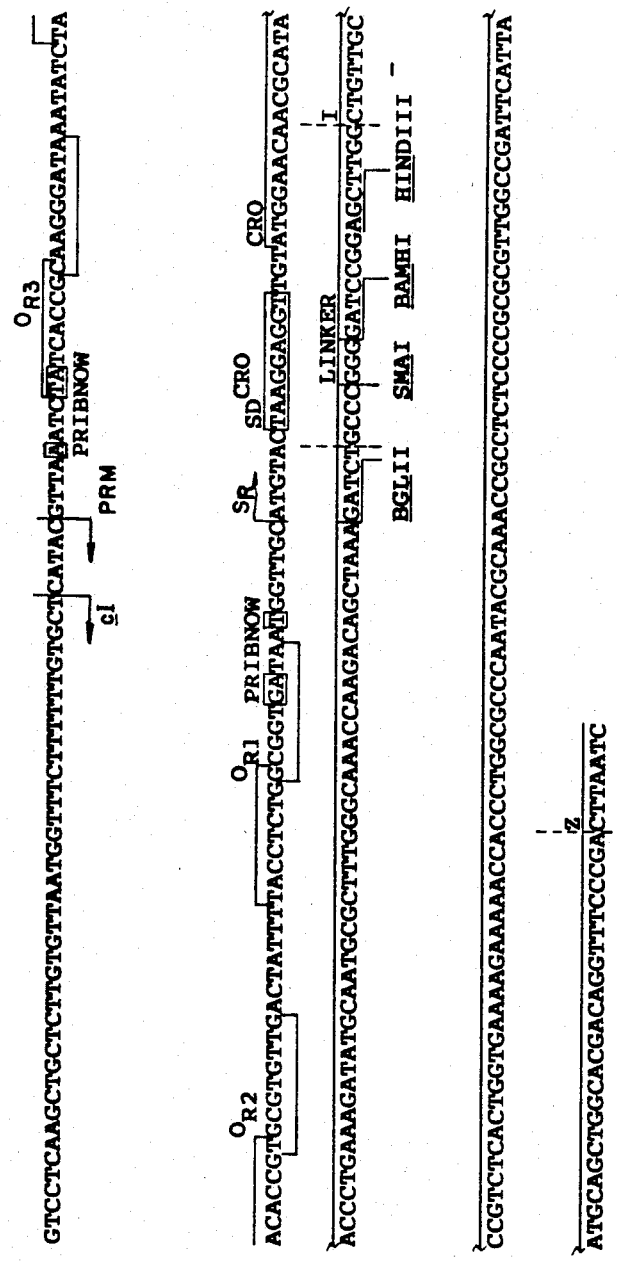
FIG. 16 represents the DNA sequence of the SD$^{cro}$-cro-linker-I-Z segment of plasmid pDN455.

Plasmid pDN455 DNA was isolated from cleared lysates of E. coli MC1000 and plasmid structure was verified by restriction enzyme analysis. Plasmid pDN455 DNA was not sequenced. However, most of the individual segments used in the construction of pDN455 have been adequately sequenced [for the λ DNA portion, see Ptashne, IN: The Operon, Miller and Reznikoff, (Eds.), Cold Spring Harbor Laboratory, Cold Spring Harbor, N.Y., pp. 325-344 (1980), and Landsmann, et al., Gene (in press, (1982)]. The sequence of the relevant SD$^{cro}$-cro-BglII-SmaI-BamHI-I-Z segment is shown in FIG. 16.

5.7.2. Structure and Description of pDN455

Figure 15:
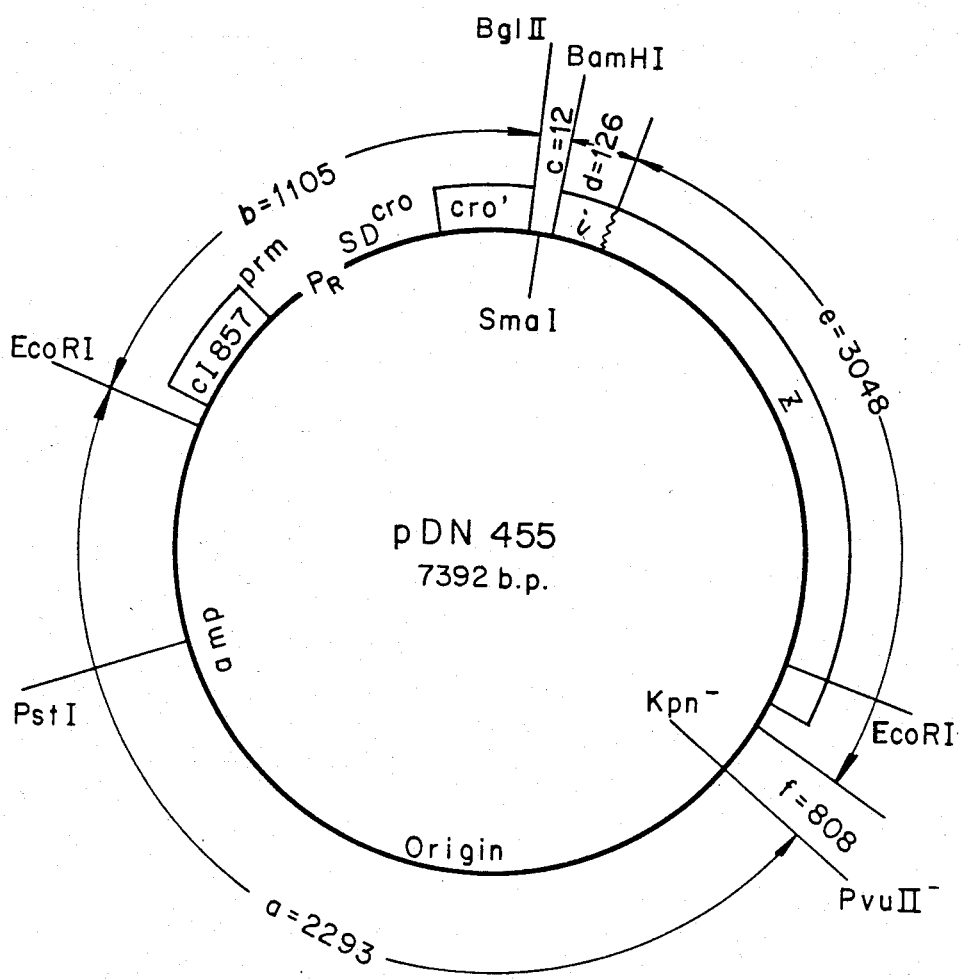
FIG. 15 is a schematic diagram of recombinant plasmid pDN455. For an explanation of the lettered segments, see Section 5.7.2.
Figure 17:
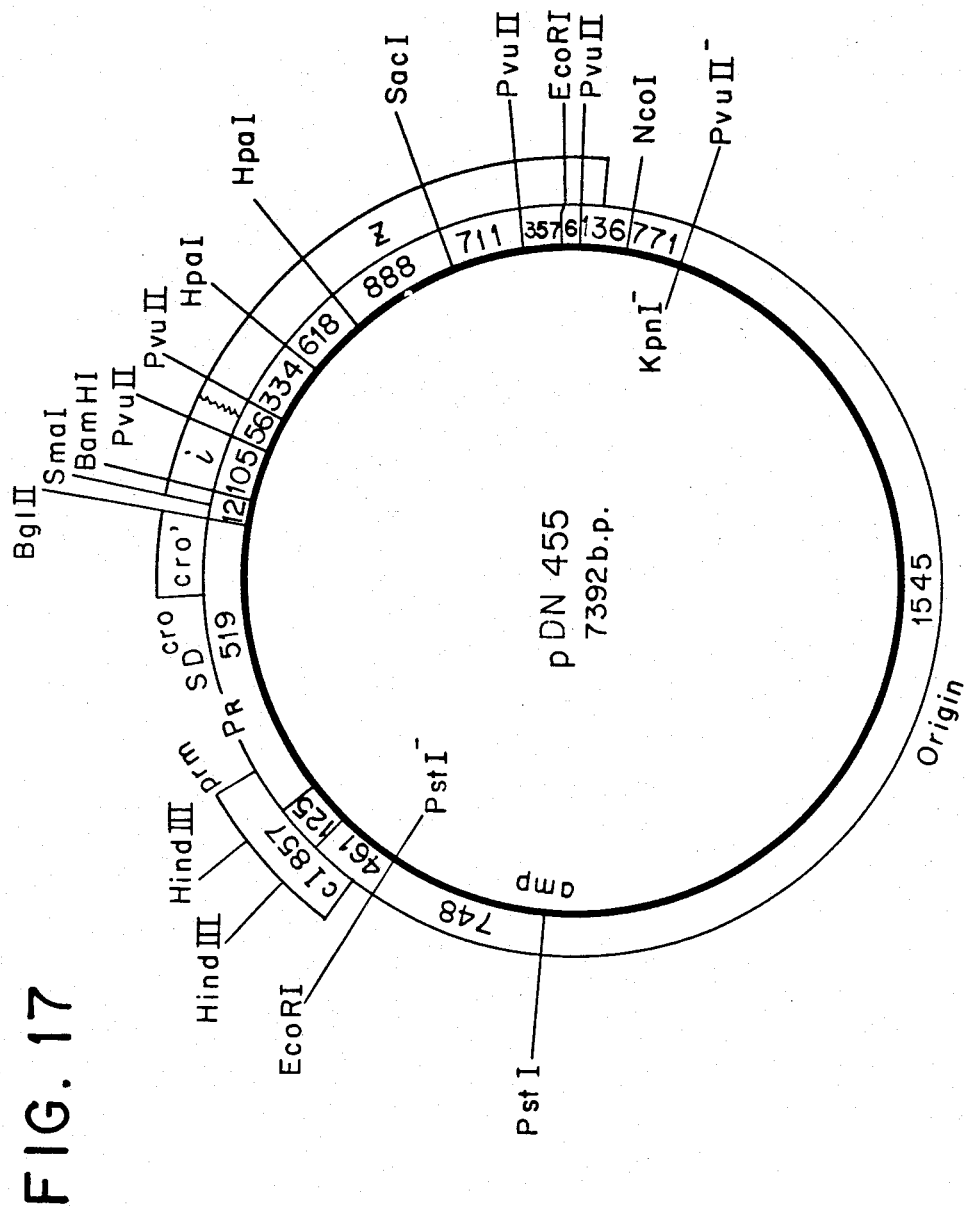
FIG. 17 is a schematic diagram and partial restriction endonuclease cleavage map of recombinant plasmid pDN455.

A schematic diagram of pDN455 (7,392 b.p.) is shown in FIG. 15. [A partial restriction map is shown in FIG. 17.]Sub-segment b (1,105 b.p.) is from bacteriophage λ and includes the λ repressor gene (cI857) and its promoter, prm, the rightward promoter-operator region, $P_R$-$O_R$, the SD sequence for the cro gene, and the first 68 b.p. of the cro coding sequence. Sub-segments c, d, e, f and a, are the same as sub-segments d, e, f, g and a, respectively, of pJS413 (Section 5.1.2.). Thus, the cro-I-Z portion of the hybrid gene in pDN455 (FIG. 16) is identical to that in pJS413 and is translated out of phase as in pJS413 with all the same consequences described for pJS413. The pertinent differences between pDN455 and pJS413 are: (a) Plac of pJS413 has been replaced with λ $P_R$ which directs higher levels of transcription (b)λ$P_R$ is accompanied by the $O_R$ operator so that transcription is sensitive to repression by λ repressor; and (c) The λ repressor (cI857) gene is carried on the plasmid allowing high levels of repressor to be made in the cell which results in tight control of gene expression on pDN455. Because the cI857 mutation causes the repressor to be temperature-sensitive, transcription from $P_R$ can be induced simply by raising the temperature. This affords a simple and inexpensive means of turning on synthesis of the cloned gene, although this may be undesirable if the product is itself temperature sensitive.

5.7.3. Use of pDN455 as a Cloning Vehicle

The theory of cloning into pDN455 is the same as described for pJS413 with the practical exceptions stated above in Section 5.7.2. One limitation introduced by having the cI857 gene carried on the plasmid is that it has restriction sites that may be inconvenient, such as HindIII. Furthermore, the temperature range in which expression can occur is restricted to temperatures above 39° C. However, the tight regulability and ease of induction, coupled with the strength of the $P_R$ promoter system, make it attractive, both as a shot-gun cloning system and for use in direct cloning experiments.

Derepression of the $P_R$ promoter on a pBR322-like plasmid, as with $P_L$, causes cells harboring in-phase versions of such plasmids to die (see also Section 5.9.2.). Thus, derivatives which spare such lethality (see Sections 5.8.4. and 5.10.2.) are better suited for the shot-gun cloning procedure. Derepression of cells bearing pDN455 itself is not lethal since the coding sequences of the cro and of the I-Z segments are out of phase with respect to each other (see Section 5.10.2.).

5.8. Derivatives of pDN455

5.8.1. Changes in the Linker

The same sorts of linkers described for pJS413 (see Section 5.2.1.) can be easily transferred into pDN455 (which, like pJS413, is in the +2 phase), including those which change the reading frame of the restriction sites with respect to either the cro segment or the I-Z segment, or both.

5.8.2. Changes in the cro Segment

The croΔ derivatives from pJS413 (Section 5.2.4.) can be transferred into the pDN455 background by genetic recombination in vivo. Alternatively, new croΔ mutants can be and, in fact, were generated as described for pJS413 (Section 5.2.4.). BglII and SalI linkers were each used, the latter to produce the pDN200 series from which the proper EcoRI-SalI cI857-$P_R$-croΔ fragment can be excised for use in constructing the pDH800 series (see Section 5.12.5.).

5.8.3. Isolation of Over-Production Mutants

The procedure described in Section 5.2.5. for pJS413 can be used to isolate overproduction mutants of pDN455.

5.8.4. Isolation of pDN455t

One means of preventing lethality of derepressed $P_R$ plasmids, as observed for in-phase versions of pDN455 (see Section 5.7.3.), is to insert a transcription termination signal at some site downstream of the cro-I-Z segment. The 332 b.p. fragment from phage fd [Beck and Zink, Gene 16: 35–58 (1981)] which bears a strong transcription termination signal has been shown to be effective in blocking lethality caused by other strong promoters cloned into pBR322-like plasmids [Gentz et al. Proc. Natl. Acad. Sci., U.S.A. 78: 4936–4940 (1981)]. The analogous fragment from phage M13 can be inserted into pDN456 (a derivative of pDN455 which is deleted for the first 111 b.p. to the right of the SmaI cleavage site to produce an in-phase cro-I-Z fusion) at the unique NcoI site within the lom gene (sub-segment f; see also FIG. 5) to block $P_R$-induced lethality. The resulting plasmid residing in E. coli MC1000 cells should not kill its host, but should allow the cro-I-Z fusion protein to be made continuously. A similar derivative of pDN455 can be made to allow cells bearing newly generated cro-X-I-Z in-phase fusion plasmids (as described in Section 5.1.3.) to survive when derepressed.

5.8.5. Elimination of the EcoRI Site in lacZ

The EcoRI+ site in lacZ was replaced in pDN456 (the in-phase derivative of pDN455 described in Section 5.8.4.) with the EcoRI− mutation in the manner described in Section 5.2.2. for the purpose described there.

5.8.6. Substitution of the Tet$^R$ Marker for amp$^R$

A Tet-resistant derivative of pDN456 (the in-phase version of pDN455 described in Section 5.8.4.) and of its EcoRI− (in lacZ) derivative were constructed in the same manner as described in Section 5.2.3. for the reasons stated there. Tet-resistant versions of pDN455 or any of its derivatives can be constructed simply by exchanging fragments by standard recombinant DNA techniques.

5.9. pJS55 and pDH55

5.9.1. Isolation of Plasmid pDH55

Figure 18A:
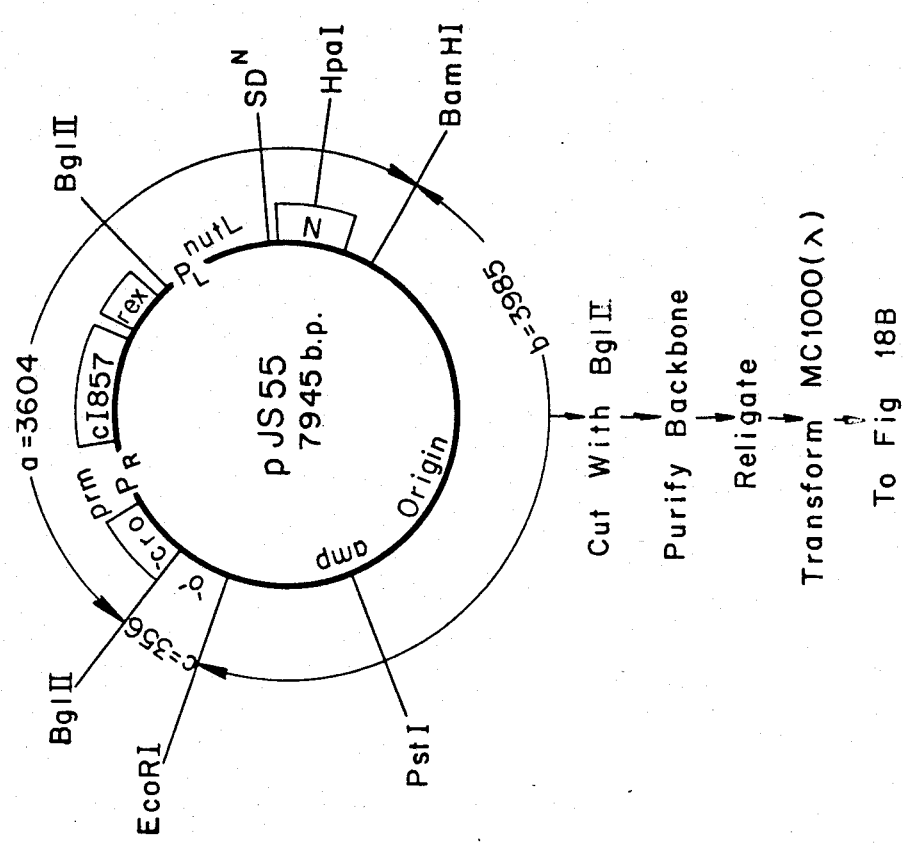
FIG. 18 depicts the steps taken to convert recombinant plasmid pJS55 into recombinant plasmid pDH55.
Figure 18B:
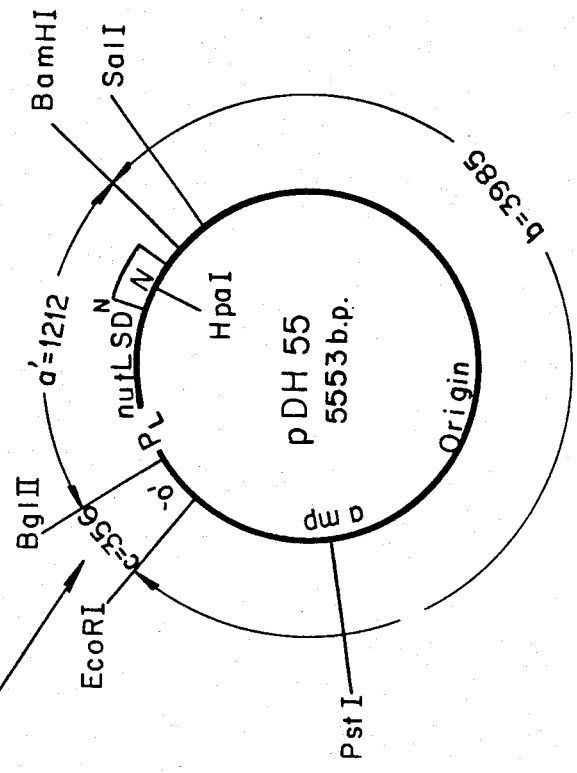

Plasmid pDH55 (5,553 b.p.) was constructed by cutting pJS55 with BglII, purifying the $P_L$-N-bearing backbone and religating, thus removing the $P_R$-cI857 segment (see FIG. 18). It was transformed into a λlysogen of E. coli MC1000 and ampicillin-resistant colonies were selected. Mini-cleared lysates of E. coli MC1000(λ) were prepared and plasmid pDH55 DNA was isolated. The structure of pDH55 was verified by restriction enzyme analysis.

5.9.2. Structure and Description of pJS55 and pDH55

A schematic diagram of pJS55 is shown in FIG. 18. Sub-segment a (about 3,604 b.p.) is from bacteriophage λ and includes the N gene (one of the early λ genes coding for an antitermination protein which antagonizes transcription termination functions), the nutL site (the site of N protein utilization in the leftward $P_L$ promoted operon), the major leftward promoter-operator region ($P_L$-$O_L$), the rex gene (which codes for a protein that inhibits the growth of unrelated E. coli phages), the cI gene (coding for λ repressor containing the cI857 temperature-sensitive mutation along with the cIind− mutation which prevents prophage from being induced by ultraviolet irradiation), the rightward promoter-operator region ($P_R$-$O_R$, and also prm) and the amino-terminal one-third of the cro gene. Sub-segment b (3,985 b.p.) is the large EcoRI-BamHI fragment of pBR322 and contains the β-lactamase gene (amp) and the colEl origin of replication (ori). Sub-segment c (356 b.p.) is an internal segment of the O gene of bacteriophage λ and presumably has no residual function.

Figure 19:
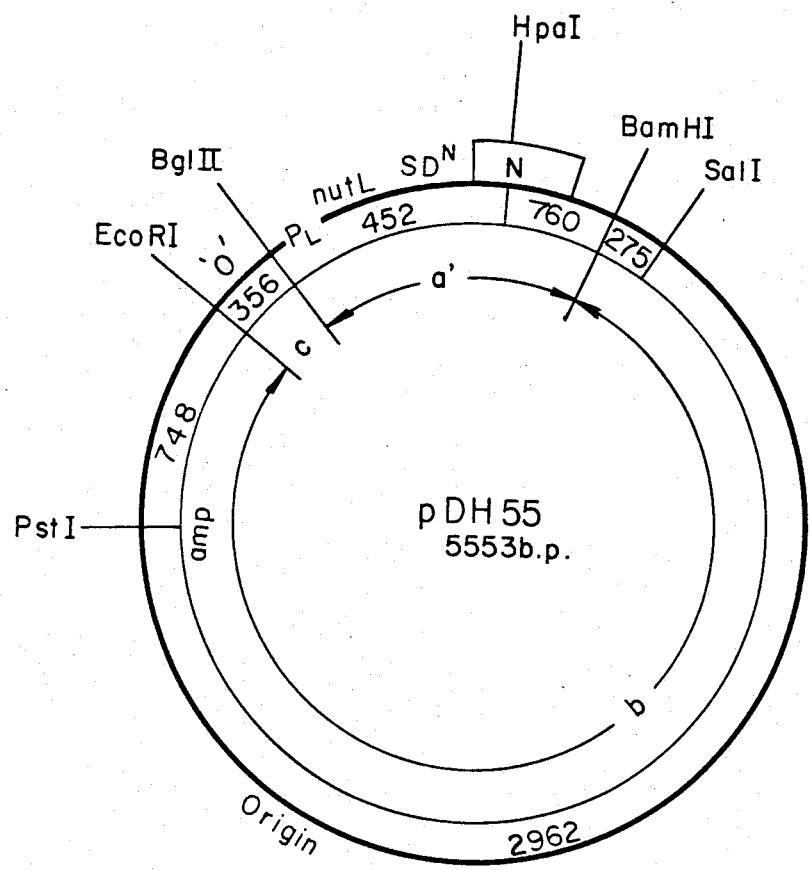
FIG. 19 is a schematic diagram and partial restriction endonuclease cleavage map of recombinant plasmid pDH55.

A schematic diagram and partial restriction map of pDH55 is shown in FIG. 19. It is similar to pJS55 except that the BglII-rex-cI-cro-BglII segment is absent, leaving segment a' (1,212 b.p.) containing only the N-nutL-$P_L$-$O_L$ region. Sub-segments b and c are identical to those described for pJS55.

In the absence of functional λ repressor, transcription from $P_L$ can be initiated and can continue through the nutL site and N gene to allow N protein to be synthesized. N protein, in conjunction with the nutL site, allows $P_L$-directed transcription to be antiterminated at transcription termination signals beyond nutL. In the absence of functional λ repressor, however, cells bearing plasmids such as pJS55 and pDH55 fail to form colonies on agar plates containing ampicillin, even though a functional β-lactamase gene resides on the plasmid. Colonies which form in the absence of ampicillin are segregants that contain no plasmid. Thus, $P_L$-initiated transcription on pBR322-like plasmids is lethal to the cells, or interferes with the expression of some essential plasmid function, such as plasmid replication, or β-lactamase gene expression. In either case, the level of β-lactamase produced would be insufficient to prevent the cytotoxicity of ampicillin. Thus, pJS55 must be grown and maintained in cells at 30° C., at which temperature the cI857 repressor encoded by the plasmid is functional and maintains repression of $P_L$. Plasmid pDH55 must be grown in cells containing functional λ repressor provided in trans by a prophage or a partial prophage carrying either cI+ or the cI857 allele.

5.9.3. Use of pJS55 and pDH55 as Cloning Vehicles

Plasmids pJS55 and pDH55 allow cloning and high-level c expression of several general classes of gene segments. The cloning sites are (a) the unique HpaI site which lies within the N gene, (b) the BamHI site downstream of the N gene, (c) sites created by inserting linkers of choice into either the HpaI site, the BamHI site, or both.

Cloning into the N gene interrupts the gene and prevents synthesis of functional N protein. The inserted gene segment nonetheless may be transcribed at a high level as part of the $P_L$-initiated transcript. If the segment also contains transcription termination signals, N protein can be supplied in trans, using the proper host, to overcome such potential transcriptional blocks. Although the BamHI site is preceded by a transcription termination signal, gene segments cloned into the BamHI site may be transcribed normally since the N gene is transcribed first and its product, together with the nutL site, can effect antitermination at the termination site.

If the cloned segment contains an intact gene of contiguous coding sequence preceded by a functional translation initiation control sequence (SD sequence) complete with an initiating codon, then the natural intact polypeptide may be synthesized whether cloned into the HpaI site or into the BamHI site. If such a segment is truncated for the carboxy-terminal end of the gene and if the segment is cloned into the HpaI site in phase with the carboxy-terminal portion of the N gene, then a fusion protein results.

If the cloned segment has no functional SD sequence in front of the gene, or is truncated for the amino-terminal portion of the gene, then translation of the segment must depend on control signals provided by the N gene. Resulting proteins are necessarily fusion proteins carrying the amino-terminal portion of the N protein on the amino-terminal side, and perhaps the carboxy-terminal portion of the N protein on the carboxy-terminal side. Thus, the main utility of plasmids pJS55 and pDH55 is in cloning specific fragments.

Since fusion of the cloned segment in phase with the N gene is not necessarily easily detected (except through immunological screening techniques, for example), plasmids pDH36, pDH72 and pDH438 were devised. These plasmids employ the β-galactosidase fusion technology described for pJS413, and other plasmids, to aid in the primary detection of fusion gene expression in either shot-gun or direct cloning experiments.

5.10. pDH26, pDH36 and pDH72

5.10.1. Isolation of Plasmids pDH26, pDH36 and pDH72

Figure 20A:
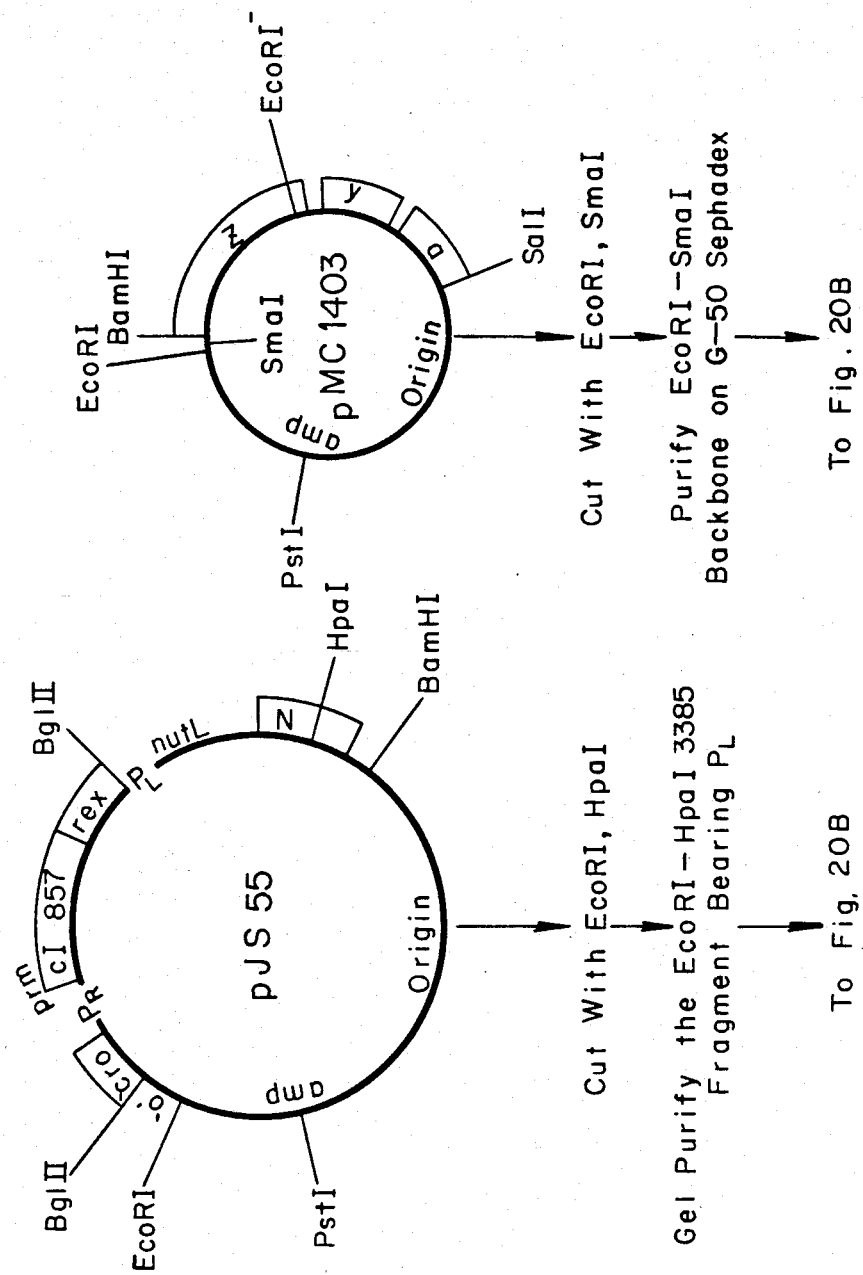
FIG. 20 depicts the steps taken to treat and recombine recombinant plasmids pJS55 and pMC1403 in the construction and isolation of recombinant plasmid pDH26.
Figure 20B:
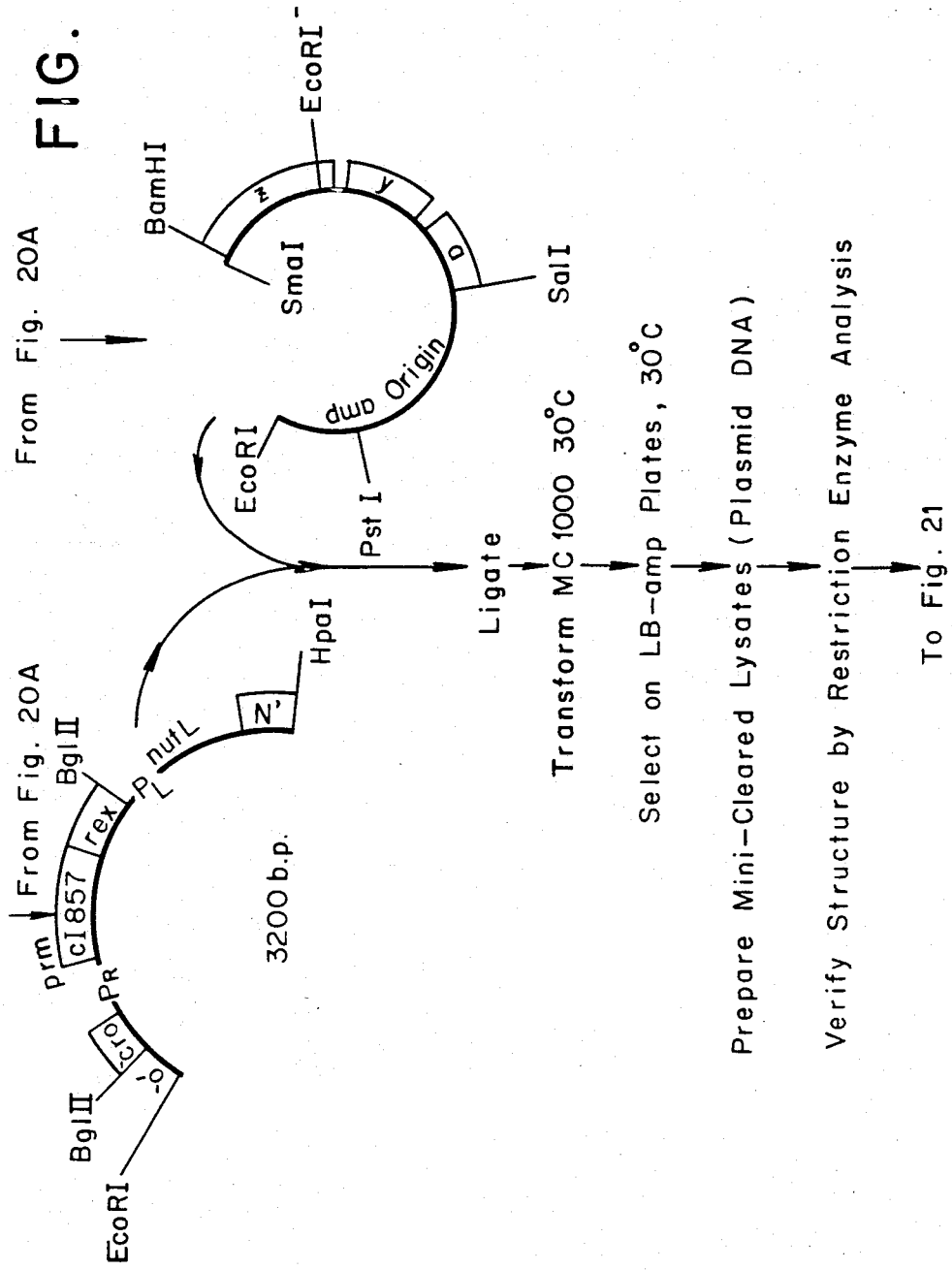
Figure 21:
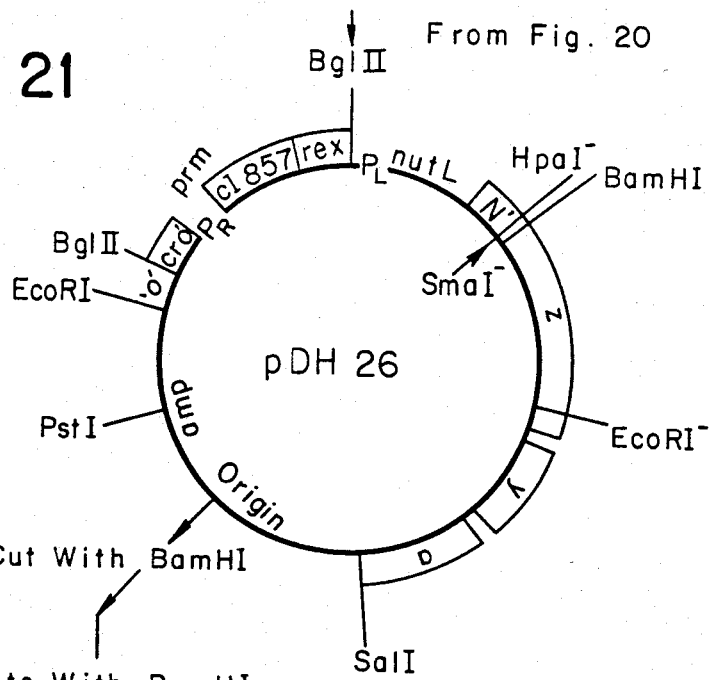
FIG. 21 is a schematic diagram of recombinant plasmid pDH26 and indicates the steps taken to construct and isolate recombinant plasmid pDH36.
Figure 21:
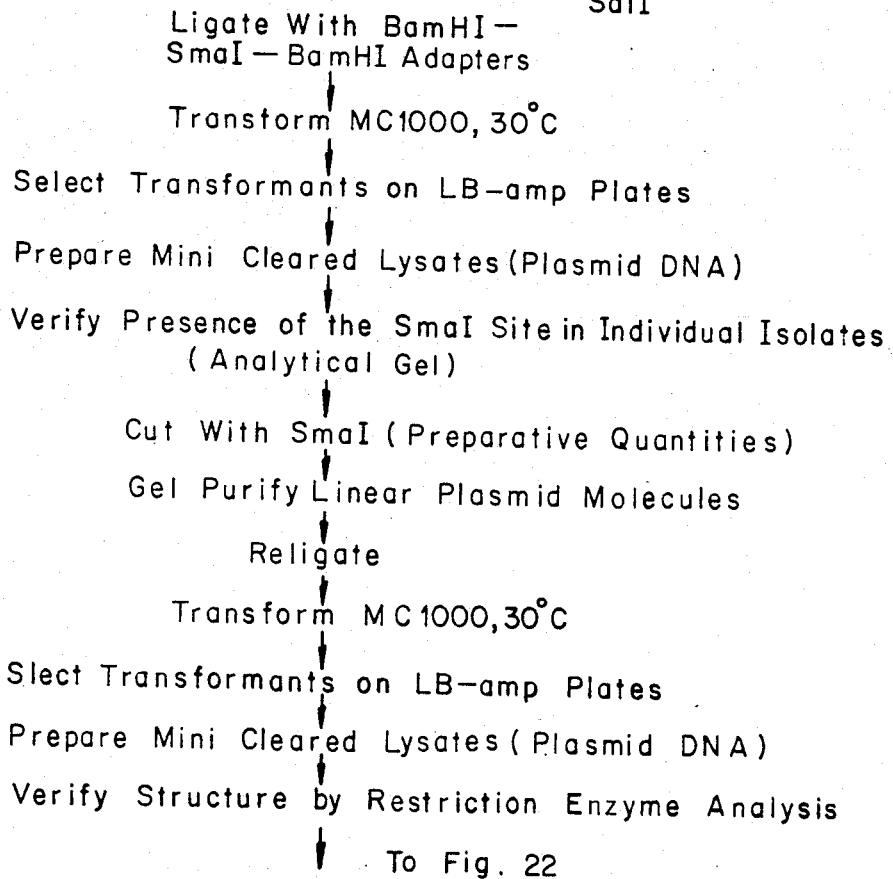
Figure 22A:
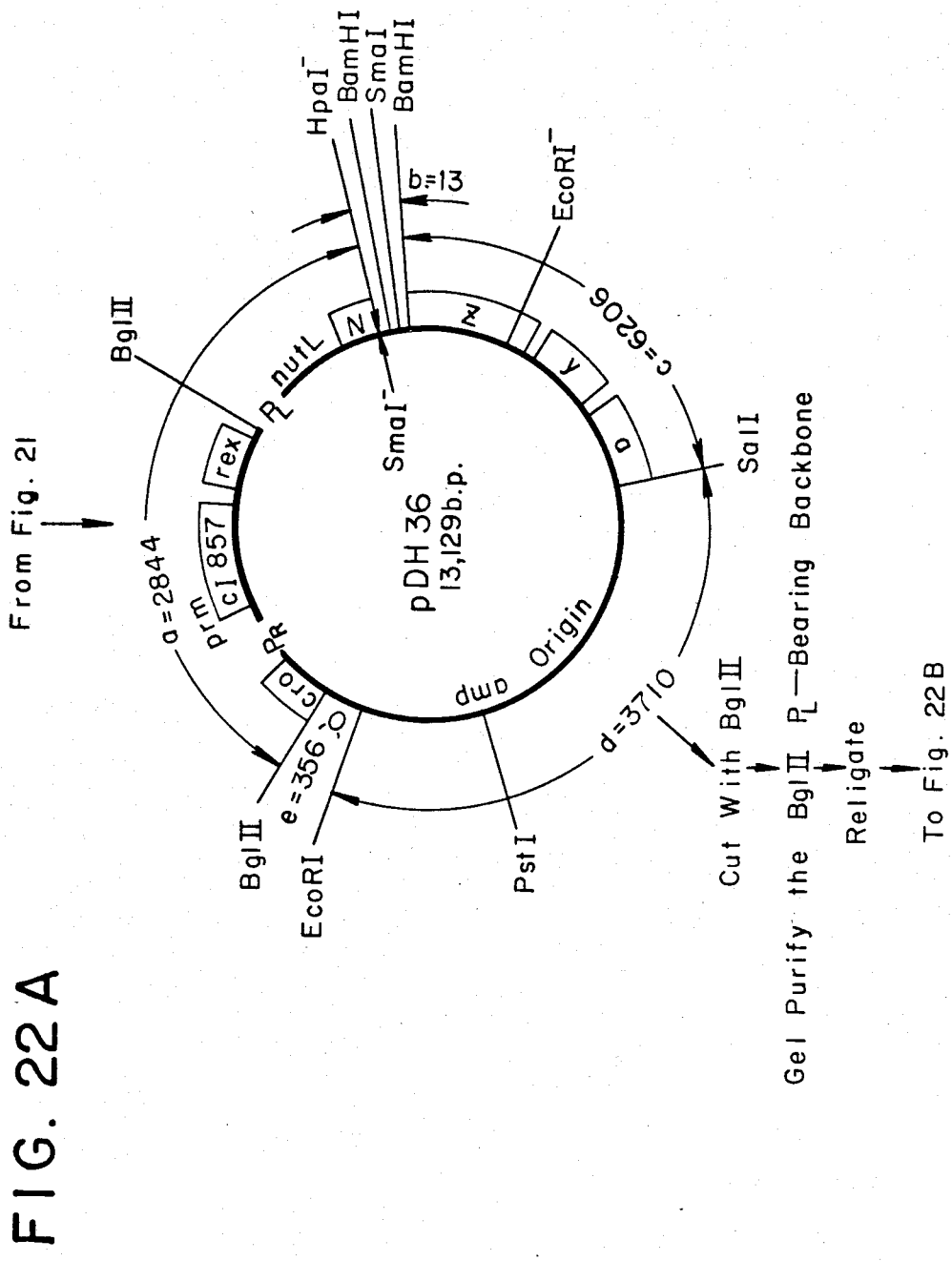
FIG. 22 presents schematic diagrams of recombinant plasmids pDH36 and pDH72 and indicates the steps taken to convert pDH36 to pDH72.
Figure 22B:
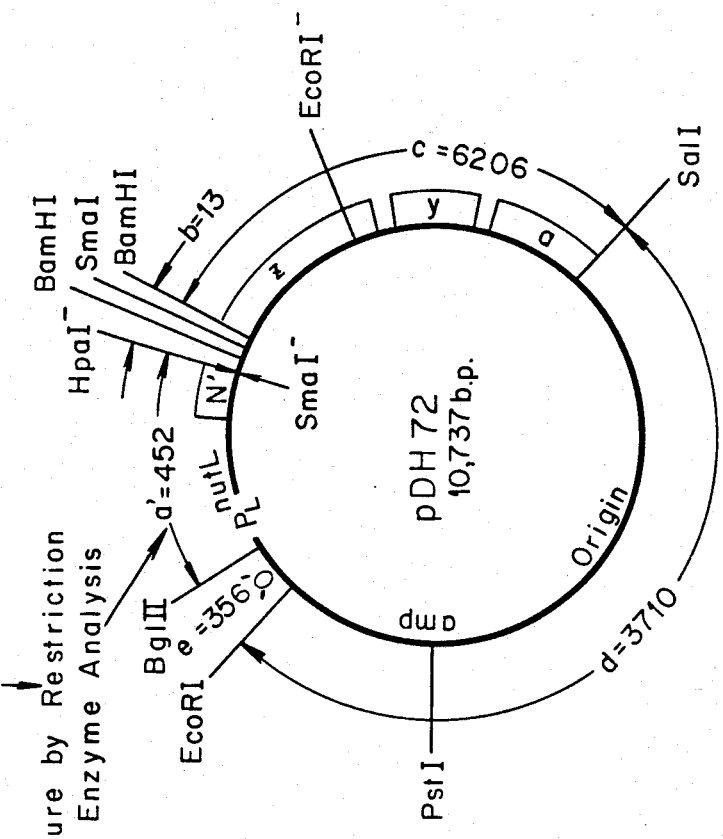

The EcoRI-HpaI $P_L$-cI857-$P_R$ fragment (3200 b.p.) from pJS55 was purified and ligated into the EcoRI-SmaI backbone of pMC1403 to yield pDH26. (See FIGS. 20 and 21) Plasmid pDH36 (FIG. 22) was created by inserting the BamHI-SmaI-BamHI synthetic oligonucleotide adapter into the BamHI site of pDH26 to throw the N-Z fusion out of phase. [The BamHI-SmaI-BamHI adapters are deoxy 5'-GATCCCCGGG-3' and were supplied by BioLogicals, Inc., Toronto, Canada. This synthetic oligonucleotide can anneal with itself to yield

multimers thereof. When inserted into a BAmHi site as

Figure 23:
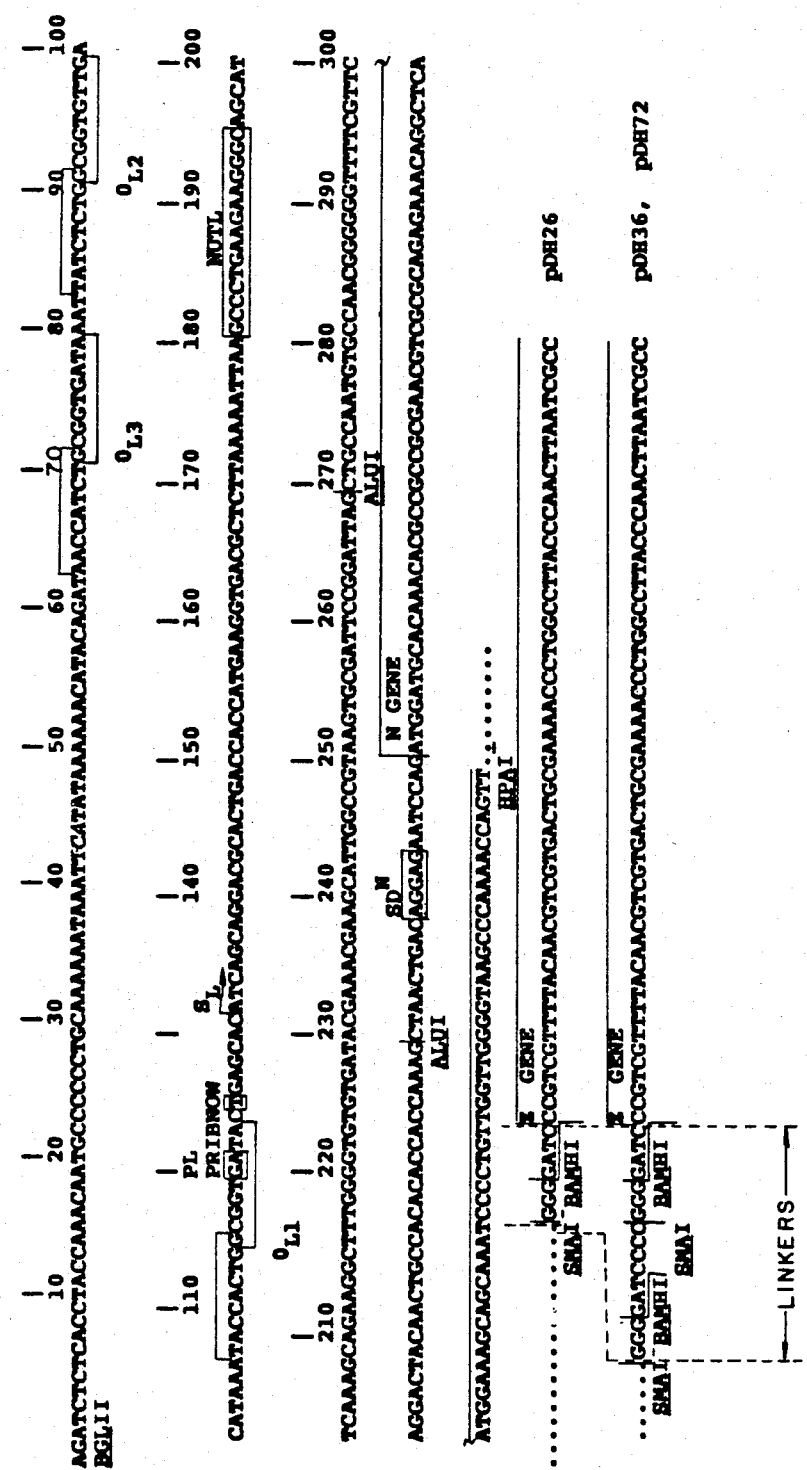
FIG. 23 represents the DNA sequence of the regions around the N-Z junction of recombinant plasmid pDH26 and recombinant plasmids pH36 and pDH72.

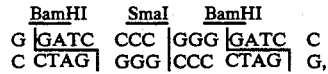

a BamHI site is regenerated at both ends of the adapter. If multimers go in, as usually happens, then cutting with SmaI and religating essentially reduces the inserted adapter to a single BamHI-SmaI-BamHI adapter.] Plasmid pDH72 (FIG. 22) is then created by simply cutting pDH36 with BglII, purifying the $P_L$-N-Z bearing backbone away from the $P_R$-cI857 segment (as in the isolation of pDH55) and then religating. Plasmids pDH26 and pDH36 were transformed into E. coli MC1000 at 30° C. and ampicillin-resistant colonies were selected on LB-amp plates. Plasmid pDH72 must be transformed into a λ-lysogen of E. coli and selected as ampicillin-resistant colonies on LB plates. The structures of pDH26 and pDH36 were confirmed by restriction enzyme analysis. Although the newly created DNA junctions were not sequenced, the nucleotide sequence of the regions around the HpaI-SmaI (N-Z) junction in pDH26 and in pDH36 and pDH72 should be as shown in FIG. 23.

5.10.2. Structure and Description of pDH26, pDH36 and pDH72 pDH26 and pDH36 are similar in that sub-segment a (about 2,844 b.p.; see FIG. 22), is from bacteriophage λ and includes the amino-terminal one-half of the N gene, the nutL site, the major leftward promoter-operator region ($P_L$-$O_L$), the rex gene, the cI gene (containing the cI857 and cIind⁻ mutations), the rightward promoter-operator region ($P_R$-$O_R$, and also prm) and the amino-terminal one-third of the cro gene. Sub-segment b (13 b.p.) present in pDH36, but not in pDH26, is a synthetic oligonucleotide carrying restriction enzyme cleavage sites BamHI-SmaI-BamHI. Sub-segments c (6,206 b.p.) and d (3,710 b.p.) are the same as sub-segments d and a, respectively, described for pMG101. Sub-segment e (356 b.p.) is the same as sub-segment c described for pJS55 and pDH55.

pDH72 is similar to pDH36 except that the BglII-rex-cI-cro-BglII segment is absent leaving segment a' (452 b.p.) containing only the N'-nutL-$O_L$-$P_L$ region (where N' indicates that only the amino-terminal portion of the N gene is present). Sub-segments b, c, d and e are identical to those described for pDH36.

In the absence of functional λ repressor, transcription from $P_L$ can be initiated and, in pDH26, can continue through the nutL site and N-Z fusion and probably also through the Y and A genes. Derepression of pDH26, like pDH55, kills the host cells. Derepression of pDH36 does not, however, probably due to a "polarity" phenomenon. Classically, polarity in the lac operon of E. coli was observed as the failure of lacZ amber mutants to produce lac permease although the cells were genotypically lacY⁺. The current understanding of polarity is that failure to translate the lacZ gene to its natural carboxy-terminal end allows transcription termination functions to become effective downstream of the lacZ amber mutation such that lacY is not transcribed efficiently. Such could be the case in pDH36, since translation of the N portion of the fusion continues into lacZ out of phase and reaches UGA and UAA nonsense codons very early in the gene ensuring cessation of Z translation. Failure to translate Z mRNA (in any phase) should lead to transcription termination in the same way lacZ amber mutations lead to transcription termination. To the extent that high level $P_L$-directed transcription in pJS55, pDH55, and pDH26 is responsible for the lethality at a primary level, failure to translate lacZ mRNA in pDH36 should allow termination of transcription and should be responsible for its non-lethality. Like pJS55 and pDH26, pDH36 carries the cI857 repressor that allows controlled derepression by a temperature shift to 39°–42° C. Like pDH55, pDH72 can be grown and maintained in cells carrying either the cI+ or cI857 alleles.

5.10.3. Use of Plasmids pDH26, pDH36 and pDH72 as Cloning Vehicles

Plasmids pDH26, pDH36 and pDH72 allow cloning and high level expression of gene segments cloned into the SmaI or BamHI sites between the N and lacZ segments. The cloned segment is transcribed as part of the N-lacZ fusion. If the cloned segment fortuitously contains transcription termination signals, N protein can be supplied in trans using the proper host to overcome such potential transcriptional blocks.

One main advantage that pDH36 and pDH72 provide over the pJS55 and pDH55 plasmids is that when cloned segments are fused in phase with the N coding segment and with the Z coding segment, a triple fusion protein is produced. Such a fusion exhibits β-galactosidase activity and the clones are deep blue on XG-amp plates, while colonies carrying plasmids without inserts are pale blue or white. [As with in-phase derivatives of pMG101 that over-produce lac permease, pDH26 and any in-phase derivatives of pDH36 and pDH72 should prevent cell growth in the presence of lactose. Therefore, only XG-amp plates can be used as the primary indicator of β-galactosidase production; see Section 5.3.3.] A further consequence of having an insert in phase at both ends is that the sparing effect of polarity in pDH36 and pDH72 discussed above no longer exists, and such producing cells die for that reason. Thus, if pDH36 is used as a primary cloning vehicle, as in shotgun cloning experiments, (a) a transcription termination signal must be placed downstream of the Z gene to prevent transcriptional lethality (see Section 5.8.4.), (b) expression must be held at intermediate levels by only partial derepression (by temperature manipulation), or (c) a down-promoter mutation must be introduced to reduce the level of transcription to below the lethal threshhold (see Section 5.11.).

5.11. pDH428 and pDH438

5.11.1. Isolation of Plasmids pDH428 and pDH438

Figure 24A:
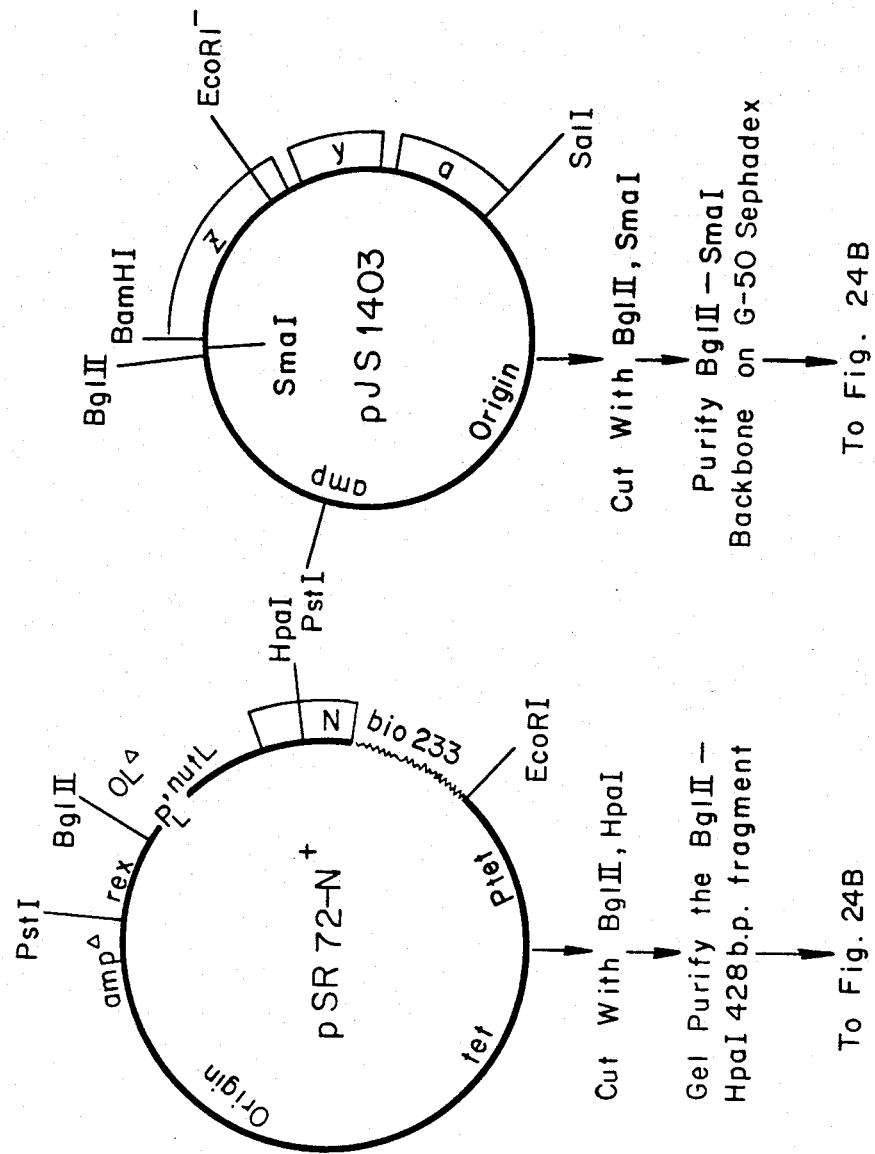
FIG. 24 depicts the steps taken to treat and recombine portions of recombinant plasmids pSR72-N$^+$ and pJS1403 in the construction and isolation of recombinant plasmid pDH428.
Figure 24B:
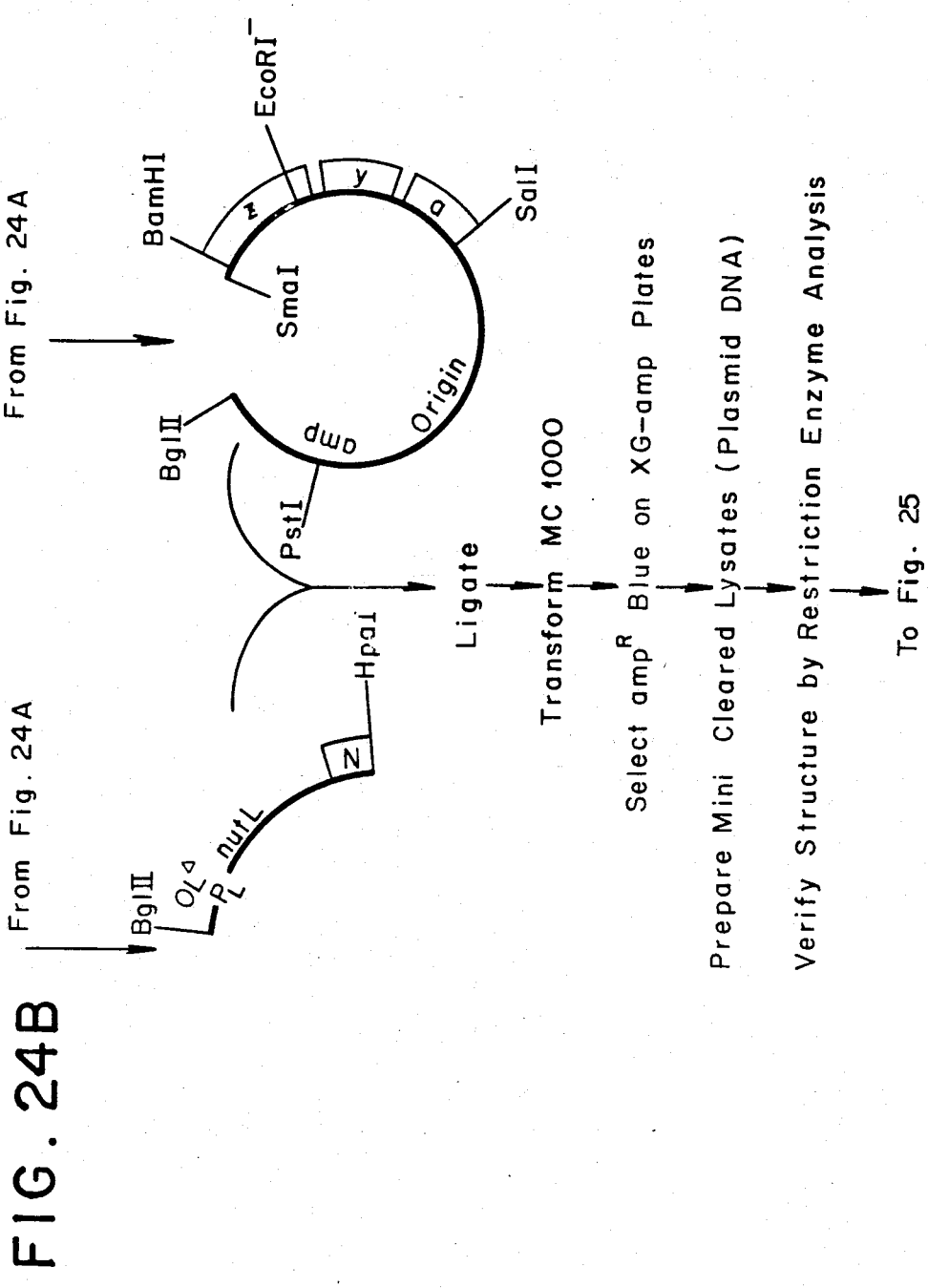
Figure 25:
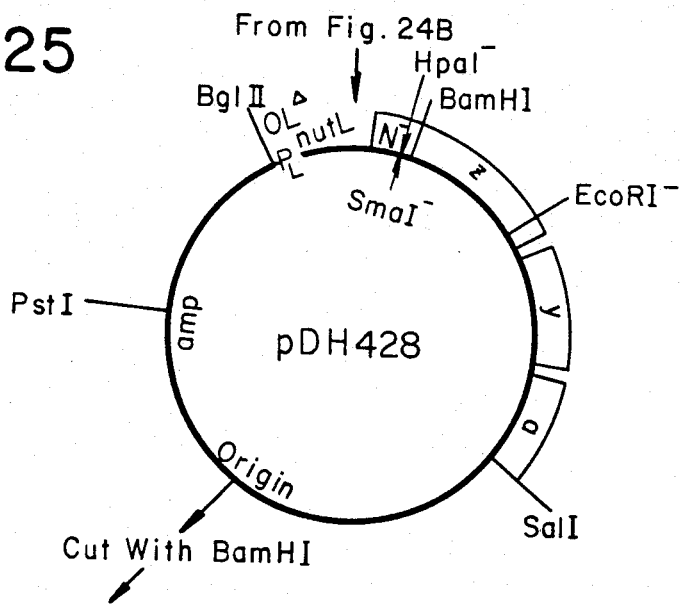
FIG. 25 is a schematic diagram of recombinant plasmid pDH428 and indicates the steps taken to convert pDH428 to pDH438.
Figure 25:
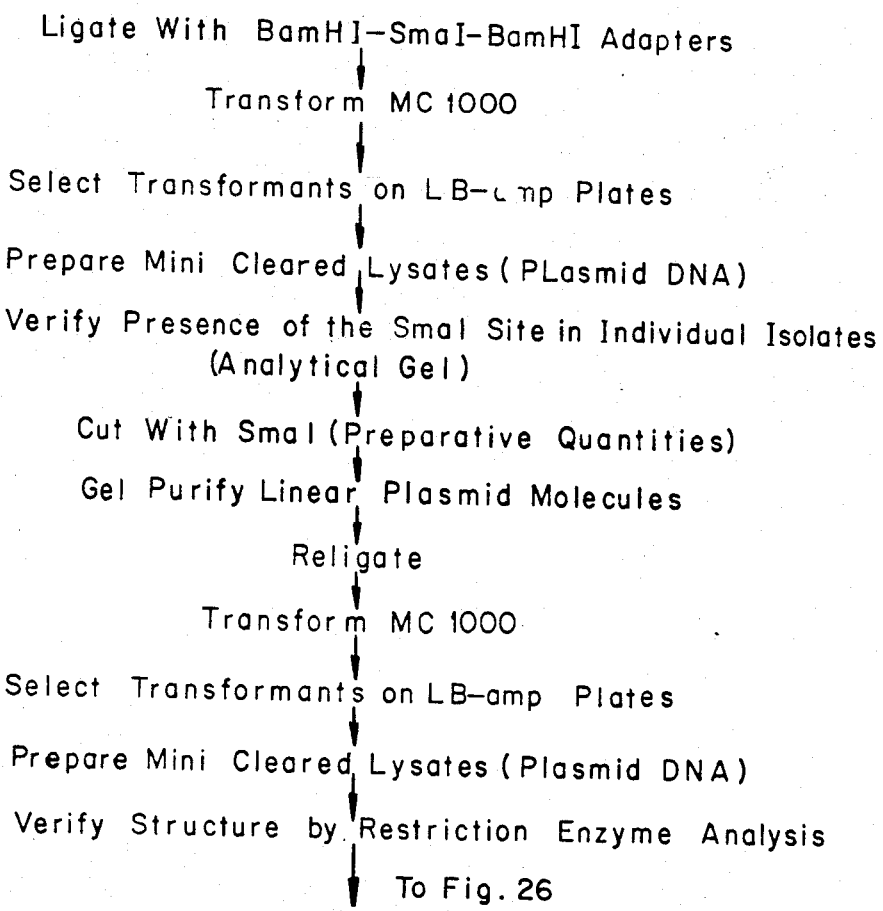
Figure 27:
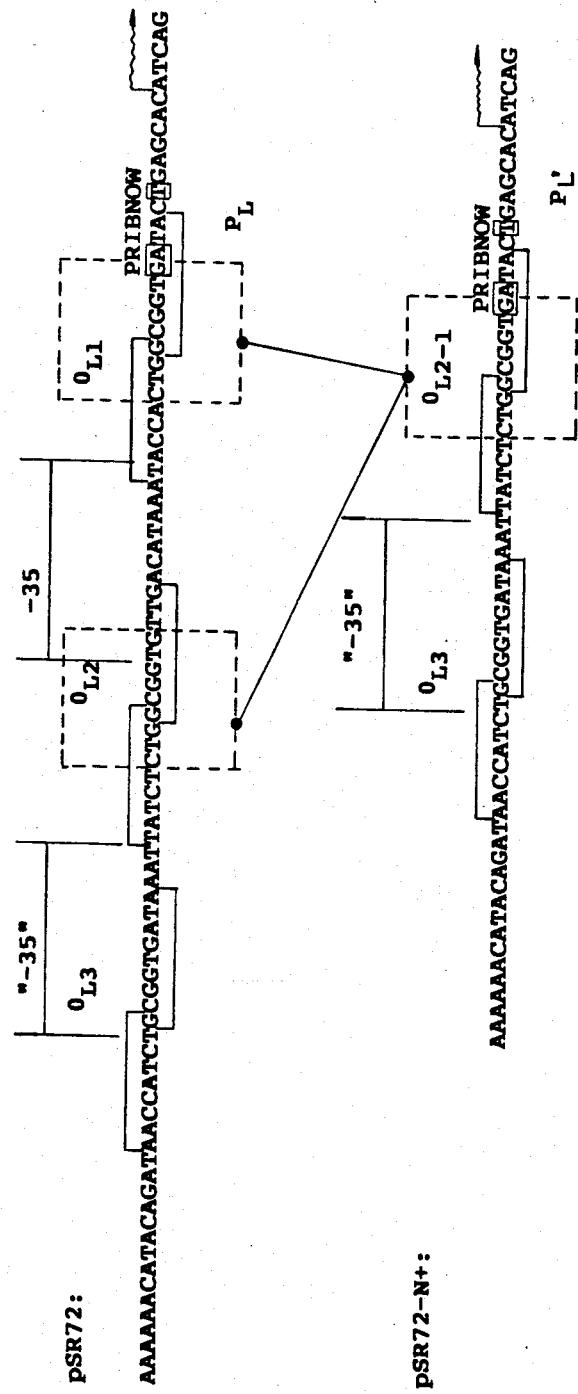
FIG. 27 represents the DNA sequence of the wild-type $O_L$-$P_L$ region from bacteriophage λ in recombinant plasmid pSR72 and the DNA sequence of the partially deleted $O_L$-$P_L$ region in recombinant plasmid pSR72-N$^+$.

Plasmid pDH428 was constructed by purifying the BglII-HpaI $P_L$-bearing fragment from pSR72-N+ (see FIG. 24) and ligating it into the BglII-SmaI backbone of pJS1403 (see FIGS. 24 and 25). Plasmid pSR72-N+ is a derivative of pSR7. Plasmid pSR7 was made by inserting the EcoRI fragment from λbio233cI857 carrying the bio-N-cI857-cro region [see Szybalski and Szybalski, Gene 19: 93-103(1982)] into the EcoRI site of pBR322 [Salstrom and Roberts (unpublished)]. When the PstI fragment carrying $amp^R$ and cI857 was removed from pSR7 and the backbone religated, a single isolate (out of about 300), pSR72-N+, was found to produce λN function constitutively. The $P_L$ promoter function in pSR72-N+ is impaired compared to that in pSR7 and in fact it is this feature that allows it (pSR72-N+) to survive in cells not expressing repressor function (see description of pDH55 in Section 5.9.2.). The sequence of the wild-type $O_L$-$P_L$ region present in pSR7 is shown in FIG. 27. The deleted segment in pSR72-N+ includes the normal −35 region (the initial recognition site for RNA polymerase in the promoter) of $P_L$. Such a deletion should normally knock out promoter function altogether. However, the region immediately upstream, replacing the −35 region in the mutant, is about 67% homologous with the deleted segment and serves as a functional −35 region in its new position with respect to $P_L$, albeit not as well as the wild-type −35 region. N function is produced by the plasmid indicating that the new promoter, $P_L$, does in fact function. Furthermore, the $O_{L2-1}$ hybrid operator that is generated by the deletion still functions as a repressor binding site and, together with $O_{L3}$, allows repression of N production by binding λ repressor.

Figure 26:
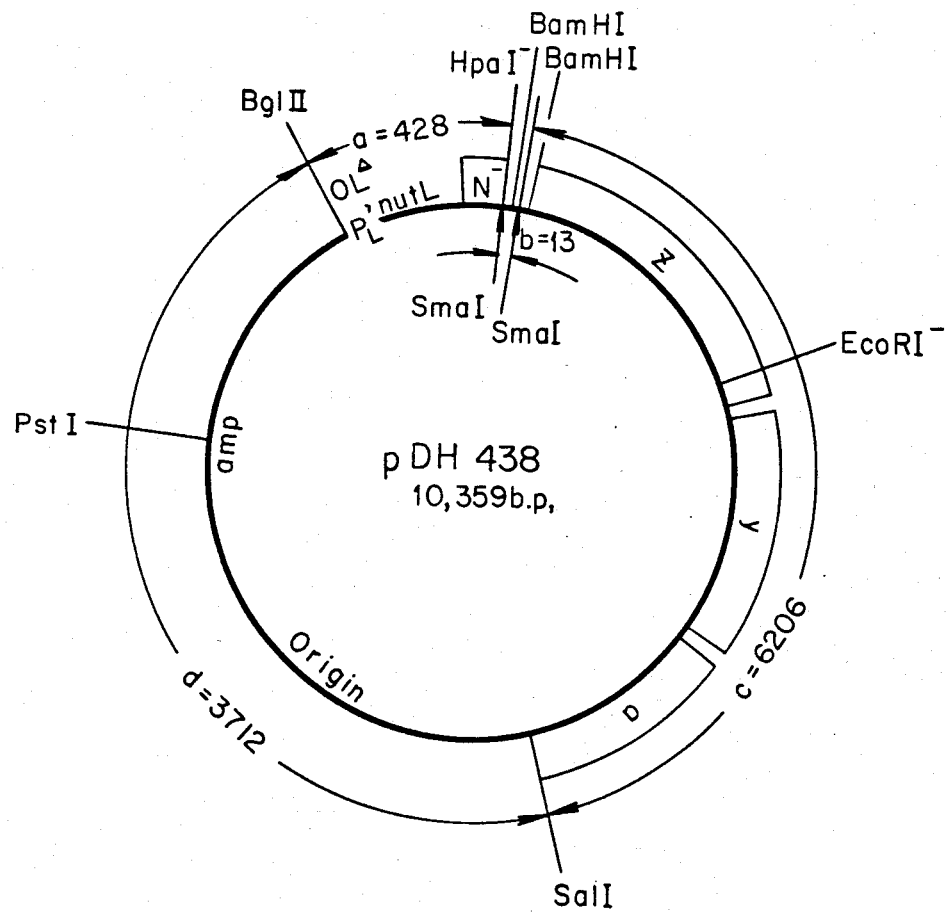
FIG. 26 is a schematic diagram of recombinant plasmid pDH438.

Plasmid pDH438 was created by inserting the BamHI-SmaI-BamHI synthetic oligonucleotide adapter (see Section 5.10.1) into the BamHI site of pDH428 to place the lacZ portion out of phase with respect to N (see FIGS. 25 and 26). To isolate plasmids pDH428 and pDH438, the respective ligation mixtures were each transformed into E. coli MC1000 and ampicillin-resistant colonies were selected on XG-amp plates. Minicleared lysates of E. coli MC1000 were prepared and the structures of the plasmids were verified by restriction enzyme analysis. Although the newly created DNA junctions were not sequenced, the nucleotide sequence of the regions immediately surrounding the HpaI-SmaI (N-Z) junction in pDH428 and in pDH438 should be exactly the same as that shown for pDH26 and for pDH36, respectively (see FIG. 23).

5.11.2. Structure and Description of pDH428 and pDH438

Plasmid pDH438 is shown in FIG. 26. Sub-segment a (428 b.p.) is from bacteriophage λ and includes the amino-terminal one-half of the N gene, the nutL site, and a mutant leftward promoter-operator region (see Section 5.11.1.). Sub-segments b (13 b.p.), c (6,206 b.p.) and d (3,712 b.p.) are identical to sub-segments b and c, respectively, in plasmids pDH36 and pDH72, except that the EcoRI end of d was converted to a BglII end (see Section 5.1.1. for isolation of pJS1403), resulting in a net gain of 2 bases, i.e., a loss of 4 bases followed by a gain of 6 bases. Plasmid pDH428 is identical to pDH438, except that sub-segment b in pDH428 is only 3 b.p. long, i.e., it lacks the synthetic oligonucleotide adapter insert, BamHI-SmaI-BamHI, present in pDH438.

In the absence of functional λ repressor, transcription from $P_L$ can be initiated and, in pDH428, can continue through the nutL site and N-Z fusion and through the Y and A genes. Unlike pJS55, pDH55 and pDH26, though, derepression of pDH428 is not lethal to the cells, since the promoter strength is reduced as explained above (see Section 5.11.1.). Therefore, the main advantage that pDH438 has over the pDH36 and pDH72 systems is that derepression of cloned segments that are in phase with the N and Z portions of the triple fusion do not automatically kill the host cells. The N stimulation and antitermination aspects of the $P_L$-nutL system are still intact.

5.12. pDH800 Series

The primary reason for harnessing the $P_L$-nutL system is that it is one of the strongest and most easily regulated promoter-operator systems currently known in E. coli or its phages. Not only is $P_L$ itself a very strong promoter, but N protein provided in trans to $P_L$-nutL stimulates $P_L$-directed transcription another 3-5 fold, and imparts to RNA polymerase the antitermination capacity. Since the $SD^{cro}$-$AUG^{cro}$ region of pJS413 stimulates production of high levels of cloned proteins, the pDH700 plasmid series and the pDH800 plasmid series were devised to combine the attributes of the $P_L$-nutL and of the $SD^{cro}$-$AUG^{cro}$ regions to achieve maximal expression vectors. In these plasmids, the $SD^N$-$AUG^N$ region of plasmids such as pJS55, pDH55, pDN55, pDH26, pDH36 and pDH72 is replaced by the $SD^{cro}$-$AUG^{cro}$ region of pDN599, an in-phase derivative of pJS413.

5.12.1. Isolation of pDN55

Plasmid pDH55 (see FIG. 28) was opened with BglII, filled in with DNA polymerase (Klenow fragment) and religated in the presence of SalI synthetic DNA linkers (octamer) to yield pDN55. Hence, the unique BglII site is converted to a SalI site. Plasmid pDN55 was transformed into a λ lysogen of E. coli MC1000 and ampicillin-resistant colonies were selected on LB-amp plates. Mini-cleared lysates of E. coli MC1000(λ) were prepared to isolate plasmid pDN55 DNA. The plasmid structure was verified by restriction enzyme analysis.

5.12.2. Isolation of the pDH500 Series

Figure 29:
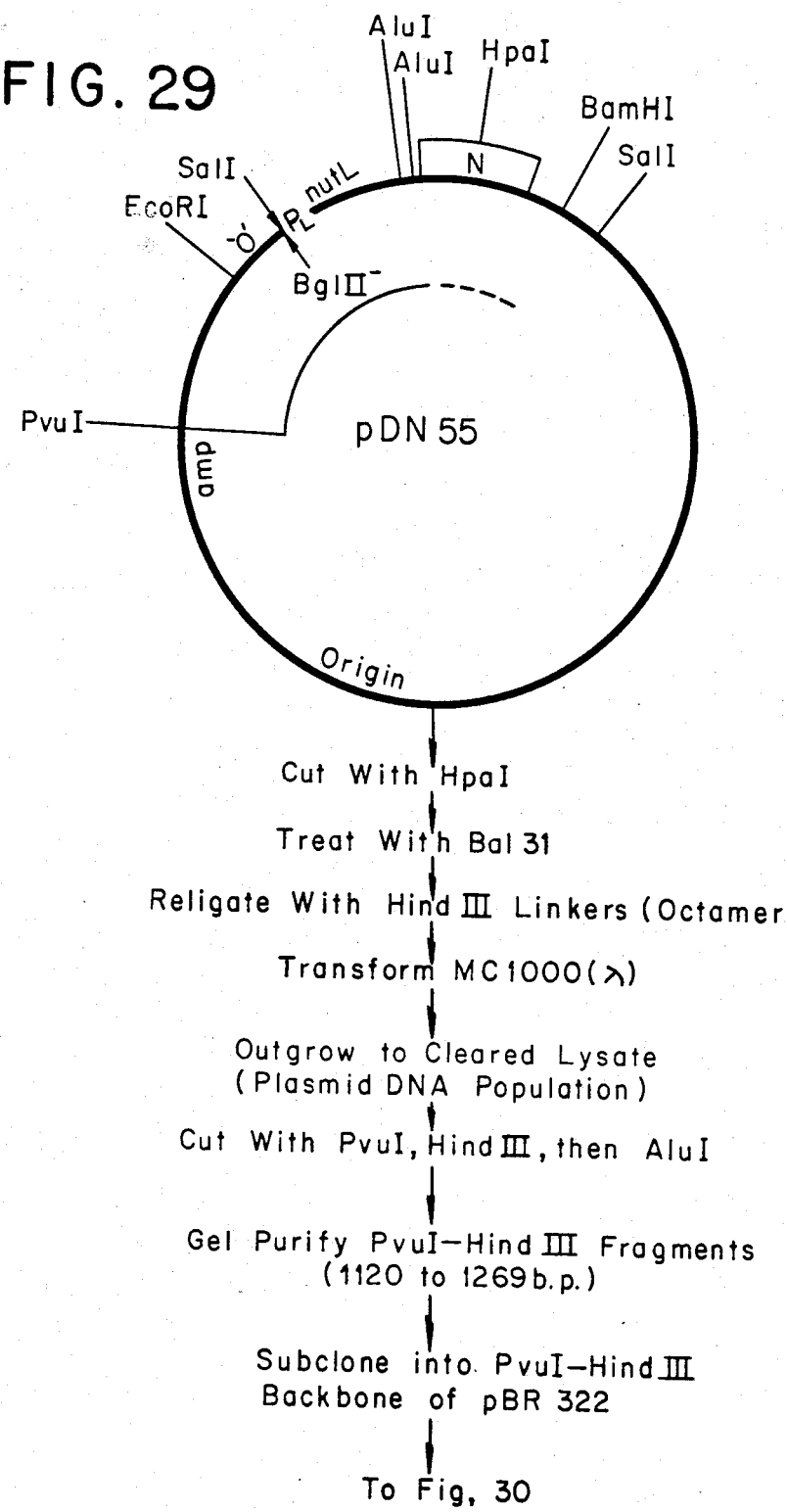
FIG. 29 is a schematic diagram of recombinant plasmid pDN55 and indicates the steps taken to convert pDN55 to the pDH500 series.
Figure 30:
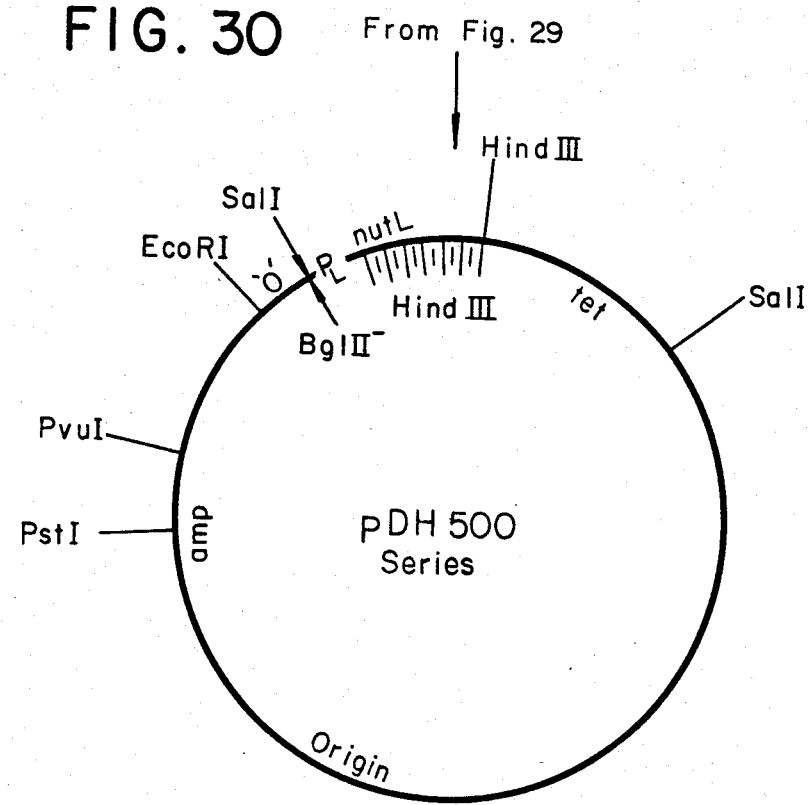
FIG. 30 presents a schematic diagram of the pDH500 series and the PstI-HindIII fragment population excised therefrom.
Figure 30:
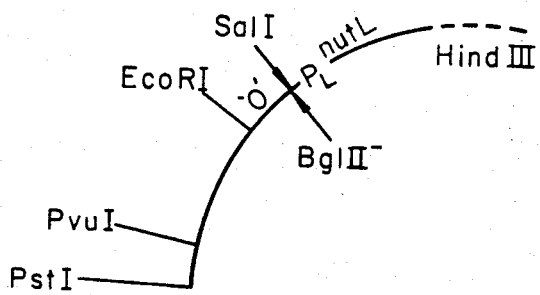

The pDH500 series was produced by introducing a unique HindIII site at various positions downstream of $P_L$-nutL. Plasmid pDN55 was opened at the unique HpaI site within the N gene, treated with Bal31 and religated in the presence of HindIII synthetic DNA linkers. The PvuI-HindIII fragment population (see FIG. 29) was purified and subcloned into the PvuI-HindIII backbone of pBR322 as follows: after digestion with PvuI and HindIII, the population was sub-cut with AluI to remove the HindIII end from all fragments bearing the HindIII linker at sites beyond the AluI sites between nutL and N (see FIG. 29). This limits the fragment population that can be sub-cloned into the PvuI-HindIII backbone to those no longer than 1,269 b.p. This was verified by cutting isolates with PstI and HindIII and observing fragments no greater than 1,389 b.p. (see FIG. 30) and by cutting with HincII and HindIII and observing fragments no greater than 175 b.p. in length. Many individual isolates were characterized to obtain a series of plasmids with the HindIII site located at many different positions (due to the randomness of Bal31 nuclease digestion) downstream of $P_L$ (see FIG. 30). The mixture of pDH500-type plasmids was retained for use in isolation of the pDH700 series.

5.12.3. Isolation of the pDH600 Series

The pDH600 series is characterized by the introduction of a unique HindIII site upstream of $SD^{cro}$ in plasmid pDN599. The latter is from the pJS413 croΔ series (see Section 5.2.4. and FIG. 31) and was linearized by partial digestion with EcoRI, treated with Bal31 and religated in the presence of HindIII synthetic DNA linkers. The resulting plasmid DNA population was then subjected to HindIII digestion and the HindIII linear molecules were gel purified.

Following religation, the HindIII+ plasmid DNA population was transformed back into MC1000 to obtain a population of plasmids (pDH600 series). The transformation outgrowth culture was (a) plated on Mac-lac-amp plates for individual (white) transformants for characterization and use in construction of the pDH700 series, and (b) grown further and amplified as a population for purification of large amounts of a mixed polulation of plasmid DNA, also for use in construction of the pDH700 series. Red transformants from (a) above are enriched for plasmids that have lost the EcoRI site upstream of Plac during the Bal31 treatments, but have retained the elements of Plac. Because ligation of the Bal31 treated linears was carried out in the presence of HindIII linkers, a HindIII site was introduced in place of the EcoRI site, thus removed.

5.12.4. Isolation of the pDH700 Series

Figure 31A:
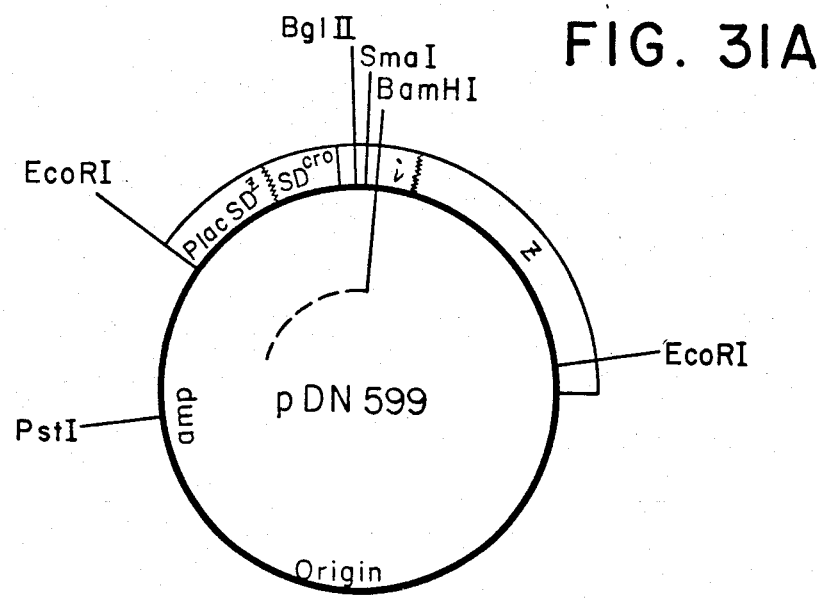
FIG. 31 depicts the steps taken to convert recombinant plasmid pDN599 to the pDH600 series and to isolate the PstI-HindIII backbone population from the latter.
Figure 31A:
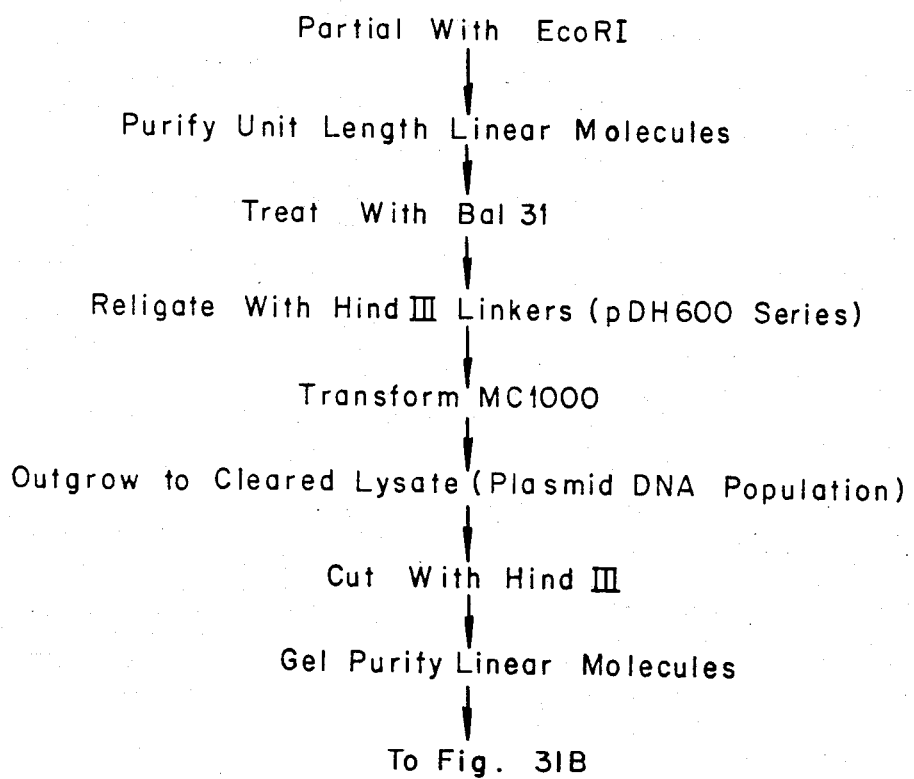
Figure 31B:
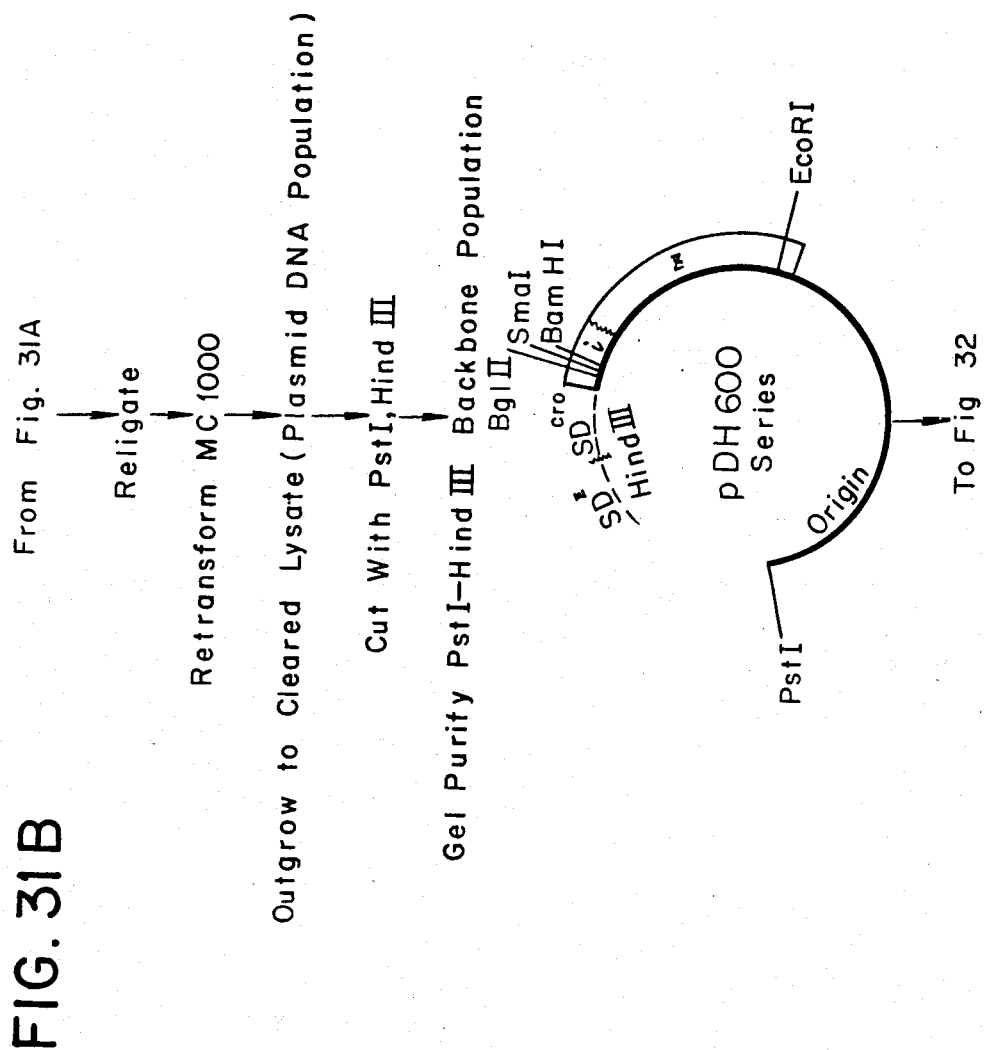
Figure 32:
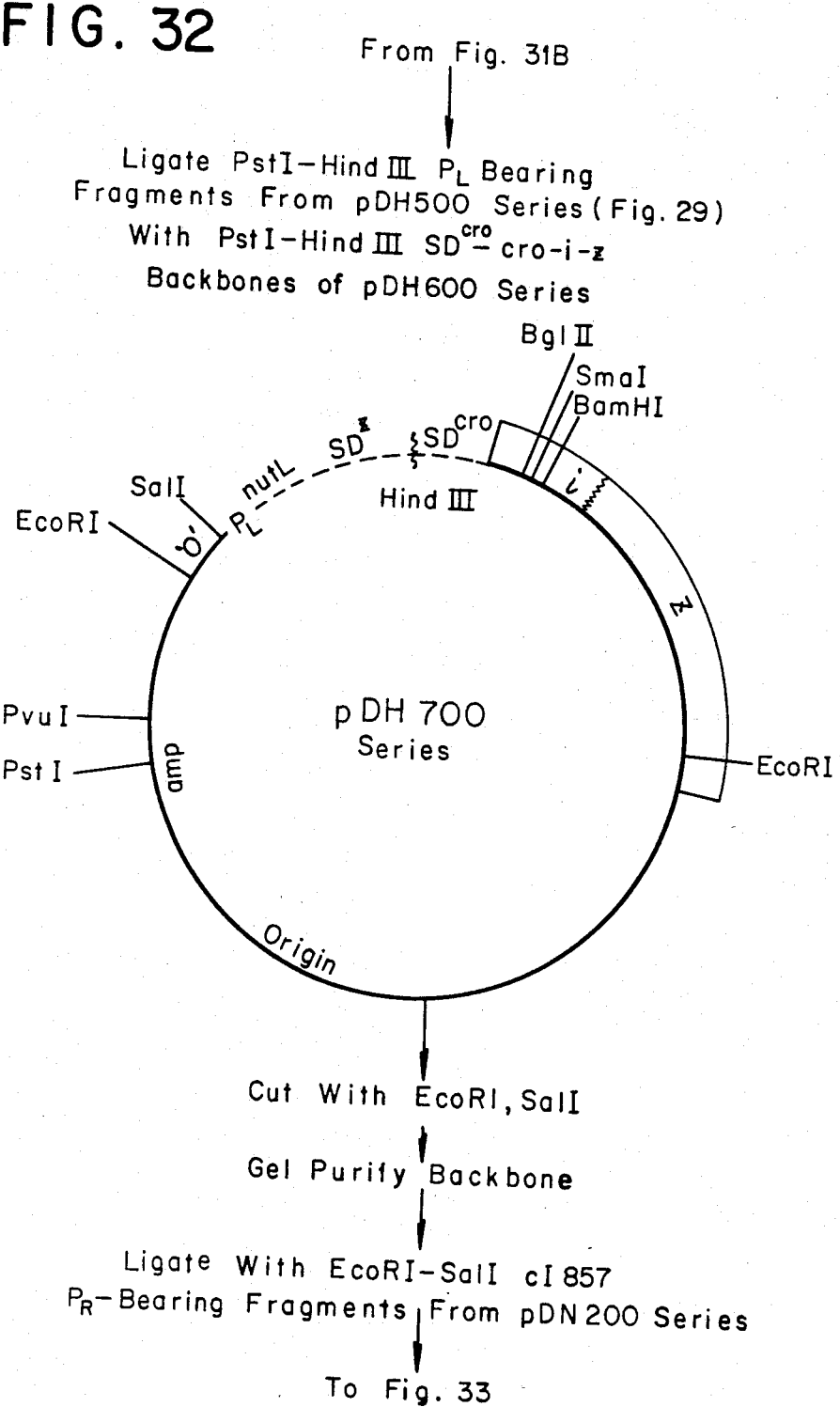
FIG. 32 is a schematic diagram of the pDH700 series and indicates the steps taken to construct the pDH700 series from the pDH500 and pDH600 series and to convert the pDH700 series to the pDH800 series.

Individual isolates of the pDH600 series, or a discrete mixed population of isolates of the pDH600 series, were fused with members of the pDH500 series via their unique HindIII sites (Pst-HindIII $P_L$-nutL fragments from the pDH500 series ligated into the PstI-HindIII backbones of the pDH600 series) as shown in FIGS. 31 and 32 to generate $P_L$-cro fusions (pDH700 series). Plasmids that exhibited extraordinary translational capacity were identified in MC1000(λ), in which transcription is largely but not completely repressed by λ repressor, by their production of enough β-galactosidase to cause the red colony phenotype on Mac-lac plates. Additionally, the PstI-BglII $P_L$-cro fusion fragment population was excised from the pDH700 series (see FIG. 32) and reinserted into the PstI-BglII backbone of pDN599am. The ligation mixture was transformed into E. coli MC1000 not containing the prophage. pDN599am is identical to pDN599 except that it has an XbaI linker (5'-TCTAGA-3') inserted at the SmaI site such that the UAG (stop codon) is in phase with cro and I-Z thereby preventing efficient synthesis of the cro-I-Z fusion protein (see Section 5.2.5.). Such $P_L$-cro derivatives of pDN599am are non-lethal in MC1000 due to the polarity phenomenon (see Sections 5.9.2. and 5.10.2.) created by the UAG nonsense codon even though transcription *initiation* is very strong. Compared to the non-amber containing plasmid constructions very little β-galactosidase is synthesized and results only from the rare insertion of some amino acid at the UAG codon (see Section 5.2.5.). If such an insertion occurs at some relatively fixed frequency or efficiency, then the synthesis of β-galactosidase should be proportional to the strength of translation initiation from the $P_L$-cro transcript. If particular $P_L$-cro fusions are extraordinarily prone to translation initiation and the resulting β-galactosidase activity is high enough to exhibit the red color on Mac-lac plates, then such fusions can be selected by this method, and in fact may red isolates were obtained. However, to the extent that high efficiency translation across the UAG codon reduces polarity, transcription beyond I-Z could approach the lethal level. This could place an upper limit on the translation efficiency of the plasmid that can be attained by this type of fusion that is below the maximum ordinarily tolerated by the cell. However, by combining this approach with a modification of the method using MC1000(λ) in which the prophage (λNam7am53cI857-cro27Pam3) synthesizes the cI857 temperature-sensitive repressor, such high efficiency translation fusion plasmids could be obtained and identified. In this case, temperatures between 30° and 42° C. allow a continuous range of repression-depression to allow growth and characterization of the extremely high level translation fusion plasmids. The XbaI site can be easily removed from such plasmids to permit translation to proceed unimpeded beyond the position of the UAG nonsense codon.

5.12.5. Isolation of the pDH800 Series

The pDH800 series is characterized by the insertion of a cI857-$P_R$ segment into individual members of the pDH700 series. The EcoRI-SalI cI857-$P_R$ fragment from selected isolates from the pDN200 (pDN455 cro$\Delta$) series, in which the deletions are so extensive as to be missing the SD-AUG-cro coding sequence, but not the startpoint for $P_R$-initiated transcription, is purified and inserted into the EcoRI-SalI backbones of pDH700 isolates (FIG. 32) to provide the temperature-sensitive $\lambda$ repressor to the plasmid for tighter regulation of $P_L$-directed expression.

5.12.6. Structure and Description of pDH800 Series

Figure 33:
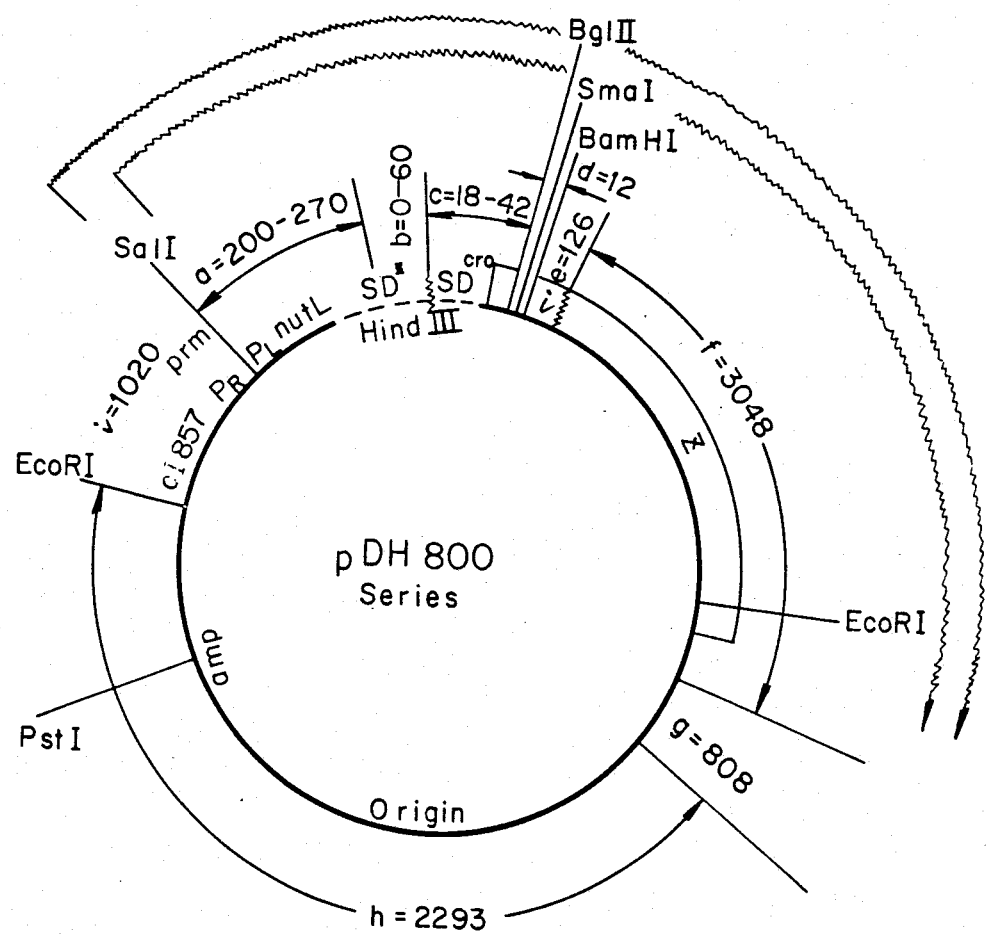
FIG. 33 is a schematic diagram of the pDH800 series. For an explanation of the lettered segments, see Section 5.12.6.

A schematic diagram of the pDH800 series is shown in FIG. 33. Sub-segment a (200 to 270 b.p.) is from bacteriophage $\lambda$ and includes the leftward promoter-operator region ($P_L$-$O_L$) and the leftward site of N utilization, nutL. Sub-segment b (0 to 60 b.p.) is from the lac operon of E. coli and includes the $SD^Z$ segment and its environs and is included in one set of plasmids. Sub-segment c (18 to 42 b.p.) is from bacteriophage $\lambda$ and includes the cro SD-AUG region and, is some isolates, part of the rightward promoter-operator region ($P_R$-$O_R$) which would be non-functional here as in pJS413. Sub-segments d, e, f, g, and h are identical to sub-segments d, e, f, g, and a respectively from pJS413. Sub-segment i (about 1020 b.p.) is from bacteriophage $\lambda$ and includes the cI gene carrying the cI857 and ind$^-$ mutations, and the rightward promoter-operator region, $P_R$-$O_R$, oriented in the same direction as $P_L$-$O_L$.

The contiguous sub-segments i, a, b, c, d, e, and f comprise a hybrid operon driven by dual promoters $P_L$ and $P_R$ and regulated by a single repressor. The operon has the benefit of the N antitermination system regulated by nutL. Translation of the cro-I-Z segment is controlled at least by the $SD^{cro}$, and perhaps also by $SD^Z$. The general attributes of all the above elements have been described in other sections.

5.12.7. USE OF pDH800 PLASMIDS AND ITS DERIVATIVES AS CLONING VEHICLES

Plasmids in the pDH800 series can be used as generally described for the other plasmids. The cloning sites are BglII, SmaI and BamHI, but additional sites can be added or substituted. The cro-I-Z fusion is in phase from the beginning of cro to the end of Z, however. Therefore, to use as a shot-gun cloning vehicle in the manner described for pJS413, either of the following two phase adapters, for example, could be inserted into the BglII-SmaI backbone to generate cro-I-Z fusions that are out of phase:

Such derivatives can provide the other two phases of the cloning sites with respect to cro for direct cloning experiments. The other two phases of BamHI with respect to the I-Z portion can be obtained by using the backbones containing the BamHI phase adapters described in the construction of pHK412 and pHK414. The EcoRI mutation can be introduced into the lacZ gene in the manner described in Section 5.2.2.

6. EXAMPLES

The methods described in this section were used to construct plasmids pJS413, pMG101, pJS400, pDN455, pDH55, pDN55, pDH26, pDH36, pDH72, pDH428, pDH438 and the pDH500, pDH600, pDH700, and pDH800 series, and derivatives and are generally applicable to the construction of other cloning and expression vehicles. The methods include protocols for transforming E. coli with the constructed plasmids and preparing batches of plasmids for cloning and for structure verification by restriction enzyme analysis and DNA sequencing. The order in which these protocols and procedures were followed for each plasmid is discussed in Section 5 and indicated in the corresponding figures.

6.1. CONDITIONS FOR RESTRICTION ENZYME DIGESTION

Enzymes used for restriction digestion were supplied by New England Biolabs, Beverly, Mass., Bethesda Research Laboratories, Rockville, Md. or Biotech, Inc., Madison, Wis. Typically, reaction mixtures contained 0.2-1.0 @g DNA in 10 @l of suitable restriction buffer to which an appropriate amount of enzyme had been added. The compositions of low, medium, and high salt concentration buffers are shown in Table II; enzymes are listed according to preferred restriction buffers in Table III.

TABLE II

| | Restriction Buffer Compositions | | |
|---|---|---|---|
| Component | Low Salt (mM) | Medium Salt (mM) | High Salt (mM) |
| Tris, pH 7.4 | 10 | 6.6 | 6.6 |
| Magnesium Chloride (MgCl$_2$) | 10 | 6.6 | 6.6 |
| Potassium Chloride (KCl) | 20 | — | — |
| Sodium Chloride (NaCl) | — | 60 | 150 |
| $\beta$-Mercaptoethanol | 10 | 6.6 | 6.6 |

TABLE III

| Preferred Restriction Buffers for Enzymatic Digestion | | |
|---|---|---|
| | Buffer: | |
| Low Salt | Medium Salt | High Salt |
| Enzyme: SmaI | BglII | BamHI |
| HpaI | PstI | PvuI |
| | EcoRI | SalI |
| | PvuII | |
| | HindIII | |
| | AluI | |

Restriction digestions were run at 37° C. for 15-60 minutes. Reactions were stopped by heating the mixtures for 10 minutes at 70° C.

6.2. DNA Modification

6.2.1. Modification of DNA Fragments with BAL31 Nuclease

Bal31, (Bethesda Research Laboratories, Rockville, Md.), a nuclease capable of simultaneously and continuously removing the 3' and 5' -termini of double-stranded DNA, was used to shorten DNA fragments as one of the steps in the construction of plasmids of the pJS413 cro$\Delta$ series, the pDN200 series, the pDH500 series, the pHD600 series and pDH322. (See Sections 5.2.4., 5.8.2., 5.12.2., 5.12.3., and 5.2.3., respectively).

After restriction enzyme digestion, 1–2 μg of linear plasmid DNA was combined with an appropriate amount of Bal31 (about 0.2 units, where one unit of activity is defined as that amount of enzyme that releases 1 μg of acid soluble nucleotide in 1 minute at 30° C.) in 50 μl reaction mixtures containing: 12 mM calcium chloride, 12 mM magnesium chloride, 600 mM sodium chloride, 20 mM Tris (pH 8.1), 1 mM EDTA and 0.65 mg/ml heat-denatured calf thymus DNA. Samples were incubated at 30° C. and were removed at various time points between 0 and 10 minutes. Reactions were stopped by adding EDTA, pH 8.0, to 50 mM and placing the mixtures on ice. Next, the samples were diluted about 2-fold in double-distilled water prior to the addition of 2–3 volumes of 100% ethanol. The DNA was allowed to precipitate from solution by placing the samples in a dry ice-ethanol bath for 15 minutes; the samples were then centrifuged in Eppendendorf tubes for 10 minutes.

The extent of Bal31 nuclease digestion in each sample was determined by running the reaction mixtures on 7.5% polyacrylamide gels at 150 volts with appropriate DNA size markers. Sometimes it was necessary to sub-cut with restriction enzyme before gel electrophoresis to increase the sensitivity of the assay. The remainder of the digest was used for subsequent ligations.

6.2.2. Modification of DNA Fragments with S1 Nuclease

S1 nuclease treatments were performed on DNA fragments generated during the construction of plasmids pJS413 (Section 5.1) and pDN455 (Section 5.7). The method was used to remove single-stranded DNA from the ends of double-stranded fragments resulting from restriction digestions. The procedure following was that of Roberts et al. [Proc. Natl. Acad. Sci., U.S.A. 76(2): 760–764 (1979)].

6.2.3. Modification of DNA Fragments with DNA Polymerase I

Linear DNA fragments having 5' protruding ends resulting from cleavage with certain restricton enzymes, for example, BglII, HindIII, EcoRI, etc., were rendered blunt using DNA polymerase I (Klenow fragment). The reaction mixture typically contained about 5.0 pmoles DNA in: 67 mM Tris-HCl, pH 7.4, 67 mM sodium chloride (NaCl), 7.0 mM magnesium chloride ($MgCl_2$), together with the four nucleoside triphosphates at 50 μM each and 4 units of DNA polymerase I in a total volume of 200 μl. This mixture was incubated on ice for 15 minutes.

6.2.4. Modification of DNA Fragments with Synthetic Oligonucleotide Linkers and Adapters After S1 nuclease treatment, Bal31 treatment, or other modification of the ends of linear DNA molecules to render them blunt, various synthetic oligonucleotide linkers (phosphorylated) were ligated to DNA fragments used for the construction of plasmids pJS1403, pDN455, pDN55, the pDH500 series and the pDH600 series and derivatives thereof (see Sections 5.1.1., 5.7.1., 5.12.1., 5.12.2., and 5.12.3., respectively). For example, a BglII linker, 5'-dCAGATCTG-3' (phosphorylated; from Biologicals, Inc., Toronto, Canada), was ligated into a former EcoRI site of pMC1403 that had been rendered blunt by S1 nuclease to yield pJS1403 (see Section 5.1.1.).

Additionally, various synthetic oligonucleotide adapters (phosphorylated) were ligated into specific restriction sites in certain plasmids to expand an already-existing linker or to simply exchange one linker for another already present in the plasmid. For example, in the contruction of pHK413 the BglII-SmaI segment in pJS413 was removed and a BglII-HindIII-SmaI segment (adapter) was inserted (see Section 5.2.1.). Typically, these ligation reaction mixtures contained the following components in a 25 μl volume: 1 pMole linker or adapter 1× ligase buffer, 1 mM ATP, 1 μl T4 DNA ligase and 400–500 ng (approximately 0.02 to 0.05 pMoles) linear plasmid DNA. The reaction was run under conditions generally used for other ligations as described in the next section. Since multiple linkers or adapters are ligated into a site in tandem, the ligation mixture, or the DNA produced following outgrowth and cleared lysate preparation, is cut with an excess of the restriction enzyme to "reduce" the linker or adapter to a monomer. Following religation of the linear molecules thus produced the plasmids are retransformed into an appropriate host and grown up for large scale DNA preparation.

6.3. LIGATIONS

In a final volume of 20–50 μl, 10 ng/μl of linearized vector DNA plus a 1- to 100-fold molar excess of insert DNA were mixed. [If the DNA had complementary overhang, it was necessary to melt and reanneal before ligating, i.e., the DNA, in minimal volume (5–15 μl), was heated to 65° C. for 30 minutes in 1 mM EDTA, pH 7.5, and 200 mM NaCl. The annealing mixture was cooled at room temperature for approximately 60 minutes.] The final volume was made up such that the linearized vector and insert DNA were ligated in 20 mM Tris, pH 7.8, 10 mM magnesium chloride, 60 mM β-mercaptoethanol and 1 mM ATP. To this mixture, 1 μl of T4 DNA ligase (New England Biolabs at $4 \times 10^2$ units/μl or Biotec at $4 \times 10^1$ units/μl) was added. The reaction was run at room temperature for 4–24 hours.

6.4. TRANSFORMATION

*Escherichia coli* MC1000 [Casadaban and Cohen, J. Mol. Biol. 138: 179–207 (1980)] was transformed with plasmid DNA or DNA ligation mixtures by a modification of the method of Gautier and Bonewald [Molec. Gen. Genet. 178: 375–380 (1980)]. A sample of an overnight culture of *E. coli* MC1000 was diluted 100-fold into fresh Luria-broth (L-broth) containing appropriate antibiotics (e.g., ampicillin, chloramphenicol, kanamycin, mercury, spectinomycin and tetracycline) and allowed to grow to an optical density of 0.5 at 600 nm. Two milliliters of culture were used per transformation. The *E. coli* cells were centrifuged in a Beckman TJ6 centrifuge at 6,000 rpm for 10 minutes. Pellet fractions were resuspended in one-half the original volume in sterile, cold buffer of the following composition: 10 mM morpholinopropane-sulfonic acid (MOPS), pH 7.0, [Sigma Chemical Co., St. Louis, Mo.] and 10 mM ultrapure rubidium chloride (RbCl) [Alfa Division of Ventron, Danvers, Mass.] and centrifuged as above. Pellet fractions were resuspended in sterile, cold buffer (again in one-half the original volume), containing 100 mM MOPS, pH 6.5, 10 mM RbCl and 50 mM calcium chloride ($CaCl_2$); the cell suspension was held on ice for 30 minutes and centrifuged again. The resulting pellet fractions were resuspended in one-tenth the original volume (200 μl per transformation) in the cold, sterile buffer of composition: 100 mM MOPS, pH 6.5, 10 mM RbCl and 50 mM CaCl$_2$.

To transform *E. coli* cells, 200 μl of cell preparation, 3 μl dimethylsulfoxide (DMSO) (1.5%), and approximately 200 ng of plasmid DNA or DNA ligation mixture were combined and mixed in Eppendorf tubes. The tubes were placed on ice for 30–60 minutes to allow DNA adsorption. The mixtures were heat-pulsed at 42° C. for 2 minutes and allowed to stand at room temperature for approximately 10 minutes.

The entire adsorption mixtures were diluted into 5 ml of L-broth (10% tryptone, 5% yeast extract and 5% sodium chloride), and were allowed to outgrow for a period of 60 minutes, at either 30° C. or 37° C., after which time they were refrigerated. These mixtures were diluted appropriately, if necessary, and 0.1 ml aliquots were spread on nutrient agar plates containing required additives. For example, ampicillin was included in the plating medium when selection strategies called for the selection of ampicillin-resistant transformants.

6.5. PREPARATION OF MINI CLEARED LYSATES

To isolate small-scale preparations of plasmid DNA from *E. coli* host cells for DNA analysis, a modification of the method of Clewell and Helinski [Biochem. 9(22): 4428–4440 (1970)] was employed. A culture of *E. coli* was grown to an optical density (OD$_{600}$) of 0.5 in M9-broth to which 150–200 μg/ml of chloramphenicol (Sigma Chemical Co.) had been added for plasmid amplification. Five ml samples were centrifuged at 8,000 rpm for 10 minutes to pellet the cells. Care was taken to keep the samples cold. Pellet fractions were resuspended in 150 μl of cold prelysing solution (25% sucrose in 0.05 M Tris, pH 8.0).

The 150 μl cell suspensions were transferred to Eppendorf tubes to which the following components were added sequentially: 50 μl of 5 mg/ml lysozyme in 0.25 M Tris, pH 8.0; 50 μl of cold 0.25 M EDTA, pH 8.0; and 250 μl of cold lysing solution containing 1% Brij 58 (polyoxyethylene cetyl alcohol), 0.4% sodium deoxycholate (DOC), 0.0625 M Na$_2$EDTA, 0.05 M Tris, pH 8.0. After the addition of the lysozyme solution, the mixtures were allowed to stand on ice for 15 minutes before the EDTA solution was added. Similarly, a 15 minute interval of standing on ice was allowed between the addition of the EDTA solution and the cold lysing solution. The final mixtures were mixed gently and immediately and were allowed to stand for 60 minutes on ice.

The Eppendorf tubes were spun for 30 minutes in a microfuge located in a cold room at 4° C. The host DNA (pellet fraction) was removed as a gelatinous clump with an automatic micropipetter. It was necessary to pull gently, dragging the clump up the side of the tube.

The remaining supernatant fraction, containing plasmid DNA, was extracted 3 times with phenol (150–400 μl) which had been equilibrated with TE buffer, pH 8.0 (10 mM Tris, pH 8.0, and 1 mM EDTA, pH 8.0). For each extraction, the aqueous DNA layer was drawn from the top, leaving the phenol layer behind. Extracts were ethanol precipitated with one-ninth volume 3 M sodium acetate (NaAc), 0.1 M magnesium acetate (MgAc) plus 2–3 volumes of cold ethanol; they were stored overnight at −20° C. or placed in a dry ice-ethanol bath for 10–15 minutes.

After spinning the Eppendorf tubes for 15 minutes in a cold microfugre, supernatant fractions were decanted and pellet fractions were washed with 100% ethanol. The tubes were centrifuged for 15 minutes, if necessary, and again decanted. Pellet fractions were dried in a centrifugal freeze dryer for 10–20 minutes and then dissolved in 50 μl NE buffer (5 mM sodium chloride in 0.1 mM EDTA, pH 8.0). The dissolved pellet fractions were run over 1.5 ml G-50 columns to retrieve the plasmid DNA free of small molecule contaminants. This procedure, which added approximately 100 μl to the final volume, was performed as follows. Automatic pipetter pink tips (Sarstedt No. 70.770) were plugged with siliconized glass wool and placed in 4 ml polycarbonate tubes (Sarstedt No. 55.476). Approximately 1.5 ml of G-50 (Pharmacia Fine Chemicals AB, Uppsala, Sweden) slurried in NE buffer was added per tip. The polycarbonate tubes were spun twice at 1,000 rpm in a TJ-6 centrifuge. Liquid that had passed through the tips into the tubes was discarded. Samples (50 μl of the dissolved pellet fractions resulting from the lysing procedure) were delivered into the tips and spun for 3–4 minutes in the TJ-6 centrifuge at 1,000 rpm. Eluates were transferred to Eppendorf tubes and the DNA therein was quantitated by running 5–10 μl on a 1% agarose gel.

DNA prepared by the mini cleared lysate procedure was used to verify structures of constructed plasmids.

6.6. Large Scale Cesium Chloride Plasmid Preparation

This procedure was used to obtain large quantities of plasmid DNA with which to construct the recombinant plasmids of this invention.

One liter of plasmid-bearing *E. coli* cells was grown to an optical density (OD$_{600}$) of 0.5 in M9 medium at which time 200 μg/ml chloramphenicol was added for 12–20 hours of amplification. The amplified culture was centrifuged in a Sorvall RC5b at 8,000 rpm for 20 minutes. The pellet fraction was resuspended in 18 ml of cold 25% suscrose in 50 mM Tris, pH 8.0. The cell suspension was transferred to a 250 ml Erlenmeyer flask and kept on ice. In stepwise fashion, 6 ml of lysozyme at a concentration of 5 mg/ml in 250 mM Tris, pH 8.0, was added to the flask and allowed to stand for 10–15 minutes. Next, 6 ml of 250 mM EDTA, pH 8.0, was added and mixed gently; the flask was incubated for another 15 minutes on ice. Finally, 30 ml of a detergent mix of the following composition: 0.01% Triton X-100; 60 mM EDTA, pH 8.0; and 50 mM Tris, pH 8.0, was added to the flask which was then incubated for 30 minutes on ice. After the incubation period, the mixture was centrifuged at 25,000 rpm for 90 minutes in a Sorvall centrifuge with an SW28 rotor at 4° C. Pronase was added to the supernatant fluid to a final concentration of 250 μg/ml and the reaction was run at 37° C. for 30 minutes.

Following incubation, the enzymatically-treated supernatant fluid was extracted once in one-half volume of phenol which had been equilibrated with TE (10 mM Tris, pH 8.0, 1 mM EDTA). The aqueous layer was removed and sodium acetate was added to a concentration of 300 mM followed by two volumes of cold 100% ethanol. These components were mixed thoroughly and held at −20° C. overnight. The mixture was centrifuged and the pellet fraction resuspended in 6 ml TE-10 (10 mM Tris, 10 mM EDTA, pH 8.0). Next, 9.4 grams of cesium chloride (CsCl) were added along with 0.65 ml of ethidium bromide at a concentration of 6 mg/ml. The volume were made up to 10 ml with sterile double-distilled water.

Beckman heat sealable gradient tubes were filled with the mixture and centrifuged at 48,000 rpm for 40 hours in a Ti 70.1 Beckman rotor. Plasmid bands were visualized under ultraviolet light and removed with a syringe and 18 gauge needle by piercing the side of the tube. Ethidium bromide was removed from plasmid fractions by 3 successive extractions with equal volumes of isobutanol. Plasmid fractions were then dialyzed against one 2 liter lot of 10 mM Tris, pH 7.4; 1 mM EDTA, pH 7.5; and 5 mM NaCl for 2 hours or more at 4° C.

After one phenol extraction with one-third volume phenol equilibrated with TE buffer, sodium acetate (NaAc) was added to a concentration of 300 mM along with 2 volumes of 100% ethanol. The plasmid DNA was allowed to precipitate at −20° C. overnight or at −70° C. for 30 minutes. The preparation was centrifuged, dried and resuspended in 2 ml of NE buffer. Plasmid DNA (1 μl) isolated in this manner was quantitated on a 1% agarose gel.

6.7. Gel Purification of DNA Fragments

Either of the following two procedures was used to purify DNA fragments resulting from restriction enzyme and/or nuclease digestions. Fragments so purified were used in further cloning experiments and plasmid constructions or were sequenced by the technique of Maxam and Gilbert [Proc. Natl. Acad. Sci., U.S.A. 74: 560–564 (1977)] to verify structures of recombinant plasmids.

6.7.1. Electro-Elution

After desired restriction or nuclease treatment, DNA fragments of varying sizes were separated by gel electrophoresis in either agarose or polyacrylamide gels at low voltage (approx. 40 volts), stained with ethidium bromide and visualized under ultraviolet (UV) light. The bands were then cut out of the gel. Gel slices were placed in dialysis tubing filled with 1 mM $Na_2EDTA$, 45 mM boric acid, and 45 mM Tris base. The dialysis tubing containing the gel slice was then placed in a tray filled with a 1/10 concentration of the above buffer and subjected to a 150 v current running perpendicular to the gel slice for 3–6 hrs. Sometimes the current was reversed for a 5 minute period to aide in removal of the DNA from the wall of the dialysis tubing. The gel slice was then removed and the DNA-buffer solution collected. The dialysis tubing was then washed once with buffer and this was added to the first volume. The DNA was phenol extracted once with ½–⅓ volume buffer-equilibrated phenol in a siliconized glass tube. The DNA was then ethanol-precipitated with 2–3 vol. of 100% ethanol in a siliconized glass tube with 300 mM sodium acetate and 10 mM magnesium acetate at −20° C., overnight. The precipitate was collected by centrifugation and re-dissolved in NE buffer (5 mM NaCl, 0.1 mM EDTA, pH 8).

6.7.2. Low Melting Temperature Gel

All steps of this procedure were carried out in plastic or siliconized glass tubes. First, electrophoresis of DNA fragments was run in 1% low melting point agarose (Bethesda Research Laboratories, Rockville, MD). After staining the gels with ethidium bromide, DNA bands were visualized with UV light and appropriate gel slices were cut out. The gel slices were melted at 65° C., diluted with 4 volumes of TEA buffer at 65° C. (where TEA buffer is made up of 40 mM Tris base, adjusted to pH 7.9 with acetic acid, 5 mM Sodium acetate, and 1 mM disodium EDTA), and extracted once at 37° C. with ½–⅓ volume phenol which had been equilibrated with TE buffer (10 mM Tris and 1 mM EDTA, pH 8.0). The diluted melted gels were centrifuged to separate layers and the aqueous layers containing DNA were removed. DNA in the samples was precipitated with 300 mM sodium acetate plus 2 volumes of methoxy ethanol (ethylene glycol monomethyl ether from Fisher) either at −20° C. overnight or at −70° C. for 20 minutes. The precipitates were centrifuged, washed with cold 100% ethanol, dried under vacuum, and resuspended in NE buffer (5 mM NaCl and 0.1 mM EDTA, pH 8.0).

6.7.3. DEPOSIT OF MICROORGANISMS

The following *E. coli* strains carrying the listed plasmids have been deposited with the Agricultural Research Culture Collection (NRRL), Peoria, IL and have been assigned the listed accession numbers:

| E. coli Strain | Plasmid | Accession Number |
| --- | --- | --- |
| (1) MC1000 | pJS413 | NRRL B-15237 |
| (2) MC1000 | pDN599 | NRRL B-15238 |
| (3) MC1000 | pDNT413RI⁻ | NRRL B-15239 |
| (4) MC1000 | pSH113 | NRRL B-15240 |
| (5) MC1000 | pMG101 | NRRL B-15241 |
| (6) MC1000 | pJSIIIb | NRRL B-15242 |
| (7) MC1000 | pJS400 | NRRL B-15243 |
| (8) MC1000 | pDN400 | NRRL B-15244 |
| (9) MC1000 | pDN455 | NRRL B-15245 |
| (10) MC1000 | pDNT456RI⁻ | NRRL B-15246 |
| (11) MC1000 | pDH26 | NRRL B-15247 |
| (12) MC1000 | pDH428 | NRRL B-15248 |
| (13) MC1000 (λ) | pDN55 | NRRL B-15249 |
| (14) MC1000 (λ) | pDH511 | NRRL B-15250 |

A culture of the deposited microorganisms will be made available to the public upon the grant of patent based upon the present application. Furthermore, the present invention is not to be limited in scope by the microorganism deposited, since the deposited embodiment is intended as a single illustration of one aspect of the invention. One may construct by techniques known in the art various combinations and permutations of the functional elements of the plasmids described in the present application. Indeed, various other modifications of the invention in addition to such permutations and combinations and those shown and described herein will become apparent to those skilled in the art from the foregoing description and accompanying drawings. It is also to be understood that all base pair sizes given for nucleotide sequences are approximate and are useful for purposes of description. Variations in these sequences leading to functionally equivalent products are intended to be within the scope of the invention. The specific embodiments described are given by way of example only and the invention is limited only by the appended claims.

We claim:

1. A DNA cloning and expression vector capable of incorporating a nucleic acid sequence and providing strong expression without further vector manipulation after ligation of the sequence and of propagating in a microbial host, which comprises from upstream to downstream:

(a) a Plac promoter;

(b) an Olac operator;
(c) a lacZ and a λcro Shine-Dalgarno nucleotide sequence;
(d) a translation start codon encoded by a cro gene amino terminus fragment.
(e) a cloning segment;
(f) a portion of the lacI gene fused to a lacZ gene carboxy-terminal fragment; and
(g) an antibiotic resistance marker.

2. The DNA cloning and expression vector of claim 1, named pJS413, wherein the cloning segment comprises a BglII site, a SmaI site and a BamHI site and is in the (+2) translational phase.

3. The DNA cloning and expression vector of claim 1, named pHK413, wherein the cloning segment comprises a BglII, a HindIII site, a SmaI site, and a BamHI site and is in the (+1) translational phase.

4. The DNA cloning and expression vector of claim 1, named pHK412, wherein the cloning segment comprises a BglII, a HindIII site, a SmaI site and a BamHI site and is in the (0) translational phase.

5. The DNA cloning and expression vector of claim 1, named pHK414, wherein the cloning segment comprises a BglII site, a HindIII site, a SmaI site and a BamHI site and is in the (+2) translational phase.

6. The DNA cloning and expression vector of claim 1, named pHK410, wherein the cloning segment comprises a BglII site, a HindIII site and a BamHI site and is in the (0) translational phase.

7. The DNA cloning and expression vector of claim 1, named pHK411, wherein the cloning segment comprises a BglII site, a HindIII site and a BamHI site and is in the (+1) translational phase.

8. The DNA cloning and expression vector of a claim 1, named pHK420, wherein the cloning segment comprises a BglII site, a HindIII site, a SmaI site and a BamHI site and is in the (0) translational phase.

9. The DNA cloning and expression vector of claim 1, named pHK422, wherein the cloning segment comprises a BglII site, a HindIII site, a SmaI site and a BamHI site and is in the (+2) translational phase.

10. The DNA cloning and expression vector of claim 1, named pSH113, wherein the cloning segment comprises a BglII site, a SmaI site and a BamHI site and is in the (+2) translational phase, further comprising an origin bearing the OP1Δ6 colE1 mutation to provide for increased vector copy number.

11. The DNA cloning and expression vector of claim 1, named pDN413RI−, wherein the cloning segment comprises a BglII site and a BamHI site and is in the (0) translational phase, further comprising a unique EcoRI site upstream of the Plac promoter.

12. A DNA cloning and expression vector capable of incorporating a nucleic acid sequence and providing strong expression without further vector manipulation after ligation of the sequence and of propagating in a microbial host, which comprises from upstream to downstream:
(a) a Plac promoter;
(b) an Olac operator;
(c) a lacZ and a λcro Shine-Dalgarno nucleotide sequence;
(d) a translation start codon encoded by a cro gene amino-terminal fragment, which fragment has been partially deleted by nuclease treatment; (e) a cloning segment; (f) a portion of the lacI gene fused to a lacZ gene carboxy-terminal fragment; and (g) an antibiotic resistance marker.

13. A DNA cloning and expression vector capable of incorporating a nucleic acid sequence and providing strong expression without further vector manipulation after ligation of the sequence and of propagating in a microbial host, which comprises from upstream to downstream:
(a) a Plac promoter;
(b) an Olac operator;
(c) a lacZ Shine-Dalgarno nucleotide sequence;
(d) a translation start codon encoded by a lacZ gene amino-terminal fragment,
(e) a cloning segment comprising an EcoRI site, a SmaI site and a BamHI site;
(f) a lacZ gene carboxy-terminal fragment; and
(g) an ampicillin-resistance marker.

14. The DNA cloning and expression vector of claim 13, named pMG101, which is in the (+2) translational phase.

15. A DNA cloning and expression vector, named pJSIIIb, capable of incorporating a nucleic acid sequence and providing strong expression without further vector manipulation after ligation of the sequence and of propating in a microbial host, which comprises from upstream to downstream:
(a) a Plac promoter;
(b) an Olac operator;
(c) a lacZ Shine-Dalgarno nucleotide sequence;
(d) a translation start codon encoded by lacZ gene amino-terminal fragment;
(e) a cloning segment comprising an EcoRI site and a BamHI site, which segment is in the (0) translational phase;
(f) a lacZ gene carboxy-terminal fragment; and
(g) an ampicillin-resistance marker.

16. A DNA cloning and expression vector capable of incorporating a nucleic acid sequence and providing strong expression without further vector manipulation after ligation of the sequence and of propagating in a microbial host, which comprises from upstream to downstream:
(a) a Plac promoter;
(b) an Olac operator;
(c) a lacZ Shine-Dalgarno nucleotide sequence;
(d) a translation start codon encoded by a lacZ gene amino-terminus fragment;
(e) a cloning segment comprising an EcoRI site, a SmaI site and a BamHI site;
(f) a portion of the lacI gene fused to a lacZ gene carboxy-terminal fragment; and
(g) an ampicillin-resistance marker.

17. The DNA cloning and expression vector of claim 16, named pJS400, which is in the (+1) translational phase.

18. A DNA cloning and expression vector, named pDN400, capable of incorporating a nucleic acid sequence and providing strong expression without further vector manipulation after ligation of the sequence and of propagating in a microbial host, which comprises from upstream to downstream:
(a) a Plac promoter;
(b) an Olac operator;
(c) a lacZ Shine-Dalgarno nucleotide sequence;
(d) a translation start codon encoded by a lacZ gene amino-terminus fragment;
(e) a cloning segment comprising an EcoRI site and a BamHI site, which segment is in the (0) translational phase;

(f) a portion of the lacI gene fused to a lacZ gene carboxy-terminal fragment; and (g) an ampicillin-resistance marker.

19. A DNA cloning and expression vector capable of incorporating a nucleic acid sequence and providing strong expression without further vector manipulation after ligation of the sequence and of propagating in a microbial host, which comprises from upstream to downstream:

(a) a λcI857 regulatory gene coding for a repressor;
(b) a λP$_R$ promoter;
(c) a λO$_R$ operator;
(d) a λcro Shine-Dalgarno nucleotide sequence;
(e) a translation start codon encoded by a cro gene amino-terminal fragment;
(f) a cloning segment;
(g) a portion of the lacI gene fused to a lacZ gene carboxy-terminal fragment; and
(h) an antibiotic resistance marker.

20. The DNA cloning and expression vector of claim 19, named pDN455, wherein the cloning segment comprises a BglII site, a SmaI site, and a BamHI site, and is in the (+2) translational phase.

21. The DNA cloning and expression vector of claim 19, named pDN456, wherein the cloning segment comprises a BglII site, and is in the (0) translational phase.

22. The DNA cloning and expression vector of claim 19 in which the λcro gene amino-terminal fragment has been partially or totally deleted by nuclease treatment.

23. A DNA cloning and expression vector capable of incorporating a nucleic acid sequence and providing strong expression without further vector manipulation after ligation of the sequence and of propagating in a microbial host, which comprises from upstream to downstream:

(a) a λP$_L$ promoter;
(b) a λO$_L$ operator;
(c) a λnut L site;
(d) a λN Shine-Dalgarno nucleotide sequence;
(e) a translation start codon encoded by a λN gene amino-terminal fragment;
(f) a cloning segment;
(g) a lacZ gene carboxy-terminal fragment; and
(h) an amplicillin-resistance marker.

24. The DNA cloning and expression vector of claim 23, named pDH26, wherein the cloning segment comprises a BamHI site and is in the (0) translational phase, and which further includes a segment upstream of the λP$_L$ promoter which comprises from upstream to downstream:

(a) a λP$_R$ promoter;
(b) a λO$_R$ operator;
(c) a λcI857 regulatory gene coding for repressor; and
(d) a λrex gene.

25. The DNA cloning and expression vector of claim 23, named pDH36, wherein the cloning segment comprises a first BamHI site, a SmaI site and a second BamHI site and is in the (+1) translational phase, and which further includes a segment upstream of the λP$_L$ promoter which comprises from upstream to downstream:

(a) a λP$_R$ promoter;
(b) a λO$_R$ operator;
(c) a λcI857 regulatory gene coding for repressor; and
(d) a λrex gene.

26. The DNA cloning and expression vector of claim 23, named pDH72, wherein the cloning segment comprises a first BamHI, a SmaI site and a second BamHI site, and is in the (+1) translational phase.

27. A DNA cloning and expression vector capable of incorporating a nucleic acid sequence and providing strong expression without further vector manipulation after ligation of the sequence and of propagating in a microbial host, which comprises from upstream to downstream:

(a) a λP$_L$ promoter;
(b) a λO$_L$ operator;
(c) a cloning segment comprising a HindIII site;
(d) a tetracycline-resistanee marker; and
(e) an ampicillin-resistance marker.

28. The DNA cloning vector of claim 27, further comprising a λnutL sequence between the operator and the cloning segment.

29. A DNA cloning and expression vector capable of incorporating a nucleic acid sequence and providing strong expression without further vector manipulation after ligation of the sequence and of propagating in a microbial host, which comprises from upstream to downstream:

(a) a lacZ and a λcro Shine-Dalgarno nucleotide sequence;
(b) a translation start condon encoded by a λcro gene amino terminus fragment;
(c) a cloning segment comprising a BglII site, a SmaI site and a BamHI site;
(d) a portion of the lacI gene fused to a lacZ gene carboxy-terminal fragment; and
(e) an ampicillin-resistance marker.

30. The DNA cloning and expression vector of claim 29 which further comprises from upstream to downstream, upstream of the Shine-Dalgarno nucleotide sequence:

(a) a λP$_L$ promoter
(b) a λO$_L$ operator.

31. The DNA cloning and expression vector of claim 30 which further comprises a λnutL sequence downstream of the λO$_L$ operator.

32. The DNA cloning and expression vector of claim 30 which further comprises from upstream to downstream, upstream of the λP$_L$ promoter:

(a) a λcI857 regulatory gene coding for repressor;
(b) a λP$_R$ promoter; and
(c) a λO$_R$ operator.

33. A DNA cloning and expression vector capable of incorporating a nucleic acid sequence and providing strong expression without further vector manipulation after ligation of the sequence and of propagating in a microbial host, which comprises from upstream to downstream:

(a) a λP$_L$ promoter;
(b) a λnutL sequence;
(c) a λN Shine-Dalgarno nucleotide sequence;
(d) a λN gene comprising a unique HpaI site; and
(e) an ampicillin-resistance marker.

34. The DNA cloning and expression vector of claim 33, named pDN55, which further comprises a SalI site just upstream of the P$_L$-O$_L$ region.

35. A DNA cloning and expression vector capable of incorporating a nucleic acid sequence and providing strong expression without further vector manipulation after ligation of the sequence and of propagating in a microbial host, which comprises from upstream to downstream:

(a) a partially deleted λP$_L$-λO$_L$ promoter-operator region, consisting of the nucleotide sequence AAAAAACATACAGATAAC-CATCTGCGGTGATAAAT-TATCTCTGGCGGTGATACTGAGCACAT-CAG;
(b) a λnut L sequence;
(c) a λN Shine-Dalgarno nucleotide sequence;
(d) a translation start codon encoded by a λN gene amino-terminal fragment;
(e) a cloning segment;
(f) a lacZ gene carboxy-terminal fragment; and
(g) an ampicillin-resistance marker.

36. The DNA cloning and expression vector of claim 33, named pDH428, wherein the cloning segment comprises a BamHI site and is in the (0) translational phase.

37. The DNA cloning and expression vector of claim 33, named pDH438, wherein the cloning segment comprises a first BamHI site, a SmaI site and a second BamHI site and is in the (+1) translational phase.

38. The DNA cloning and expression vector of claim 21, named pDNT456RI$^-$, containing a unique EcoRI site upstream of the cI857 regulatory gene.

* * * * *